United States Patent [19]

Nakamura

[11] Patent Number: 4,840,887

[45] Date of Patent: Jun. 20, 1989

[54] SILVER HALIDE PHOTOGRAPHIC MATERIALS

[75] Inventor: Koki Nakamura, Kanagawa, Japan

[73] Assignee: Fuji Photo Film Co., Ltd., Japan

[21] Appl. No.: 188,779

[22] Filed: Apr. 29, 1988

[30] Foreign Application Priority Data

Apr. 30, 1987 [JP] Japan ................................ 62-106885

[51] Int. Cl.[4] ......................... G03C 1/02; G03C 1/46; G03C 1/08; G03C 1/06

[52] U.S. Cl. .................................... 430/564; 430/443; 430/493; 430/505; 430/542; 430/544; 430/546; 430/600; 430/603; 430/613; 430/955; 430/957; 430/958

[58] Field of Search ............... 430/443, 493, 505, 542, 430/544, 546, 564, 600, 603, 613, 955, 957, 958

[56] References Cited

U.S. PATENT DOCUMENTS

| | | | |
|---|---|---|---|
| 3,980,479 | 9/1976 | Fields et al. | 430/218 |
| 4,139,379 | 2/1979 | Chasman et al. | 430/223 |
| 4,199,354 | 4/1980 | Hinshaw et al. | 430/219 |
| 4,232,107 | 11/1980 | Janssens | 430/217 |
| 4,639,408 | 1/1987 | Kitaguchi et al. | 430/351 |
| 4,678,739 | 7/1987 | Kitaguchi et al. | 430/353 |
| 4,684,604 | 8/1987 | Harder | 430/375 |
| 4,695,525 | 9/1987 | Tsukase et al. | 430/957 |
| 4,698,297 | 10/1987 | Ichijima et al. | 430/383 |
| 4,729,936 | 3/1988 | Kitaguchi et al. | 430/955 |
| 4,734,357 | 3/1988 | Mihayashi et al. | 430/376 |
| 4,770,982 | 9/1988 | Ichijima et al. | 430/505 |
| 4,770,990 | 9/1988 | Nakamura et al. | 430/564 |
| 4,791,049 | 12/1988 | Kojima et al. | 430/544 |

FOREIGN PATENT DOCUMENTS

| | | |
|---|---|---|
| 0187343 | 7/1986 | European Pat. Off. . |
| 0220746 | 5/1987 | European Pat. Off. . |
| 2062352 | 3/1987 | Japan . |
| 1464104 | 2/1977 | United Kingdom . |

*Primary Examiner*—Mukund J. Shah

*Attorney, Agent, or Firm*—Sughrue, Mion, Zinn, Macpeak & Seas

[57] ABSTRACT

A silver halide photographic material is disclosed, which comprises a support having formed thereon at least one silver halide emulsion layer, wherein the silver halide photographic material contains, in the silver halide emulsion layer, other hydrophilic colloid layer(s), or both, a compound represented by formula (I)

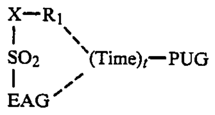

(I)

wherein EAG represents an electron accepting group, —$SO_2$— represents a sulfonylene group; X represents an oxygen atom (—O—), a sulfur atom (—S—) or an atomic group (—$N(R_2)$—) containing a nitrogen atom; the single bond between —$SO_2$ and X being cleaved after EAG receives an electron, wherein $R_1$ and $R_2$ each represents a simple bond or a group other than a hydrogen atom; said $R_1$, $R_2$, EAG may be combined with each other to form a ring; (Time) represents a group capable of releasing a photographically useful group (PUG) upon the cleavage of the $SO_2$—X bond; t represents 0 or 1; when said t is 0, (Time) represents a simple bond and X may be a part of PUG; the solid line represents a bond; the dotted lines show that at least one of them is bonded.

10 Claims, No Drawings

SILVER HALIDE PHOTOGRAPHIC MATERIALS

FIELD OF THE INVENTION

This invention relates to a silver halide photographic material, and more particularly to a silver halide photographic material containing a novel compound capable, or reduction, of a photographically useful group upon the cleavage of a single bond between the sulfonyl group thereof and a nitrogen, oxygen or sulfur atom therof.

BACKGROUND OF THE INVENTION

Compounds providing a photographic reagent which is originally immobile, balasted or blocked at the active position include positive working compounds disclosed in Belgian Pat. No. 810,195, U.S. Pat. Nos. 4,199,354, 3,980,479, and 4,139,379, and Japanese Patent Application (OPI) No. 130,927/79. The term "OPI" as used herein indicates an "unexamined published application" These compounds are immobile or photographically inactive but can release a mobable photographically useful group by causing an intramolecular nucleophilic substitution reaction or an intramolecular electron transfer reaction.

The aforesaid compounds having the function as described above provide many advantages. However, it is more preferred to improve the characteristics and possibility of the positive working compounds for further increasing the freedom of the designing and latitude on the preparation and processing of photographic elements. It is far more preferred if it is possible to provide compounds having better stability in photographic elements before and after photographic processing. Also, it is preferred to provide a good means for controlling the release of a photographically useful component.

SUMMARY OF THE INVENTION

The object of this invention is to provide a silver halide photographic material containing a novel compound which is stable to acid, alkali and heat but the single bond thereof between the sulfonyl group and a nitrogen, oxygen or sulfur atom is easily cleaved, by receiving an electron from a reducing product usually used for photography, to release a photographically useful group.

As the result of investigation by selecting a single bond between a sulfonyl group and nitrogen, oxygen, or sulfur atom as a bond which is stable to acid, alkali and heat but is readily cleaved on reduction, the following has been discovered in the present invention.

It is known that the stability of a single bond of sulfonyl group and a nitrogen, oxygen, or sulfur atom is greatly changed according to the kind of substituent and it has been confirmed that by selecting a proper substituent, the aforesaid single bond has a sufficient stability for photographic systems. Furthermore, as the result of intensitive invenstigations for enabling the reduction cleavage of the single bond between a sulfonyl group and nitrogen, oxygen or sulfur by a compound known as a reducing agent for photography, it has been discovered in the present invention, that the single bond between a sulfonyl group and nitrogen, oxygen or sulfur can be cleaved by bonding an electron accepting group to the sulfonyl group.

Since in the compound thus designed and synthesized, the cleavage of the single bond between the sulfonyl group and nitrogen, oxygen or sulfur becomes substantially irreversible, the cleavage reaction proceeds at an astonishingly higher speed than that expected in an oxydation reduction equillibrium system. This gives an advantage in that as to the reducing material for the cleavage reaction, a stable reducing agent capable of sufficiently enduring the oxidation by oxygen in air can be used.

The detail mechanism of the cleavage reaction of the single bond between the sulfonyl group and nitrogen, oxygen or sulfur atom in this invention has not yet been clarified at present but it is assumed to proceed by the mechanism similar to a series of reactions described in Angewante Chemie International Edition, Vol. 14, NO. 11, 734 (1975).

That is, the compound of this invention received an electron from a reducing material to become an anion radical and the reducing material becomes a one-electron oxidation product. The reaction is considered to be in equilibrium but since the anion radical intermediate irreversibly occurs in the direction of the cleavage of the nitrogen-oxygen single bond, the reaction is, on the whole considered to easily proceed to a direction of releasing a photographically useful group.

This invention has been made with the aforesaid techniques as the background. That is, when a electron acceptive group is bonded to a group forming the single bond of the sulfonyl group and a nitrogen, oxygen, or sulfur atom and the electron accepting group accepts an electron, the single bond of the sulfonyl group and a nitrogen, oxygen or sulfur atom is cut. In this case, the compound of this invention acts with the sulfonyl group, nitrogen atom, oxygen atom, or sulfur atom in a deblocked form as a trigger and acts to release a photographically useful group.

Thus, according to this invention, there is provided a silver halide photographic material containing a novel compound represented by following formula (I) having the function described above;

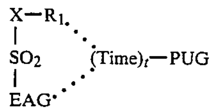

(I)

wherein EAG represents a group accepting an electron from a reducing material; $-SO_2-$ represents a sulfonylene group; X represents an oxygen atom (—O—), a sulfur atom (—S—) or an atomic group ($-N(R_2)-$) including a nitrogen atom, the single bond between $-SO_2-$ and X being cleaved after EAG receives an electron; (Time) represents a group releasing PUG, by a reduction reaction, upon the cleavage of the single bond of $SO_2-X$; $(Time)_t-PUG$ bond to at least one of $R_1$, $R_2$ and EAG; t represents 0 or 1; when t is 0, (Time) represents a simple bond and X may be a part of PUG; the solid line represents a bond; the dotted lines indicate that at least one of them is bonded; and $R_1$ and $R_2$ each represents a simple bond or a substituent other than a hydrogen atom.

DETAILED DESCRIPTION OF THE INVENTION

In formula (I), $R_1$ and $R_2$ each preferably represents an alkyl group, an aralkyl group, an aryl group, a heterocyclic group, an acyl group, a carbamoyl group, a sulfamoyl group, or a sulfonyl group.

$R_1$ and $R_2$ are practically an alkyl or aralkyl group, which may be substituted (e.g., a methyl group, a trifluoromethyl group, a benzyl group, a chloromethyl group, a dimethylaminomethyl group, an ethoxycarbonylmethyl group, an aminomethyl group, an acetylaminomethyl group, an ethyl group, a 2-(4-dodecanoylaminophenyl)ethyl group, a carboxyethyl group, an allyl group, a 3,3,3-trichloropropyl group, a n-propyl group, an iso-propyl group, a n-butyl group, an iso-butyl group, a sec-butyl group, a t-butyl group, a n-pentyl group, a sec-pentyl group, a t-pentyl groul, a cyclopentyl group, a n-hexyl group, a sec-hexyl group, a t-hexyl group, a cyclohexyl group, a n-octyl group, a sec-octyl group, a t-octyl group, a n-decyl group, a n-undecyl group, a n-dodecyl group, a n-tetradecyl group, a n-pentadecyl group, a n-hexadecyl group, a sec-hexadecyl group, a t-hexadecyl group, a n-octadecyl group, a t-octadecyl group, etc.); an alkenyl group which may be substituted (e.g., vinyl group, a 2-chlorovinyl group, a 1-methylvinyl group, a 2-cyanovinyl group, a cyclohexen-1-yl group, etc.); an alkynyl group which may be substituted (e.g., an ethynyl group, a 1-propynyl group, a 2-ethoxycarbonylethynyl group, etc.); an aryl group which may be substituted (e.g., a phenyl group, a naphthyl group, a 3-hydroxyphenyl group, a 3-chlorophenyl group, a 4-acetylaminophenyl group, a 4-hexadecanesulfonylaminophenyl group, a 2-methanesulfonyl-4-nitrophenyl group, a 3-nitrophenyl group, a 4-methoxyphenyl group, a 4-acetylaminophenyl group, a 4-methanesulfonylphenyl group, a 2,4-dimethylphenyl group, a 4-tetradecyloxyphenyl group, etc.); a heterocyclic group which may be substituted (e.g., a 1-imidazolyl group, a 2-furyl group, a 2-pyridyl group, a 5-nitro-2-pyridyl group, a 3-pyridyl group, a 3,5-dicyano-2-pyridyl group, a 5-tetrazolyl group, a 5-phenyl-1-tetrazolyl group, a 2-benzthiazolyl group, a 2-benzimidazolyl group, a 2-benzoxazolyl group, a 2-oxazolin-2-yl group, a morpholino group, etc.); an acyl group which may be substituted (e.g., an acetyl group, a propionyl group, a butyroyl group, an iso-butyroyl group, a 2,2-dimethylpropionyl group, a benzoyl group, a 3,4-dichlorobenzoyl group, a 3-acetylamino-4-methoxybenzoyl group, a 4-methylbenzoyl group, a 4-methoxy-3-sulfobenzoyl group, etc.); a sulfonyl group which may be substituted (e.g., a methanesulfonyl group, an ethanesulfonyl group, a chloromethanesulfonyl group, a propanesulfonyl group, a butanesulfonyl group, a n-octanesulfonyl group, a n-dodecanesulfonyl group, a n-hexadecanesulfonyl group, a benzenesulfonyl group, a 4-toluenesulfonyl group, a 4-n-dodecyloxybenzenesulfonyl group, etc.); a carbamoyl group which may be substituted (e..g, a carbamoyl group, a methylcarbamoyl group, a dimethylcarbamoyl group, a bis-(2-methoxyethyl)carbamoyl group, a diethylcarbamoyl group, a cyclohexylcarbamoyl group, a di-n-octylcarbamoyl group, a 3-dodecyloxypropylcarbamoyl group, a hexadecylcarbamoyl group, a 3-(2,4-di-t-pentylphenoxy)propylcarbamoyl group, a 3-octanesulfonylaminophenylcarbamoyl group, a di-n-octadecylcarbamoyl group, etc.); or a sulfamoyl group which may be substituted (e.g., a sulfamoyl group, a methylsulfamoyl group, a dimethylsulfamoyl group, a diethylsulfamoyl group, a bis-(2-methoxyethyl)sulfamoyl group, a di-n-butylsulfamoyl group, a methyl-n-octylsulfamoyl group, a n-hexadecylmethylsulfamoyl group, a 3-ethoxypropylmethylsulfamoyl group, an N-phenyl-N-methylsulfamoyl group, a 4-decyloxyphenylsulfamoyl group, a methyloctadecylsulfamoyl group, etc.).

When $R_1$ and $R_2$ are bonded to $(Time)_t$—PUG, they may be a simple bond. Also, $R_1$, $R_2$, and EAG may be combined with each other to form 5- to 8-membered ring.

The compound shown by formula (I) described above is preferably shown by following formula (II) for increasing the tolerance and freedom on the characteristics of the positive working compound and the synthetical design thereof.

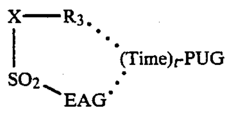

(II)

wherein $R_3$ represents an atomic group forming a 5- to 8-membered heterocyclic ring by combining with X and EAG; and $—SO_2—$, X, EAG, (Time), PUG, and t have the same meaning as defined above in formula (I).

EAG will be explained below in detail.

EAG represents an aromatic group accepting an electron from a reducing material and bonds to a nitrogen atom. It is preferred that EAG is shown by following formula (A)

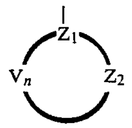

(A)

wherein $Z_1$ represents

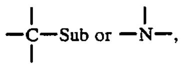

$V_n$ represents an atomic group forming a 3- to 8-membered aromatic and n represents an integer of from 3 to 8.

$V_n$ in formula (A) is as follows: $V_3$ is $—Z_3—$, $V_4$ is $—Z_3—Z_4—$, $V_5$ is $—Z_3—Z_4—Z_5—$, $V_6$ is $—Z_3—Z_4—Z_5—Z_6—$, $V_7$ is $—Z_3—Z_4—Z_5—Z_6—Z_7—$, and $V_8$ is $—Z_3—Z_4—Z_5—Z_6—Z_7—Z_8—$.

Also, $Z_2$ to $Z_8$ each represents

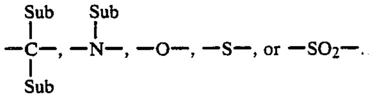

Sub represents a simple bond (π-bond), a hydrogen atom, or a substituent shown below. When two Subs exist, they may be the same or different, or may combine with each other to form a 3- to 8-membered saturated or unsaturated carbon ring or heterocyclic ring.

On formula (A), Sub is selected to that the total sum of the Hammett's substitution constants sigma and para of the substituents become +0.50 or more, preferably +0.70 or more, and most preferably +0.85 or more.

When Sub described above represents a substituent, the substituent has from 0 to 40 carbon atoms and examples thereof are a nitro group, a nitroso group, a cyano group, a carboxy group, a sulfo group, a sulfino group, a sulfeno group, a mercapto group, an isocyano group, a thiocyano hydroxy group, a halogen atom (e.g., a fluorine atom, a chlorine atom, an iodine atom, etc.), an iodosil group, an iodyl group, a diazo group, an azido group, an alkyl or an aralkyl group, which may be substituted, (e.g., a methyl grup, a trifluoromethyl group, a benzyl group, a chloromethyl group, a dimethylaminomethyl group, an ethoxycarbonylmethyl group, an aminomethyl group, an acetylaminomethyl group, an ethyl group, a 2-(4-dodecanoylaminophenyl-)ethyl group, a carboxyethyl group, an allyl group, a 3,3,3-tricholoropropyl group, a n-propyl group, an iso-propyl group, a n-butyl group, an iso-butyl group, a sec-butyl group, a t-butyl group, a n-pentyl group, a sec-pentyl group, a t-pentyl group, a cyclopentyl group, a n-hexyl group, a sec-hexyl group, a t-hexyl group, a cyclohexyl group, a n-octyl group, a sec-octyl group, a t-octyl group, a n-decyl group, a n-undecyl group, a n-dodecyl group, a n-tetradecyl group, a n-pentadecyl group, a n-hexadecyl group, a sec-hexadecyl group, a t-hexadecyl group, a n-octadecyl group, a t-octadecyl group, etc.), an alkenyl group which may be substituted (e.g., a vinyl group, a 2-chlorovinyl group, a 1-methylvinyl group, a 2-cyanovinyl group, a cyclohexen-1-yl group, etc.), an alkynyl group which may be substituted (e.g., an ethynyl group, a 1-propynyl group, a 2-ethoxycarbonylethynyl group, etc.), an aryl group which may be substituted (e.g., a phenyl group, a naphthyl group, a 3-hydroxyphenyl group, a 3-chlorophenyl group, a 4-acetylaminophenyl group, a 4-hexadecanesulfonylaminophenyl group, a 2-methanesulfonyl-4-nitrophenyl gorup, a 3-nitrophenyl group, a 4-methoxyphenyl group, a 4-acetylaminophenyl group, a 4-methanesulfonylphenyl group, a 2,4-dimethylphenyl group, a 4-tetradecyloxyphenyl group, etc.), a heterocyclic group which may be substituted (e.g., a 1-imidazolyl group, a 2-furyl group, a 2-pyridyl group, a 5-nitro-2-pyridyl group, a 3-pyridyl group, a 3,5-dicyano-2-pyridyl group, a 5-tetrazolyl group, a 5-phenyl-1-tetrazolyl group, a 2-benzthiazolyl group, a 2-benzimidazolyl group, a 2-benzoxazolyl group, a 2-oxazolin-2-yl group, a morpholino group, etc.), an acyl group which may be substituted (e.g., an acetyl group, a porpionyl group, a butyroyl group, an iso-butyroyl group, a 2,2-dimthylpropionyl group, a benzoyl group, a 3,4-dichlorobenzoyl group, a 3-acetylamino-4-methoxybenzoyl group, a 4-methylbenzoyl group, a 4-methoxy-3-sulfobenzoyl group, etc.), a sulfonyl group which may be substituted (e.g., a methanesulfonyl group, an ethanesulfonyl group, a chloromethanesulfonyl group, a propanesulfonyl group, a butanesulfonyl group, a n-octanesulfonyl group, a n-dodecanesulfonyl group, a n-hexadecanesulfonyl group, a benzenesulfonyl group, a 4-toluenesulfonyl group, a 4-n-dodecyloxybenzenesulfonyl group, etc.), an amino group which may be substituted (e.g., an amino group, a methylamino group, a dimethylamino group, an ethylamino group, an ethyl-3-carboxypropylamino group, an ethyl-2-sulfoethylamino group, a phenylamino group, a methylphenylamino group, a methyloctylamino group, a methylhexadecylamino group, etc.), an alkoxy group which may be substituted (e.g., a methoxy group, an ethoxy group, a n-propyloxy group, an iso-propuloxy group, a cyclohexylmethoxy group, etc.), an aryloxy or heteroaryloxy group which may be substituted (e.g., a phenoxy group, a naphthyloxy group, a 4-acetylaminophenoxy group, a pyrimidin-2-yloxy group, a 2-pyridyloxy group, etc.), an alkylthio group which may be substituted (e.g., a methylthio group, an ethylthio group, a n-butylthio group, a n-octylthio group, a t-octylthio group, a n-dodecylthio group, a n-hexadecylthio group, an ethoxycarbonylmethylthio group, a benzylthio group, a 2-hydroxyethylthio group, etc.), an arylthio or heteroarylthio group which may be substituted (e.g., a phenylthio group, a 4-chlorophenylthio group, a 2-n-butoxy-5-octylphenylthio group, a 4-nitrophenylthio group, a 2-nitrophenylthio group, a 4-acetylaminophenylthio group, a 1-phenyl-5-tetrazolylthio group, a 5-methanesulfonylbenzothiazol-2-ylthio group, etc.), an ammonio group which may be substituted (e.g., an ammonio group, a trimethylammonio group, a phenyldimethylammonio group, a dimethylbenzylammonio group, a tri-n-butylmmonio group, etc.), a carbamoyl group which may be substituted (e.g., a carbamoyl group, a methylcarbamoyl group, a dimethylcarbamoyl group, a bis-(2-methoxyethyl)carbamoyl group, a diethylcarbamoyl group, a cyclohexylcarbamoyl group, a di-n-octylcarbamoyl group, a 3-dodecyloxypropylcarbamoyl group, a hexadecylcarbamoyl group, a 3-(2,4-di-t-pentylphenoxy)propylcarbamoyl group, a 3-octanesulfonylaminophenylcarbamoyl group, a di-n-octadecylcarbamoyl group, etc.), a sulfamoyl group which may be substituted (e.g., a sulfamoyl group, a methylsulfamoyl group, a dimethylsulfamoyl group, a diethylsulfamoyl group, a bis-(2-methoxyethyl)sulfamoyl group, a di-n-butylsulfamoyl group, a methyl-n-octylsulfamoyl group, a n-hexadecylmethylsulfamoyl group, a 3-ethoxypropylmethylsulfamoyl group, an N-phenyl-N-methylsulfamoyl group, a 4-decyloxyphenylsulfamoyl group, a methyloctadecylsulfamoyl group, etc.), an acylamino group which may be substituted (e.g., an acetylamino group, a 2-carboxybenzoylamino group, a 3-nitrobenzoylamino group, a 3-diethylaminopropanoylamino group, an acryloylamino group, etc.), an acyloxy group which may be substituted (e.g., an acetoxy group, a benzoyloxy group, a 2-butenoyloxy group, a 2-methylporpanoyloxy group, a 3-(chloro-4-tetradecyloxybenzoyloxy group, etc.), a sulfonylamino group which may be substituted (e.g., a methanesulfonylamino group, a benzenesulfonylamino group, a 2-methoxy-5-n-methylbenzenesulfonylamino group, a 2-chloro-5-dodecanoylaminobenzenesulfonylamino group, etc.), an alkoxycarbonylamino group which may be substituted (e.g., a methoxycarbonylamino group, an ethoxycarbonylamino group, a 2-methoxyethoxycarbonylamino group, an iso-butoxycarbonylamino group, a benzyloxycarbonylamino group, a t-butoxycarbonylamino group, a 2-cyanoethoxycarbonylamino group, etc.), an aryloxycarbonylamino group which may be substituted (e.g., a phenoxycarbonylamino group, a 2,4-dimethylphenoxycarbonylamino group, a 4-nitrophenoxycarbonylamino group, a 4-t-butoxyphenoxycarbonylamino group, etc.), an alkoxycarbonyloxy group which may be substituted (e.g., a methoxycarbonyloxy group, a t-butoxycarbonyloxy group, a 2-benzenesulfonylethoxycarbonyloxy group, an n-decyloxycarbonyloxy group, a benzyloxycarbonyloxy group, etc.), an aryloxycarbonyloxy group which may be substituted (e.g., a phenoxycarbonyloxy group, a 3-cyanophenoxycarbonyloxy group, a 4-acetoxyphenoxycarbonyloxy group, a 4-t-butoxycarbonylaminophenoxycarbonyloxy group, a 4-hydroxy-3-benzenesulfonylaminophenoxycarbonyloxy group, etc.), an aminocarbonylamin group which may be substituted (e.g., a methylaminocarbonylamino group, a morpholinocarbonylamino group, a diethylaminocarbonylamino group, an N-ethyl-N-phenylaminocarbonylamino group, a 4-cyanophenylaminocarbonylamino group, a 4-methanesulfonylaminocarbonylamino group, etc.), an aminocarbonyloxy group which may be substituted (e.g., a dimethylaminocarbonyloxy group, a pyrrolidinocarbonyloxy group, a 4-dipropylaminophenylamino group, etc.), and an aminosulfonylamino group which may be substituted (e.g., a diethylaminosulfonylamino group, a di-n-butylamino group, a phenylaminosulfonyl group, etc.).

EAG represents a group accepting an electron from a reducing material and bonds to a nitrogen atom as described above. EAG is preferably an aryl group or a heterocyclic group each substituted by at least one electron attractive group. The substituent bonding to the aryl group or the hterocyclic group shown by EAG can be utilized for controlling the properties of the compound on the whole. For example, the property of easily accepting an electron can be controlled as well as other properties such as the water solubility, oil solubility, diffusibility, subliming property, melting point, duffusibility for a binder such as gelatin, etc., reactivity for a nucleophilic group, reactivity for an electrophilic group, etc., can be controlled.

Examples of the aryl group substituted by at least one electron attracting group are a 4-nitrophenyl group, a 2-nitrophenyl group, a 2-nitro-4-N-methyl-N-n-butylsulfamoyl group, a 2-nitro-4-N-methyl-N-n-octylsulfamoylphenyl group, a 2-nitro-4-N-methyl-N-n-dodecylsulfamoylphenyl group, a 2-nitro-4-N-methyl-N-n-hexadecylsulfamoylphenyl group, a 2-nitro-4-N-methyl-N-n-octadecylsulfamoylphenyl group, a 2-nitro-4-N-methyl-N-(3-carboxypropyl)sulfamoylphenyl group, a 2-nitro-4-N-ethyl-N-(2-sulfoethyl)sulfamoylphenyl group, a 2-nitro-4-N-n-hexadecyl-N-(3-sulfopropyl)sulfamoylphenyl group, a 2-nitro-4-N-(2-cyanoethyl)-N-[(2-hydroxyethoxy)ethyl]sulfamoylphenyl group, a 2-nitro-4-diethylsulfamoylphenyl group, a 2-nitro-4-di-n-butylsulfamoylphenyl group, a 2-nitro-4-di-n-octylsulfamoylphenyl group, a 2-nitro-4-di-n-octadecylsulfamoylphenyl group, a 2-nitro-4-methylsulfamoylphenyl group, a 2-nitro-4-n-hexadecylsulfamoylphenyl group, a 2-nitro-4-N-methyl-N-(4-dodecylsulfonylphenyl)sulfamoylphenyl group, a 2-nitro-4-(3-methylsulfamoylphenyl)sulfamoylphenyl group, a 4-nitro-2-N-methyl-N-n-butylsulfamoylphenyl group, a 4-nitro-2-N-methyl-N-n-octylsulfamoylphenyl group, a 4-nitro-2-N-methyl-N-n-dodecylsulfamoylphenyl group, a 4-nitro-2-N-methyl-N-n-hexadecylsulfamoylphenyl group, a 4-nitro-2-N-methyl-N-n-octedecylsulfamoylphenyl group, a 4-nitro-2-N-methyl-N-(3-carboxypropyl)sulfamoylphenyl group, a 4-nitro-2-N-ethyl-N-(2-sulfoethyl)sulfamoylphenyl group, a 4-nitro-2-N-n-hexadecyl-N-(3-sulfopropyl)sulfamoylphenyl group, a 4-nitro-2-N-(2-cyanoethyl)-N-[(2-hydroxyethoxy)ethyl]sulfamoylphenyl group, a 4-nitro-2-diethylsulfamoylphenyl group, a 4-nitro-2-di-n-butylsulfamoylphenyl group, a 4-nitro-2-di-n-octylsulfamoylphenyl group, a 4-nitro-2-di-n-octadecylsulfamoylphenyl group, a 4-nitro-2-methylsulfamoylphenyl group, a 4-nitro-2-n-hexadecylsulfamoylphenyl group, a 4-nitro-2-N-methyl-N-(4-dodecylsulfonylphenyl)sulfamoylphenyl group, a 4-nitro-2-(3-methylsulfamoylphenyl)sulfamoylphenyl group, a 4-nitro-2-chlorophenyl group, a 2-nitro-4-chlorophenyl group, a 2-nitro-4-N-methyl-N-n-butylcarbamoylphenyl group, a 2-nitro-4-N-methyl-N-n-octylcarbamoylphenyl group, a 2-nitro-N-4-N-methyl-N-n-dodecylcarbamoylphenyl group, a 2-nitro-4-methyl-N-n-hexadecylcarbamoylphenyl group, a 2-nitro-4-N-methyl-N-n-octadecylcarbamoylphenyl group, a 2-nitro-4-methyl-N-(3-carboxypropyl)carbamoylphenyl group, a 2-nitro-4-N-ethyl-N-(2-sulfoethyl)carbamoylphenyl group, a 2-nitro-4-N-n-hexadecyl-N-(3-sulfopropyl)carbamoylphenyl group, a 2-nitro-4-N-(2-cyanoethyl)-N-[(2-hydroxyethoxy)ethyl]-carbamoylphenyl group, a 2-nitro-4-diethylcarbamoylphenyl group, a 2-nitro-4-di-n-butylcarbamoylphenyl group, a 2-nitro-4-di-n-octylcarbamoylphenyl group, a 2-nitro-4-di-n-octadecylcarbamoylphenyl group, a 2-nitro-4-methylcarbamoylphenyl group, a 2-nitro-4-n-hexadecylcarbamoylphenyl group, a 2-nitro-4-N-methyl-N-(4-dodecylsulfonylphenyl)carbamoylphenyl group, a 2-nitro-4-(3-methylsulfamoylphenyl)carbamoylphenyl group, a 4-nitro-2-N-methyl-N-n-butylcarbamoylphenyl group, a 4-nitro-2-N-methyl-N-n-octylcarbamoylphenyl group, a 4-nitro-2-N-methyl-N-n-dodecylcarbamoylphenyl group, a 4-nitro-2-N-methyl-N-n-hexadecylcarbamoylphenyl group, a 4-nitro-2-N-methyl-N-n-octadecylcarbamoylphenyl group, a 4-nitro-2-N-methyl-N-(3-carboxypropyl)carbamoylphenyl group, a 4-nitro-2-N-ethyl-N-(2-sulfoethyl)carbamoylphenyl group, a 4-nitro-2-N-n-hexadecyl-N-(3-sulfopropyl)carbamoylphenyl group, a 4-nitro-2-N-(2-cyanoethyl)-N-[(2-hydroxyethoxy)ethyl]carbamoylphenyl group, a 4-nitro-2-diethylcarbamoylphenyl group, a 4-nitro-2-di-n-butylcarbamoylphenyl group, a 4-nitro-2-di-n-octylcarbamoylphenyl group, a 4-nitro-2-di-n-octadecylcarbamoylphenyl group, a 4-nitro-2-methylcarbamoylphenyl group, a 4-nitro-2-n-hexadecylcarbamoylphenyl group, a 4-nitro-2-N-methyl-N-(4-dodecylsulfonylphenyl)carbamoylphenyl group, a 4-nitro-2-(3-methylsulfamoylphenyl)carbamoylphenyl group, a 2,4-dimethanesulfonylphenyl group, a 2-methanesulfonyl-4-benzenesulfonylphenyl group, a 2-n-octanesulfonyl-4-methanesulfonylphenyl group, a 2-n-tetradecanesulfonyl-4-methanesulfonylphenyl group, a 2-n-hexadecanesulfonyl-4-methanesulfonylphenyl group, a 2,4-di-n-dodecanesulfonylphenyl group, a 2,4-didodecanesulfonyl-5-trifluoromethylphenyl group, a 2-n-decanesulfonyl-4-cyano-5-trifluoromethylphenyl group, a 2-cyano-4-methanesulfonylphenyl group, a 2,4,6-tricyanophenyl group, a 2,4-dicyanophenyl group, a 2-nitro-4-methanesulfonylphenyl group, a 2-nitro-4-n-dodecanesulfonylphenyl group, a 2-nitro-4-(2-sulfoethylsulfonyl)phenyl group, a 2-nitro-4-carboxymethylsulfonylphenyl group, a 2-nitro-4-carboxyphenyl group, a 2-nitro-4-ethoxycarbonyl-5-n-butoxyphenyl group, a 2-nitro-4-ethoxycarbonyl-5-n-hexadecyloxyphenyl group, a 2-nitro-4-diethylcarbamoyl-5-n-hexadecyloxyphenyl group, a 2-nitro-4-cyano-5n-dodecylphenyl group, a 2,4-dinitrophenyl group, a 2-nitro-4-n-decylthiophenyl group, a 3,5-dinitrophenyl group, a 2-nitro-3,5-dimethyl-4-n-hexadecanesulfonyl group, a 4-methanesulfonyl-2-benzenesulfonylphenyl group, a 4-n-octanesulfonyl-2-methanesulfonylphenyl group, a 4-n-tetradecanesulfonyl-2-methanesulfonylphenyl group, a 4-n-hexanedecanesulfonyl-2-methanesulfonylphenyl group, a 2,5-didodecanesulfonyl-4-trifluoromethylphenyl group, a 4-n-decanesulfonyl-2-cyano-5-trifluoromethylphenyl group, a 4-cyano-2-methanesulfonylphenyl group, a 4-nitro-2-methanesulfonylphenyl group, a 4-nitro-2-n-dodecanesulfonylphenyl group, a 4-nitro-2-(2-sulfoethylsulfonyl)phenyl group, a 4-nitro-2-carboxymethylsulfonylphenyl group, a 4-nitro-2-carboxyphenyl group, a 4-nitro-2-ethoxycarbonyl-5-n-butoxyphenyl group, a 4-nitro-2-ethoxycarbonyl-5-n-hexadecyloxyphenyl group, a 4-nitro-2-diethylcarbamoyl-5-n-hexadecyloxyphenyl group, a 4-nitro-2-cyano-5-n-dodecylphenyl group, a 4-nitro-2-n-decyalthiophenyl group, a 4-nitro-3,5-dimethyl-2-n-hexadecanesulfonyl group, a 4-nitronaphthyl group, a 2,4-dinitronaphthyl group, a 4-nitro-2-n-octadecylcarbamoylnaphthyl group, a 4-nitro-2-dioctylcarbamoyl-5-(3-sulfobenzenesulfonylamino)naphthyl group, a 2,3,4,5,6-pentafluorophenyl group, a 2-nitro-4-benzoylphenyl group, a 2,4-diacetylphenyl group, a 2-nitro-4-trifluoromethylphenyl group, a 4-nitro-2-trifluoromethylphenyl group, a 4-nitro-3-trifluoromethylphenyl group, a 2,4,5-tricyanophenyl group, a 3,4-dicyanophenyl group, a 2-chloro-4,5-dicyanophenyl group, a 2-bromo-4,5-dicyanophenyl group, a 4-methanesulfonyl group, a 4-n-hexadecanesulfonylphenyl group, a 2-decanesulfonyl-5-trifluoromethylphenyl group, a 2-nitro-5-methylphenyl group, a 2-nitro-5-n-octadecyloxyphenyl group, a 2-nitro-4-N-(vinylsulfonylethyl)-N-methylsulfamoylphenyl group, and 2-methyl-6-nitrobenzoxazol-5-yl group.

Examples of the heterocyclic group shown by EAG are a 2-pyridyl group, a 3-pyridyl group, a 4-pyridyl group, a 5-nitro-2-pyridyl group, a 5-nitro-N-hexadecylcarbamoyl-2-pyridyl group, a 3,5-dicyano-2-pyridyl group, a 5-dodecanesulfonyl-2-pyridyl group, a 5-cyano-2-pyrazyl group, a 4-nitrothiophen-2-yl group, a 5-nitro-1,2-dimethylimidazol-4-yl group, a 3,5-diacetyl-2-pyridyl group, a 1-dodecyl-5-carbamoylpyridinium-2-yl group, a 5-nitro-2-furyl group, and a 5-nitrobenzthiazol-2-yl group.

Then, $(Time)_t$—PUG is explained in detail.

(Time) represents a group releasing PUG upon the cleavage of the sulfonyl group-nitrogen bond, the sulfonyl group-oxygen bond or the sulfonyl group-sulfur bond and the reaction following.

The groups show by (Time) are known and are described, for example, in Japanese Patent Application (OPI) Nos. 147244/86, pages 5 and 6, 236549/86, pages 8 to 14, and Japanese Patent Application No. 88625/86, pages 36 to 44.

Specific examples of preferred groups shown by (Time) are illustrated below, wherein (*) indicates the site of bonding to the dotted line side in formulae (I) and (II) described above and (*)(*) indicates the site of bonding to PUG.

When $R_1$ represents a simple bond, an oxygen atom, a nitrogen atom or a sulfur atom in (TIME) serves also as X.

(1)

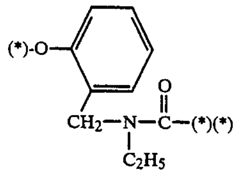

-continued (2)

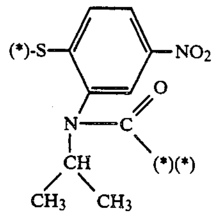

(3)

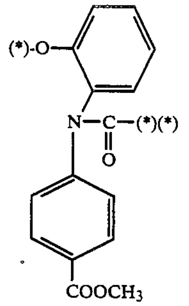

(4)

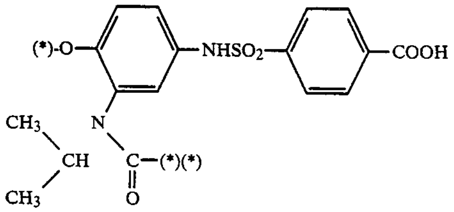

(5)

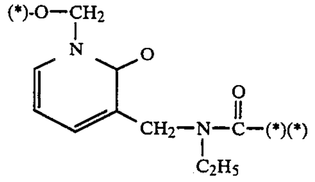

(6)

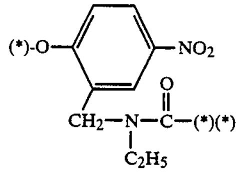

(7)

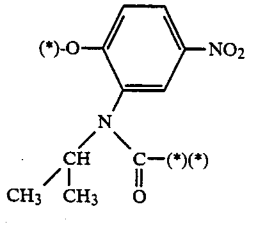

(8)

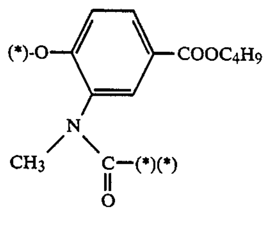

-continued
(9)
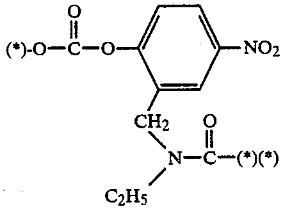
(10)
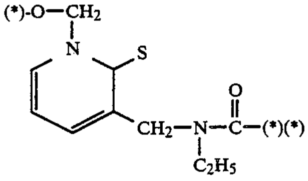
(11)
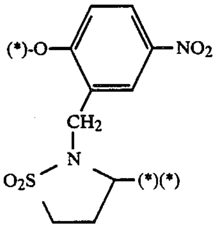
(12)
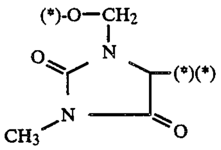
(13)
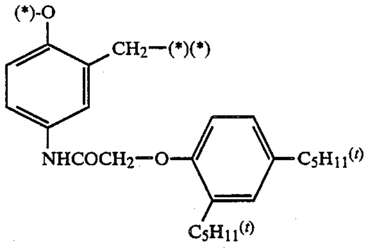
(14)
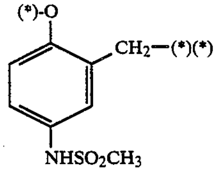
(15)
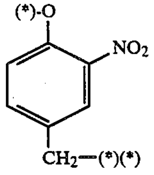
-continued
(16)
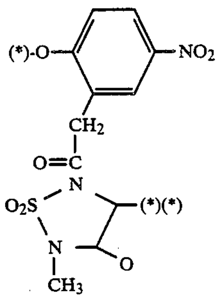
(17)
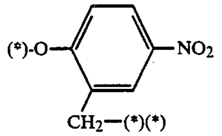
(18)
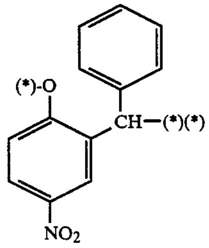
(19)
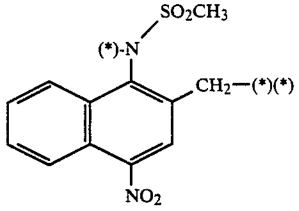
(20)
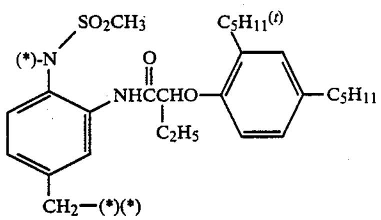
(21)
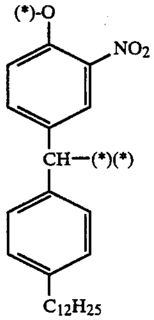
(22)
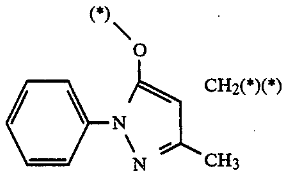

-continued
(23)
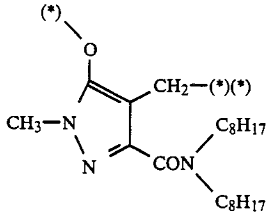
(24)
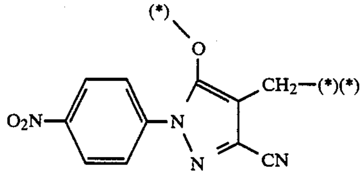
(25)
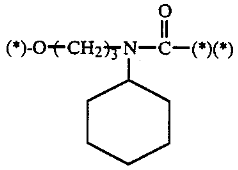
(26)
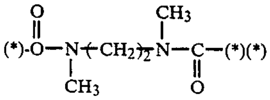
(27)
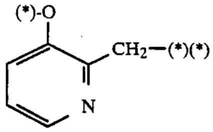
(28)
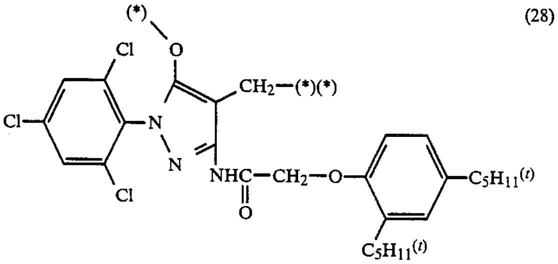
(29)
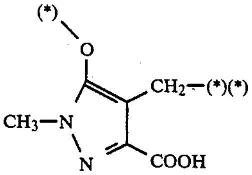
(30)
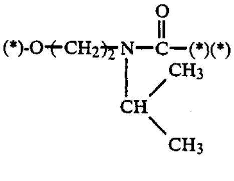
(31)
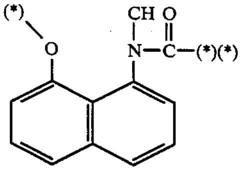
-continued
(32)
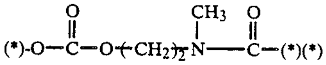
(*)-O—$CH_2$—(*)(*) (33)
(34)
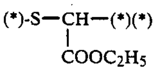
(35)
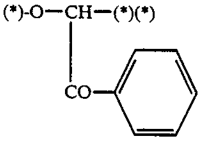
(36)
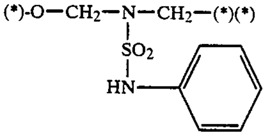
(37)
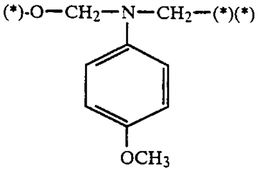
(38)
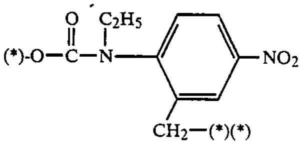
(39)
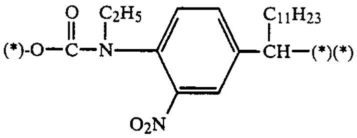
(40)
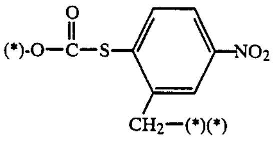
(41)
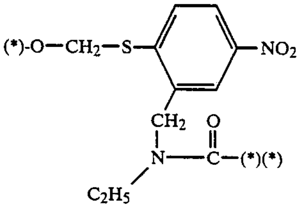

-continued (42)

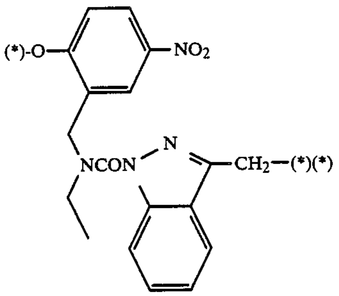

PUG represents a photographically useful group as Time-PUG or PUG. Examples of photographically useful groups are development inhibitors, development accelerators, nucleating agents, couplers, diffusible or non-diffusible dyes, desilvering accelerators, desilvering inhibitors, silver halide solvents, redox competing compounds, developing agents, auxiliary developing agents, fix accelerators, fix inhibitors, silver image stabilizers, toning agents, processing reliance improving agents, dot image improving agents, color image stabilizers, photographic dyes, surface active agents, hardening agents, desensitizers, contrast increasing agents, chelating agents, optical whitening agents, ultraviolet adsorbents, etc., and the precorsurs of them.

These photographic useful groups overlap each other in their useful properties and hence specific examples thereof are explained below.

When PUG is a development inhibitor, examples of the development inhibitor are compounds having a mercapto group bonded to a halogen atom (e.g., bromine, iodine, etc.) and a heterocyclic ring, such as substituted or unsubstituted mercaptoazoles (e.g., practically, 1-phenyl-5-mercaptotetrazole, 1-(4-carboxyphenyl)-5-mercaptotetrazole, 1-(3-hydroxyphenyl)-5-mercaptotetrazole, 1-(4-sulfophenyl)-5-mercaptotetrazole, 1-(3-sulfophenyl)-5-mercaptotetrazole, 1-(4-sulfamoylphenyl)-5-mercaptotetrazole, 1-(3-hexanoylaminophenyl)-5-mercaptotetrazole, 1-ethyl-5-mercaptotetrazole, 1-(2-carboxyethyl)-5-mercaptotetrazole, 2-methylthio-5-mercapto-1,3,4-thiadiazole, 2-(2-carboxyethylthio)-5-mercapto-1,3,4-thiadiazole, 3-methyl-4-phenyl-5-mercapto-1,2,4-triazole, 2-(2-dimethylaminoethylthio)-5-mercapto-1,3,4-thiadiazole, 1-(4-n-hexylcarbamoylphenyl)-2-mercaptoimidazole, 3-acetylamino-4-methyl-5-mercapto-1,2,4-triazole, 2-mercaptobenzoxazole, 2-mercaptobenzimidazole, 2-mercaptobenzothiazole, 2-mercapto-6-nitro-1,3-benzoxazole, 1-(1-naphthyl)-5-mercaptotetrazole, 2-phenyl-5-mercapto-1,3,4-oxazole, 1-[3-(3-methylureido)phenyl]-5-mercaptotetrazole, 1-(4-nitrophenyl)-5-mercaptotetrazole, 5-(2-ethylhexanoylamino)-2-mercaptobenzimidazole, etc.), substituted or unsubstituted mercaptoazaindenes (e.g., 6-methyl-4-mercapto-1,3,3a,7-tetraazaindene, 6-methyl-2-benzyl-4-mercapto-1,3,3a,7-tetraazaindene, 6-phenyl-4-mercaptotetraazaindene, 4,6-dimethyl-2-mercapto-1,3,3a,7-tetraazaindene, etc.), and substituted or unsubstituted mercaptopyrimidines (e.g., 2-mercaptopyrimidine, 2-mercapto-4-methyl-6-hydroxypyrimidine, 2-mercapto-4-propylpyrimidine, etc.).

Furthermore, heterocyclic compounds capable of forming imino silver are also used as the development inhibitor shown by PUG and examples of these compounds are substituted or unsubstituted benzotriazoles (e.g., benzotriazole, 5-nitrobenzotriazole, 5-methylbenzotriazole, 5,6-dichlorobenztriazole, 5-bromobenzortiazole, 5-methoxybenzotriazole, 5-acetylaminobenzotriazole, 5-n-butylbenzotrazole, 5-nitro-6-chlorobenzotriazole, 5,6-dimethylbenzotriazole, 4,5,6,7-tetrachlorobenzotriazole, etc.), substituted or unsubstituted indazoles (e.g., indazole, 5-nitroindazole, 3-nitroindazole, 3-chloro-5-nitroindazole, 3-cyanoindazole, 3-n-butylcarbamoylindazole, 5-nitro-3-methanesulfonylindazole, etc.,), and substituted or unsubstituted benzimidazoles (e.g., 5-nitrobenzimidazole, 4-nitrobenzimidazole, 5,6-dichlorobenzimidazole, 5-cyano-6-chlorobenzimidazole, 5-trifluoromethyl-6-chlorobenzimidazole, etc.).

Also, the development inhibitor shown by PUG may be a compound which becomes a compound having a development inhibiting property after being released from the oxidation reduction mother nucleus of formula (I) by a reaction subsequent to the oxidation reduction reaction in a development process and further changes into a compound having substantially no development inhibiting property or having greatly reduced development inhibiting property.

Practical examples of such a compound are 1-(3-phenoxycarbonylphenyl)-5-mercaptotetrazole, 1-(4-phenoxycarbonylphenyl)-5-mercaptotetrazole, 1-(3-maleinimidophenyl)-5-mercaptotetrazole, 5-(phenoxycarbonyl)benzotriazole, 5-(p-cyanophenoxycarbonyl)-benzotriazole, 2-phenoxycarbonylmethylthio-5-mercapto-1,3,4-thiadiazole, 5-nitro-3-phenoxycarbonylindazole, 5-phenoxycarbonyl-2-mercaptobenzimidazole, 5-(2,3-dichloropropyloxycarbonyl)benztriazole, 5-benzyloxycarbonylbenzotriazole, 5-(butylcarbamoylmethoxycarbonyl)benzotriazole, 5-(butoxycarbonylmethoxycarbonyl)benzotriazole, 1-(4-benzoyloxyphenyl)-5-mercaptotetrazole, 5-(2-methanesulfonylethoxycarbonyl)-2-mercaptobenzothiazole, 1-[4-(2-chloroethoxycarbonyl)phenyl]-2-mercaptoimidazole, 2-[3-thiophen-2-ylcarbonyl porpyl]thio-5-mercapto-1,3,4-thiadiazole, 5-cinnamoylaminobenzotriazole, 1-(3-vinylcarbonylphenyl)-5-mercaptotetrazole, 5-succinimidomethylbenzotriazole, 2-[4-succinimidophenyl]-5-mercapto-1,3,4-oxadiazole, 3-[4-(benzo-1,2-isothiazol-3-oxo-1,1-dioxy-2-yl)phenyl]-5-mercapto-4-methyl-1,2,4-triazole, and 6-phenoxycarbonyl-2-mercaptobenzoxazole.

When PUG is a diffusible or non-diffusible dye, examples of the dye are azo dyes, azomethine dyes, azopyrazolone dyes, indoaniline series dyes, indophenol series dyes, anthraquinone series dyes, triarylmethane series dyes, alizarine series dyes, nitro series dyes, quinoline series dyes, indigo series dyes, and phthalocyanine series dyes.

Also, there are leuco compounds of these dyes, the aforesaid dyes where the absorption wavelength is temporarily shifted, and dye precursors such as tetrazolium salts, etc.

Furthermore, these dyes may form chelating dyes with proper metals. These dyes are described, for example, in U.S. Pat. Nos. 3,880,658, 3,931,144, 3,932,380, 3,932,381, and 3,942,987.

The dyes and the dye precursors are preferably azo dyes, azomethine dyes, indoaniline dyes, and the dye precursors thereof in this invention.

Specific examples of the preferred dyes and dye precursors are illustrated below.

D-1
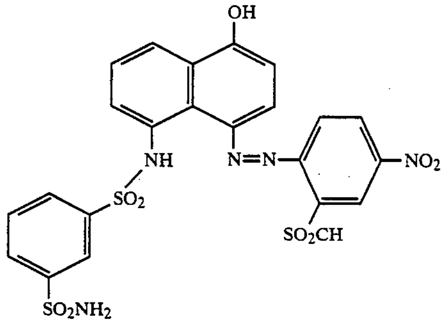
D-2
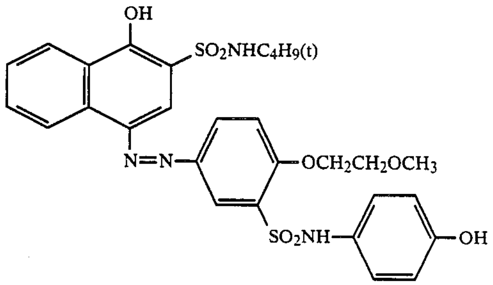
D-3
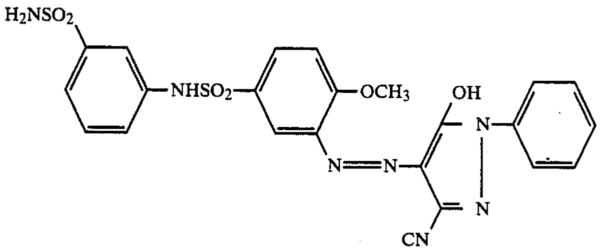
D-4
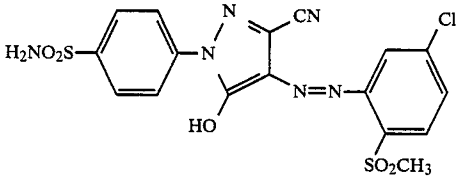
D-5
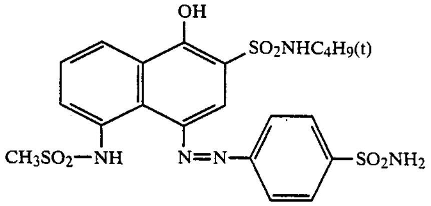
D-6
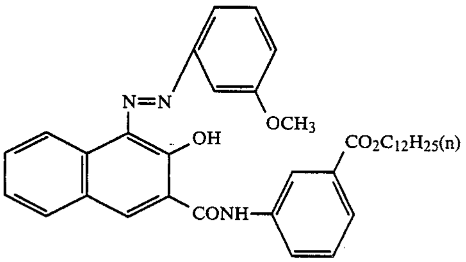
D-7
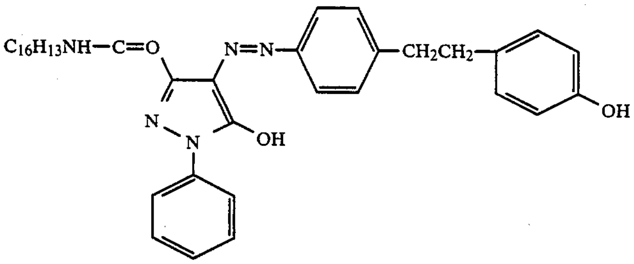
D-8
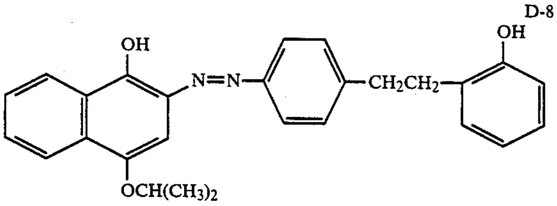
D-9
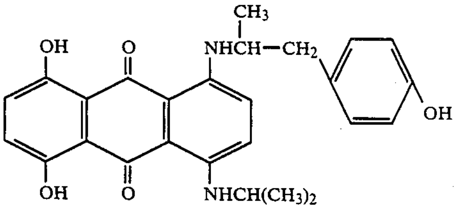

-continued
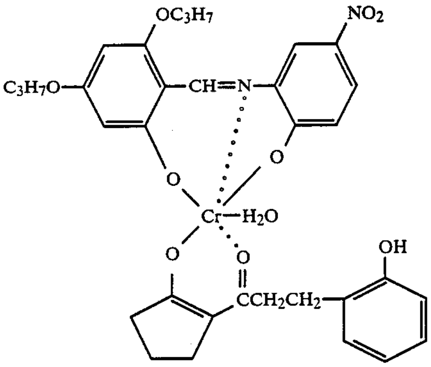
D-10
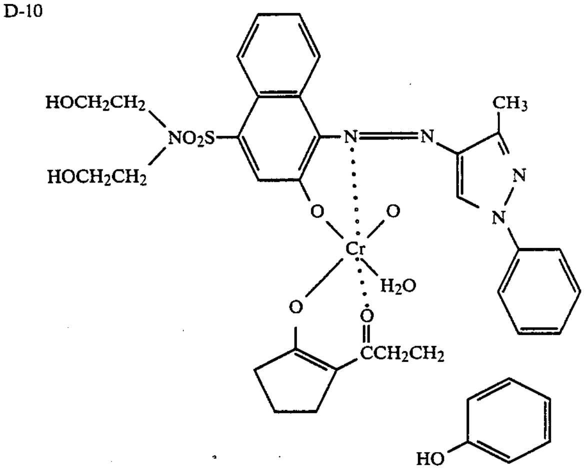
D-11
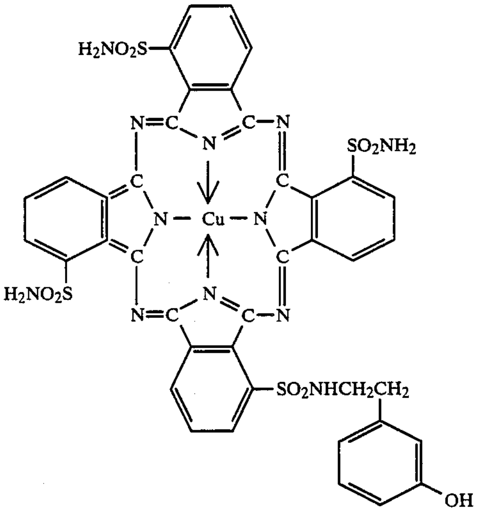
D-12
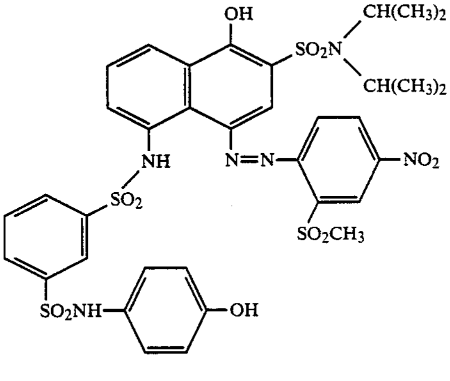
D-13
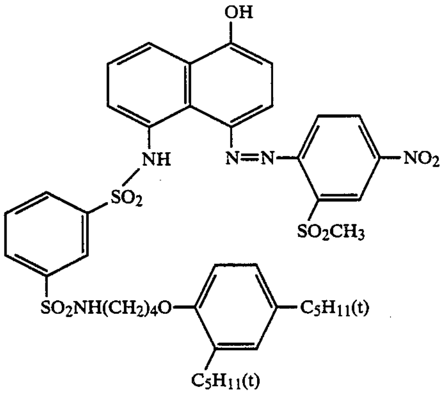
D-14
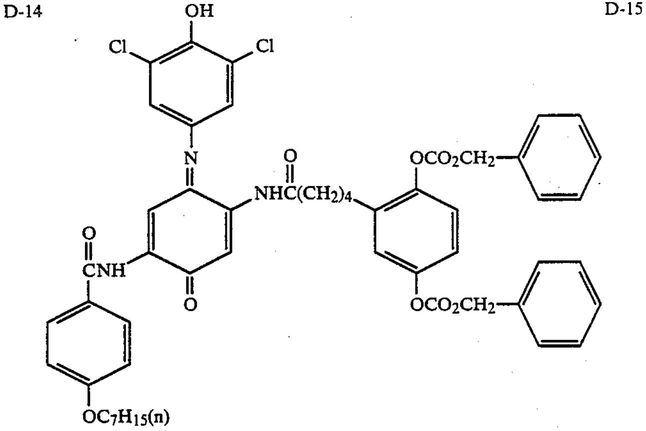
D-15
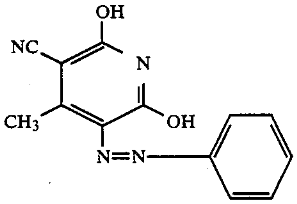
D-16
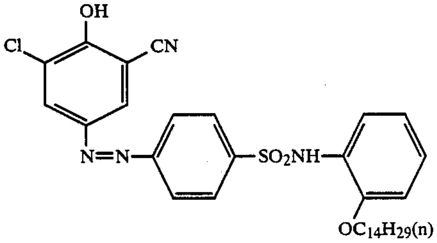
D-17

-continued
D-18
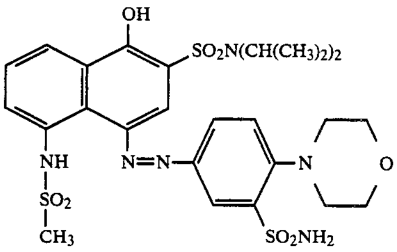
D-19
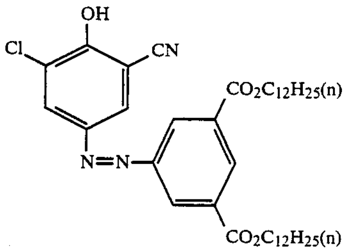
D-20
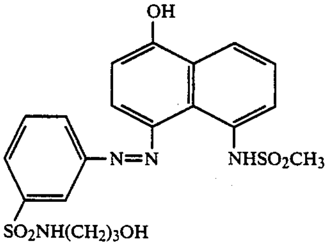
D-21
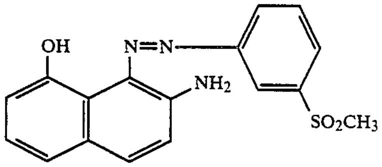
D-22
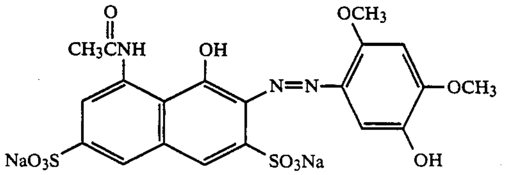
D-23
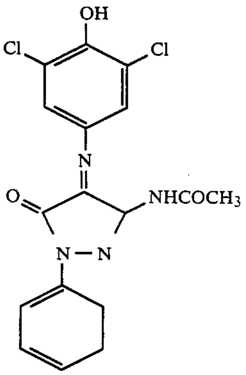
D-24
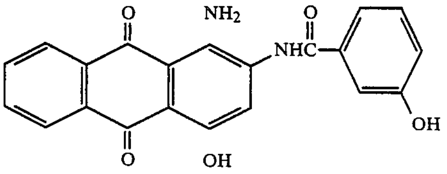
D-25
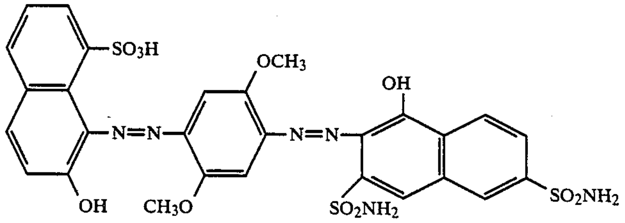
D-26
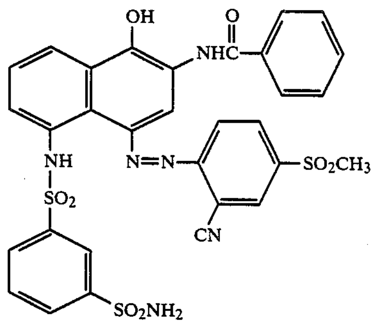
D-26
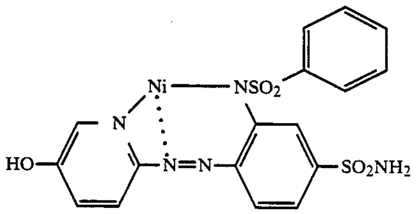

-continued
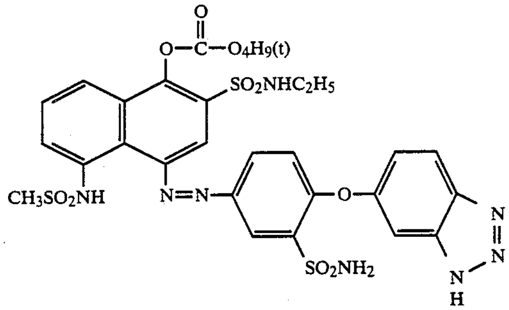
D-27
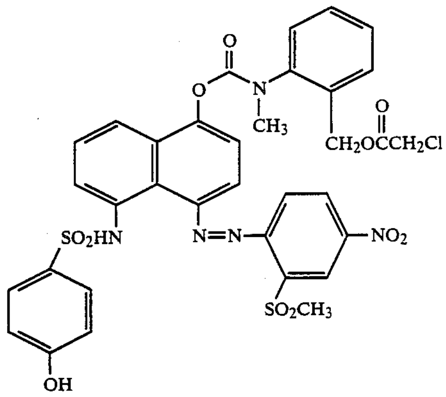
D-28
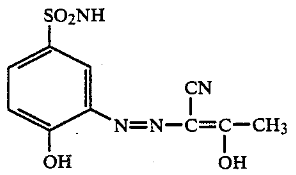
D-29
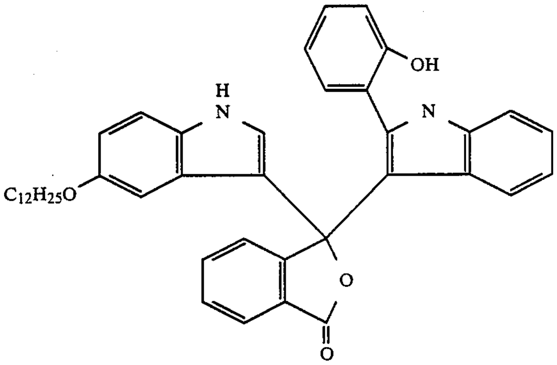
D-30
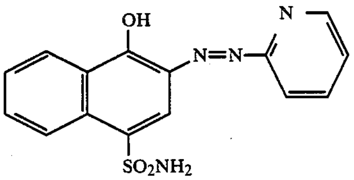
D-31
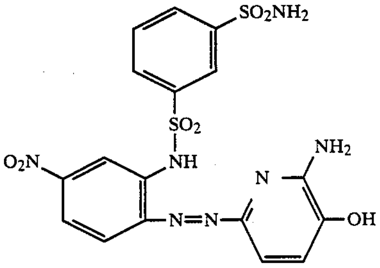
D-33
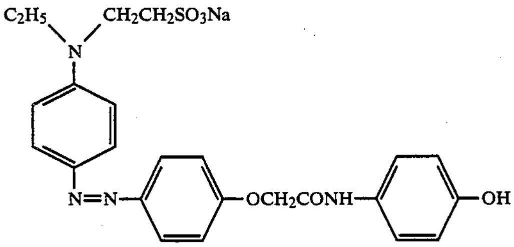
D-34
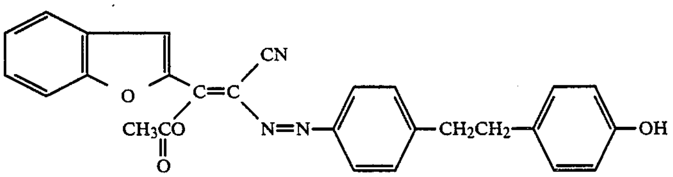
D-35

-continued
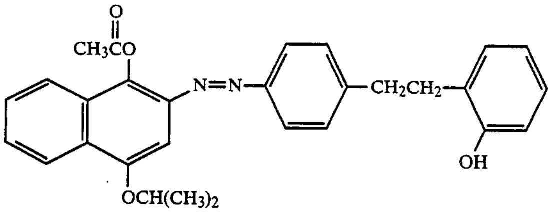
D-36
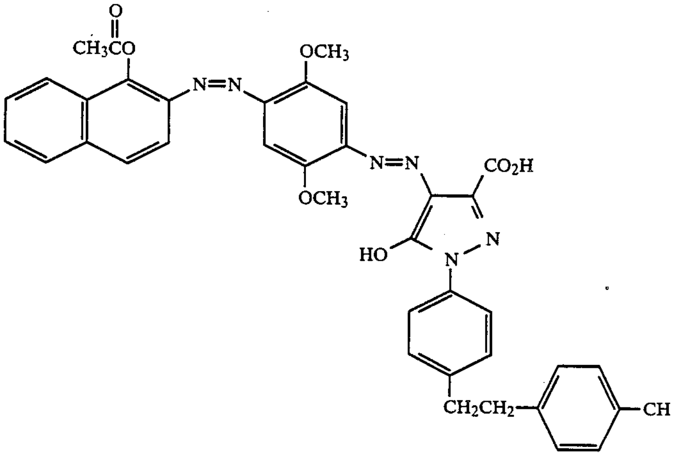
D-37
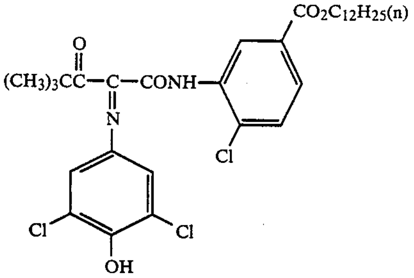
D-38
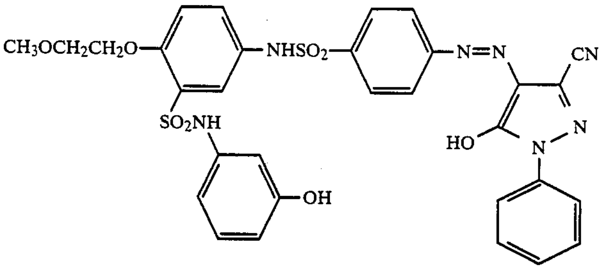
D-39
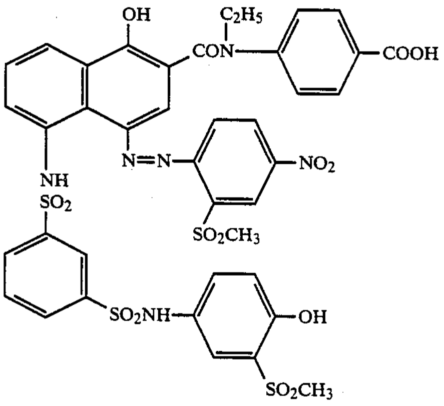
D-40
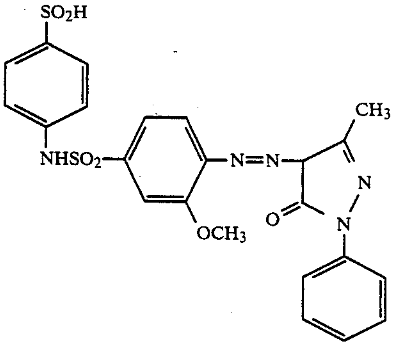
D-41

-continued

D-42

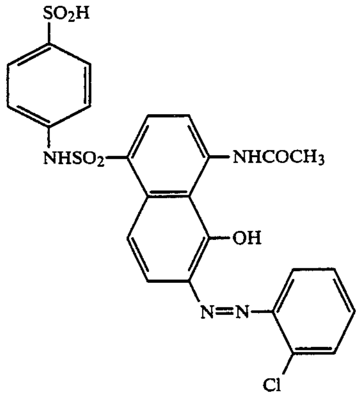

D-43

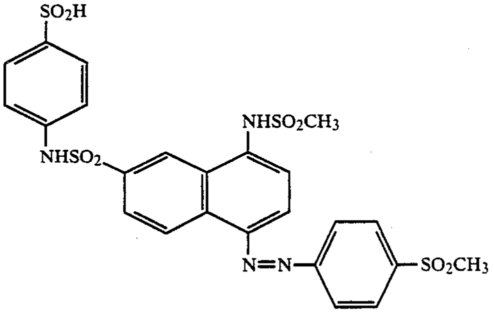

D-44

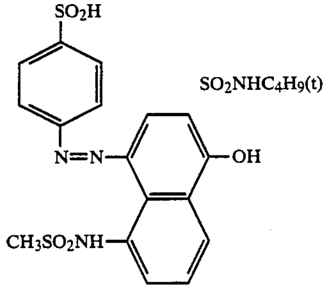

D-45

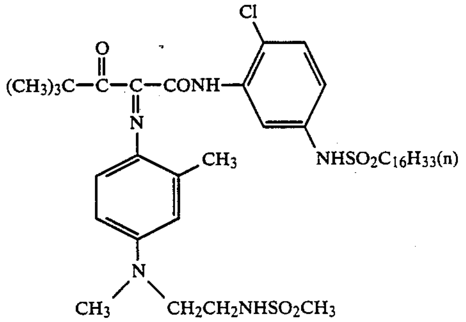

D-46

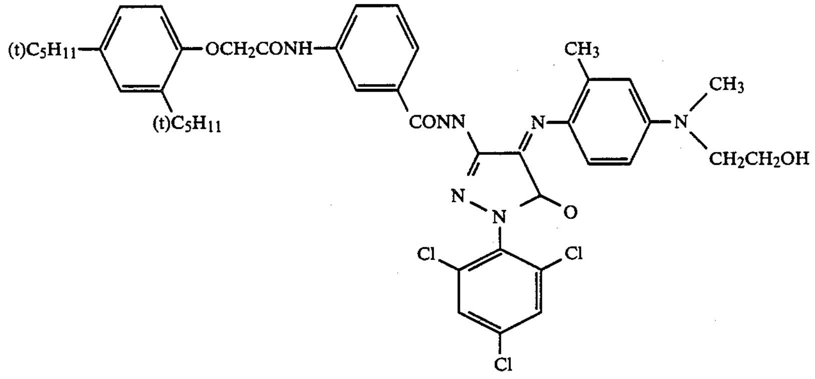

D-47

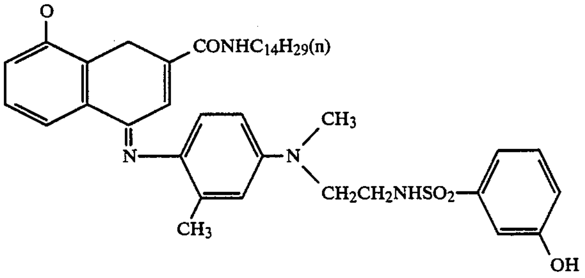

When PUG is a silver halide solvent, examples of the silver halide solvent are mesoion compounds described in Japanese patent application (OPI) No. 163042/85, U.S. Pat. Nos. 4,0003,910, 4,378,424, etc., mercaptoazoles or azolethiones having an amino group as a substituent described in Japanese patent application (OPI) No. 202531/82, etc., and, more practically, the compounds described in Japanese patent application No. 71768/85.

When PUG is a nucleating agent, examples of the nucleating agents are the moieties of the releasable groups being released from the couplers described in Japanese patent application (OPI) No. 170840/84.

For other photographically useful groups shown by PUG can, reference can be made to refer the description in Japanese patent application (OPI) No. 23013/86 and U.S. Pat. No. 4,248,962.

Then, specific examples of the compounds shown by formula (I) described above are illustrated below but the invention is not limited to these compounds.

When $R_1$ represents a simple bond and t represents 0, an oxygen atom, a nitrogen atom or a sulfur atom in PUG serves also as X.
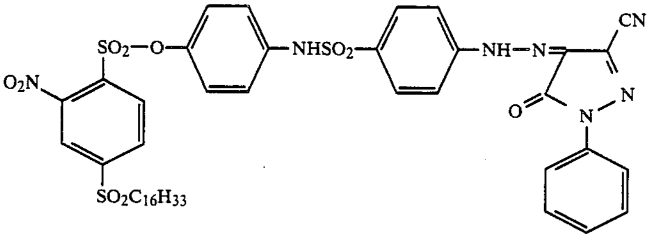
1.
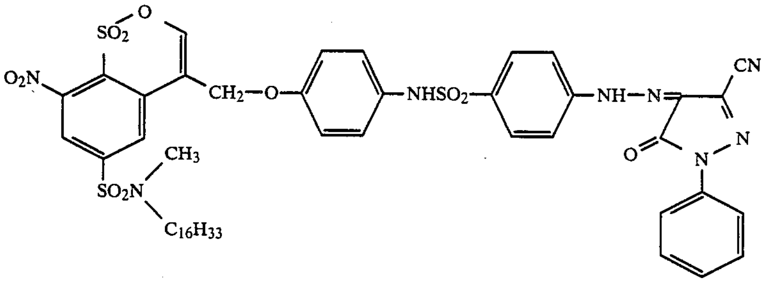
2.
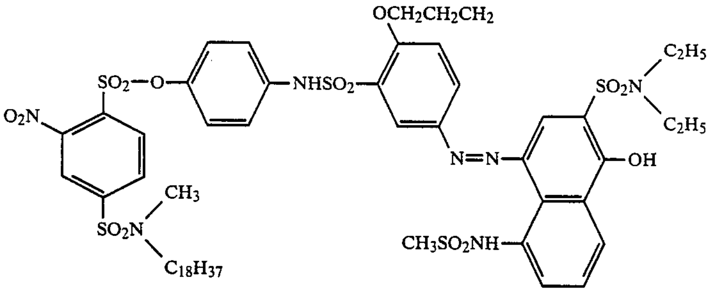
3.
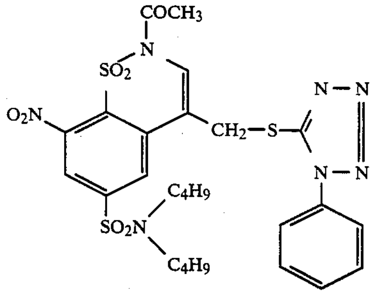
4.
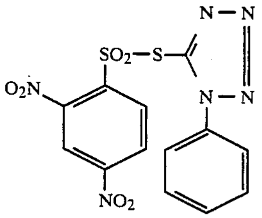
5.
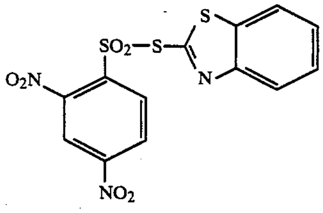
6.
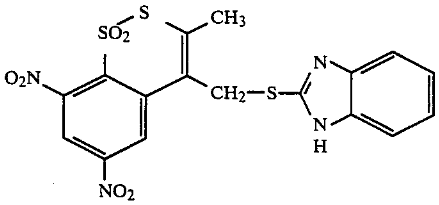
7.
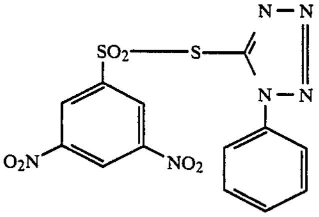
8.

-continued
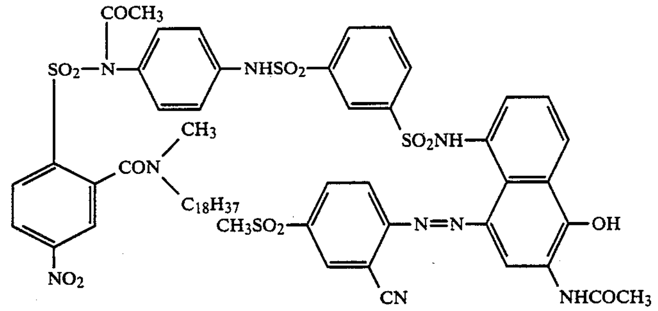
9.
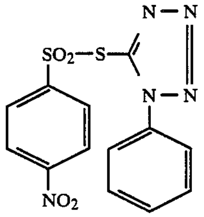
10.
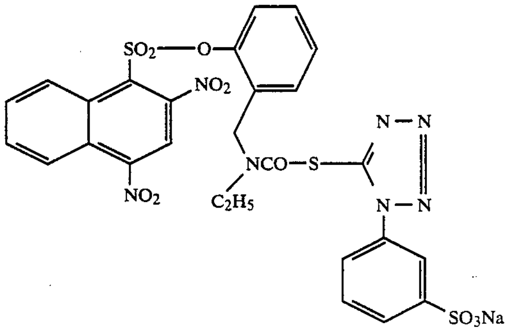
11.
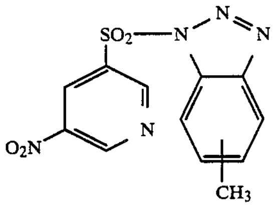
12.
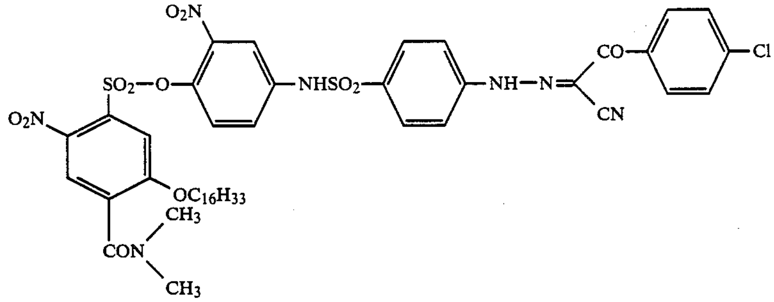
13.
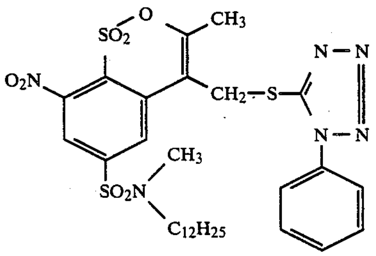
13.
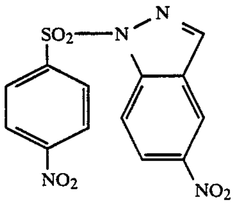
14.

-continued
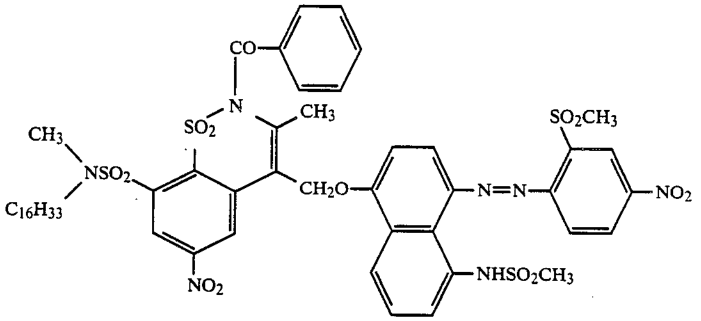
15.
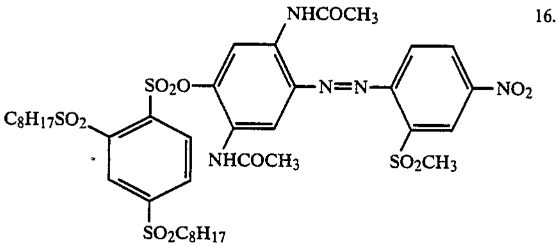
16.
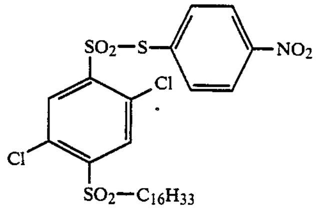
17.
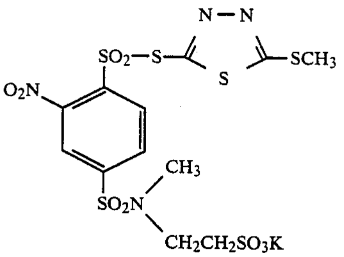
18.
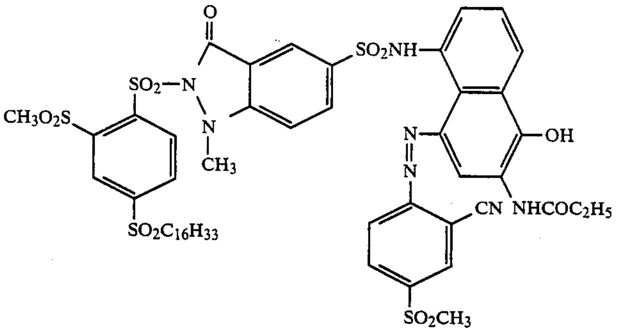
19.
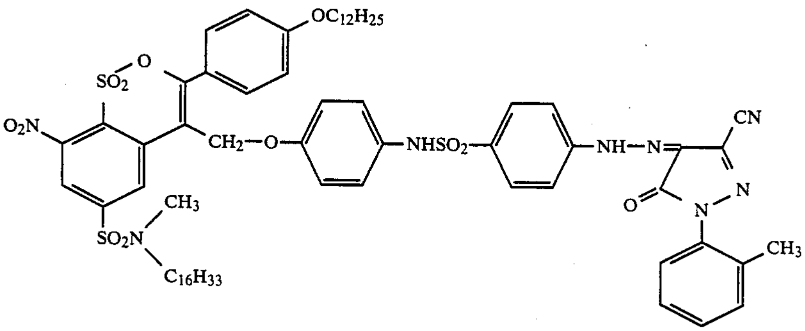
20.

-continued
21.
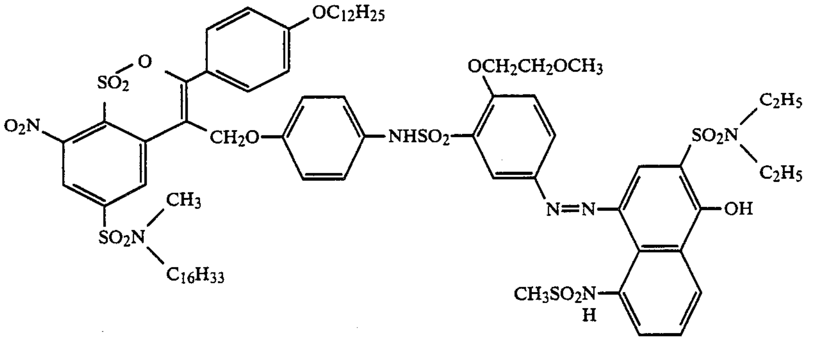
22.
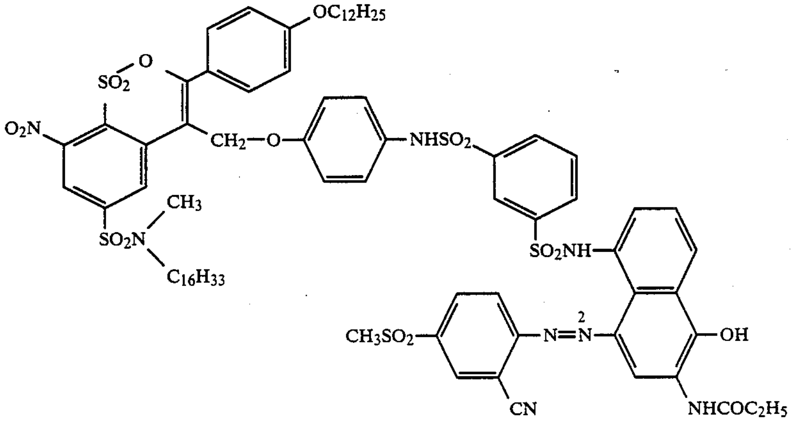
23.
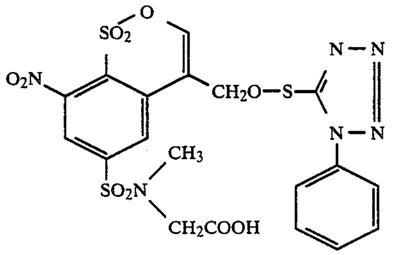
24.
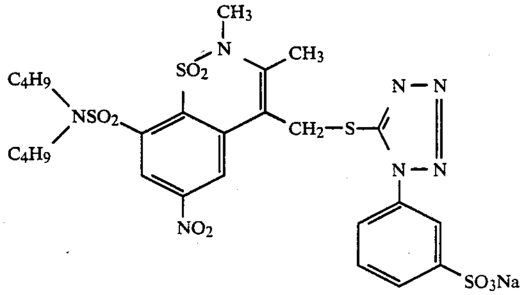
25.
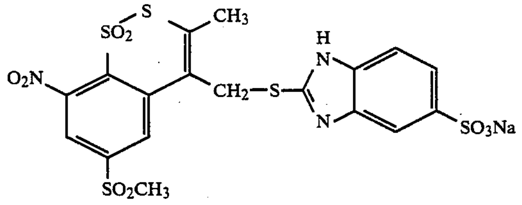
26.
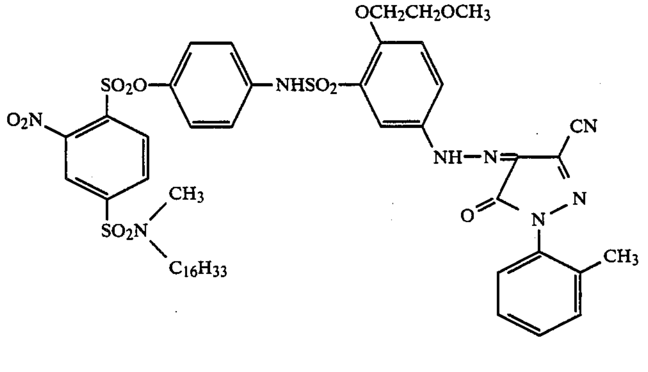

-continued
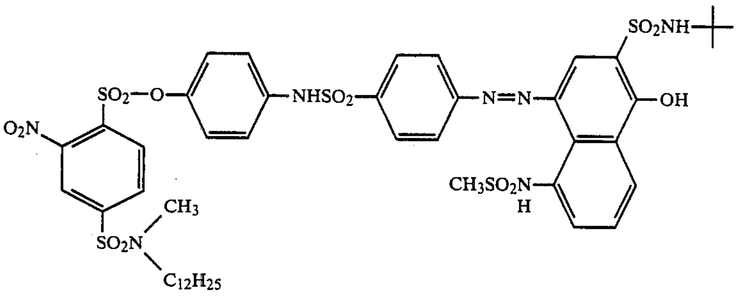
27.
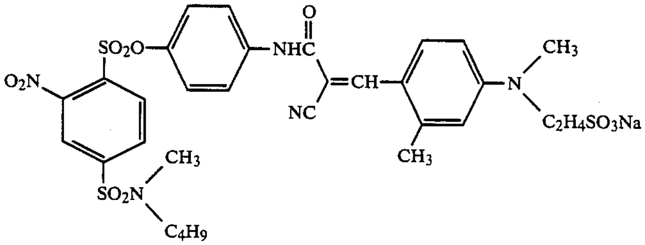
28.
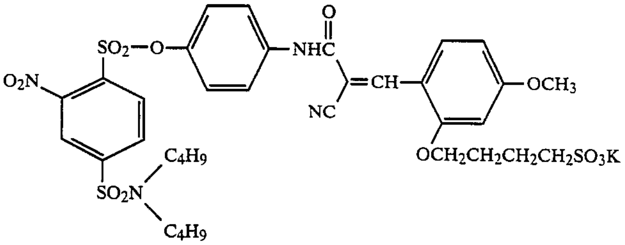
29.
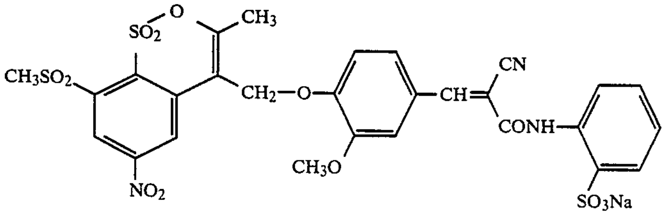
30.
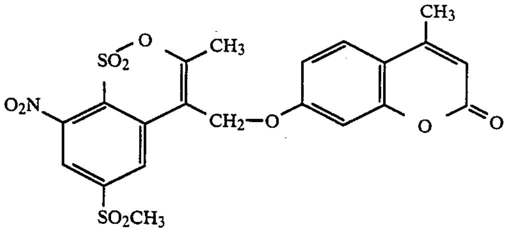
31.
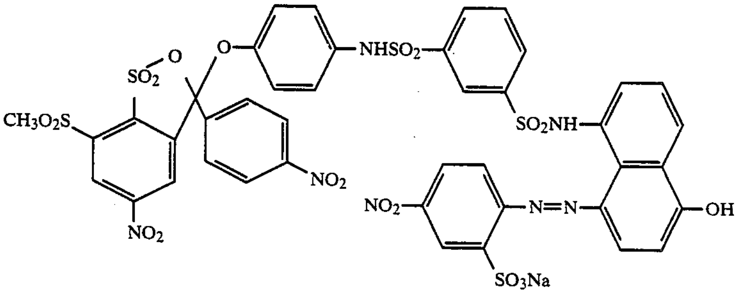
32.

-continued

33.

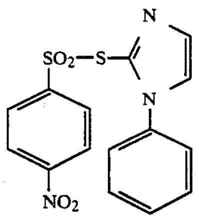

34.

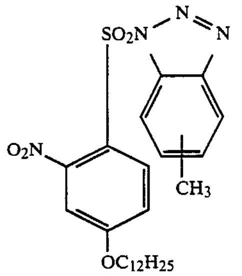

35.

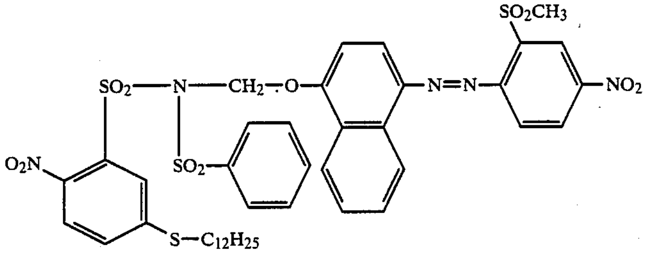

36.

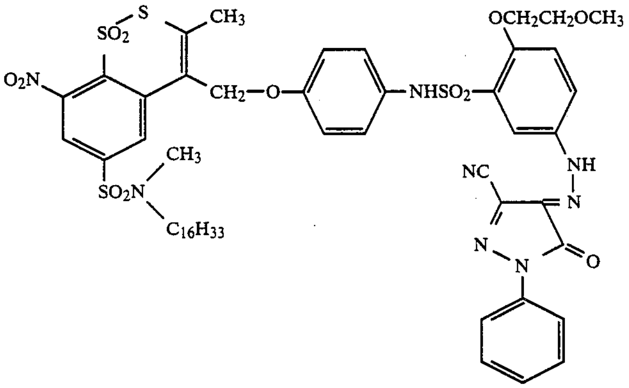

The compound of formula (I) for use in this invention can be easily synthesized by reacting an electron accepting arylsulfonyl halide or heteroarylsulfonyl halide and the reactive group (amino group, hydroxy group or mercapto group) of a photographically useful group in the presence of a base. Practical examples thereof are explained below.

SYNTHESIS EXAMPLE 1

Synthesis of 1-phenyl-5-(2,4-dinitrophenylsulfonylthio)tetrazole

In 100 ml of tetrahydrofuran were dissolved 10 g of 2,4-dinitrophenylsulfonyl chloride and 7.3 g of 1-phenyl-5-mercaptotetrazole and the solution obtiained was cooled to 0° C. Then, 4.1 g of triethylamine was gradually added to the solution. After one hour, the solvent was distilled off and the residue was crsytallized from a mixture of acetonitrile to provide 6.2 g of the desired product having a melting point of from 128° C. to 130° C.

SYNTHEIS EXAMPLE 2

Synthesis of 1-phenyl-5-(4-nitrophenylsulfonylthio)tetrazole

In 100 ml of acetonitrile were dissolved 10 g of 4-nitrophenylsulfonyl chloride and 8.8 g of 1-phenyl-5-mercpatotetrazole and the solution was cooled to 0° C. Then, 5.0 g of triethylamine was gradually added dropwise to the solution. After one hour since triethylamine was added dropwise to the reaction mixture and the product was crystallized from a mixture of acetonitrile and water to provide 7.1 g of the desired product having a melting point of from 128° C. to 130° C.

SYNTHESIS EXAMPLE 3

Synthesis of 5-nitro-1-(4-nitrophenylsulfonyl)indazole

In 100 ml of acetonitrile were dissolved 10 g of 4-nitrophenylsulfonyl chloride and 8.8 g of 5-nitroindazole and the solution was cooled to 0° C. Then, 6.8 g of triethylamine was gradually added dropwise to the solution and the mixture was allowed to stand overnight to precipitate crystals. Then, 50 ml of water was added dropwise to the system and the crystals formed were collected by filtration, washed with water and then ethyl acetate, and dried to provide 12.1 g of the desired product having a melting point of from 196° C. to 197° C.

The compound of formula (I) for use in this invention quickly and efficiently release a photographically useful group with good timing and reverse imagewise (i.e., reversely corresponding to the development of silver halide). Hence very wise uses of such a compound can be considered. For example, the following examples can be shown for applying the aforesaid function.

(1) When the photographically useful group in the compound of formula (I) for use in this invention is a diffusible dye, a color image can be formed by a diffusion transfer process or a transfer process by sublimation. In this case, a negative working silver halide emulsion gives a positive image and an autopositive silver halide emulsion gives a negative image.

(2) When the photographically useful group in the compound of formula (I) for use in this invention is a compound which is a colorless compound or a dye changing the absorption wavelength when bonded but is colored or discolored after being released, the color thereof can be changed before and after release. Accordingly, by utilizing this phenomenon, images can be formed.

(3) When the photographically useful group in the compound of formula (I) for use in this invention is an antifoggant, a large amount of the antifoggant is released in the non-image portions as compared to the image portions and hence the formation of fog can be effectively prevented without causing undesirable reduction in sensitivity. In this case, the same effect can be obtained for autopositive emulsion and negative working emulsion.

As described above, the compounds for use in this invention can be used for various purposes. Furthermore, the aforesaid compounds have the following excellent performances as compared to conventionally known compounds having similar functions.

(1) Since the compound for use in this invention can release a photographically useful group at a sufficiently high speed even at a temperature below −20° C. and also scarcely causes decomposition at high temperatures, the compound can be used in a very wide temperature range. Also, since in regard to pH, the cleavage of the $SO_2$—X bond can be directly combined with the release of a photographically useful group, the reduction becomes a velocity controlling step and the compound can be used in almost the entire pH range enabling the reduction reaction. Considering the practicability of photography, the temperature range is preferably from −20° C. to 180° C. and the pH range is preferably from 6.0 to 14.0.

(2) Since compound of formula (I) for use in this invention is an antioxidative, the photographic light-sensitive materials containing the compound are completely stable under the oxdiative atmosphere of air during the storage thereof. Also, since the $SO_2$—X single bond is stable to acid or alkali, the stability of the light-sensitive materials containing the compound during storage is very excellent.

(3) Furthermore, the compound for use in this invention is also excellent in the following points. That is, the compound formed by the reduction of a compound at processing, i.e., the decomposition product by reduction of the compound of this invention, is chemically inactive, gives no undesirable side reaction at processing, and also gives no influences on the storage of the photograph, such as the stability of images formed, etc.

The compound of formula (I) for use in this invention is added to a silver halide emulsion layer and/or a hydrophilic colloid layer formed on or under the silver halide emulsion layer for attaining the desired object. In the case of using the compound of formula (I) in this invention, it is required to select a suitable PUG according to each purpose and the addition amount thereof differs according to the kind of the photographic light-sensitive material and the nature of the PUG selected. In general, the addition amount thereof is preferably in the range of from $1\times10^{-7}$ to $1\times10^{3}$ mol per mol of silver halide.

The compound for use in this invention can be used in an amount of a wide range and a preferred amount thereof depends upon the kind of PUG. For example, when PUG is a diffusible dye, the amount of the compound depends upon the extinction coefficient of the dye but is from 0.05 millimol/$m^2$ to 50 millimols/$m^2$, and preferably from 0.1 millimol/$m^2$ to 5 millimols/$m^2$. When PUG is a development inhibitor, the amount of the compound is from $1\times10^{-7}$ mol to $1\times10^{-1}$ mol, and preferably from $1\times10^{-3}$ mol to $1\times10^{-2}$ mol per mol of silver halide. Also, when PUG is a development accelerator or a nucleating agent, the amount is preferably in the range described above for the development inhibitor. When PUG is a silver halide solvent, the compound is preferably used in the range of from $1\times10^{-5}$ mol to $1\times10^{3}$ mol, and more preferably in the range of from $1\times10^{-4}$ to $1\times10^{1}$ mol per mol of silver halide.

The compound of formula (I) for use in this invention releases a photographically useful group or the precursor therefor by accepting an electron from a reducing material. Accordingly, if the reducing material capable of uniformly releasing a photographically useful group over the whole images is imagewise changed into an oxidized product, the photographically useful group or the precursor thereof can be reverse imagewise released.

The reducing materials used for the reduction of the compounds for use in this invention can be inorganic compounds or organic compounds, and their oxdiation potential is preferably lower than the standard oxidation-reduction potential of silver ion/silver, which is 0.80 V.

Examples of usable inorganic compounds include metals having an oxidation potential of 0.80 V or less, such as Mn, Ti, Si, Zn, Cr, Fe, Co, Mo, Sn, Pb, W, $H_2$, Sb, Cu and Hg; ions and complexes thereof having an oxidation potential of 0.80 V or less, such as $Cr^{2+}$, $V^{2+}$, $Cu^{+}$, $Fe^{2+}$, $MnO_4^{2-}$, $I^-$, $Co(CN)_6^{4-}$, $Fe(CN)_6^{4-}$, $Fe(EDTA)^{2-}$, etc.; metal hydrides having an oxidation potential of 0.80 V or less, such as NaH, LiH, KH, $NaBH_4$, $LiBH_4$, $LiAl(O—tC_4H_9)_3H$, $LiAl(OCH_3)_3H$, etc.; sulfur or phosphorous compounds having an oxidation potential of 0.80 V or less, such as $Na_2SO_3$, NaHS, $NaHSO_3$, $H_3P$, $H_2S$, $Na_2S$, $Na_2S_2$, etc.

The organic reducing compounds which are usable include, for example, organic nitrogen compounds such as alkylamines and arylamines, organic sulfur compounds such as alkylmercaptans and arylmercaptans and organic phosphorous compounds such as alkylphosphines and arylphosphines, and in particular, reducing compounds for silver halide which follow the Kendal-Pelz theory disclosed in James, *The Theory of the Photographic Process* 4th edition (1977) page 299, are preferred.

Particularly preferred reducing agent are as follows.

3-Pyrazolidones and precursors thereof, such as 1-phenyl-3-pyrazolidone, 1-phenyl-, 4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone, 1,5-diphenyl-3-pyrazolidone, 1-phenyl-4-methyl-4-stearoyloxymethyl-3-pyrazolidone, 1-phenyl-4-methyl-4-lauroyloxymethyl-3-pyrazolidone, 1-phenyl-4,4-bis(lauroyloxymethyl)-3-pyrazolidone, 1-phenyl-2-acetyl-3-pyrazolidone, and 1-phenyl-3-acetoxypyrazolidone.

Hydroquinones and precursors thereof, such as hydroquinone, toluhydroquinone, 2,6-dimethylhydroquinone, t-butylhydroquinone, 2,5-di-t-butylhydroquinone, t-octylhydroquinone, 2,5-di-t-octylhydroquinone, pentadecylhydroquinone, sodium 5-pentadecylhydroquinone-2-sulfonate, p-benzoyloxyphenol, 2-methyl-4-benzoyloxyphenol, and 2-t-butyl-4-(4-chlorobenzoyloxy)-phenol.

Color developing agents can be also used as other reducing materials in this invention, including p-phenylene type color developing agents as described in U.S. Pat. No. 3,531,286. Among them, N,N-diethyl-3-methyl-p-phenylenediamine is typical. Other useful reducing agents include aminophenols as described in U.S. Pat. No. 3,761,270. In the aminophenol reducing agents, particularly useful compounds are 4-amino-2,6-dichlorophenol, 4-amino-2,6-dibromophenol, 4-amino-2-methylphenol sulfate, 4-amino-3-methylphenol sulfate, 4-amino-2,6-dichlorophenol hydrochloride. Furthermore, *Research Disclosure,* Vol. 151, No. 15108 (November, 1976) and U.S. Pat. No. 4,021,240 describe 2,6-dichloro-4-substituted sulfonamidophenols and 2,6-dibromo-4-substituted sulfonamidophenols, and Japanese patent application (OPI) No. 16740/84 describes p-(N,N-dialkylaminophenyl)sulfamines; and these compounds are usable in this invention. In addition to the aforesaid phenol-type reducing agents, naphthol-type reducing agents such as 4-aminonaphthol derivatives and 4-substituted sulfonamidonaphthol derivatives as described in *Research Disclosure,* Vol. 178, No. 17842 (February 1979) and Japanese patent application (OPI) No. 88136/81 and Japanese patent application No. 100380/85 are particularly useful. Furthermore, general color developing agents can be also used in this invention and examples thereof are aminohydroxypyrazole derivatives described in U.S. Pat. No. 2,895,825, aminopyrazoline derivatives described in U.S. Pat. No. 2,892,714, and hydrazone derivatives described in *Research Disclosure,* Vol. 194, No. 19412 (June, 1980), pp 227-230, and ibid., Vol. 194, No. 19415 (June 1980), pp. 236-240. These color developing agents may be used singly or as a combination of two or more thereof.

In the case of incorporating the non-diffusible reducing material in the photographic light-sensitive materials, it is preferred to use the reducing material as a combination with an electron transferring agent (ETA) for accelerating the electron transfer between the reducing material and a developable silver halide emulsion.

The electron transferring agent (ETA) can be selected from the aforesaid reducing materials. In order that the electron transferring agent (ETA) has a more preferred action, it is preferred that the mobility thereof is larger than that of the immobile reducing material.

As the reducing material which is used as a combination with ETA, any of the reducing agents described above, which do not substantially move in the layers of the light-sensitive material can be used but hydroquinones, aminphenols, aminonaphthols, 3-pyrqzolidinones, saccharin and the precursors thereof, picoliniums, the compounds described in Japanese patent application (OPI) No. 110827/78 as electron donative materials, etc., are particularly preferred.

Then, specific examples thereof are illustrated below.

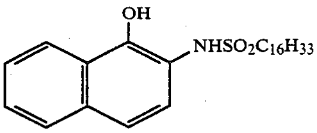
S-1

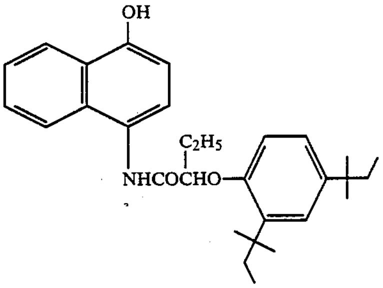
S-2

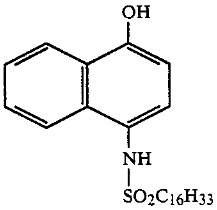
S-3

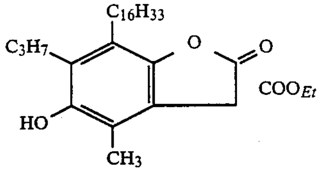
S-4

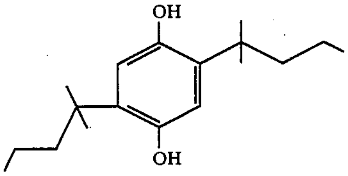
S-5

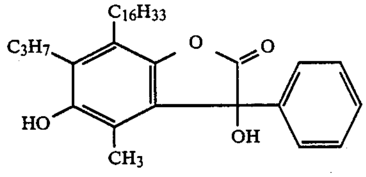
S-6

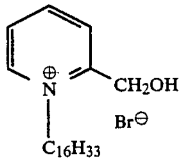
S-7

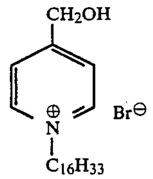
S-8

-continued
S-9
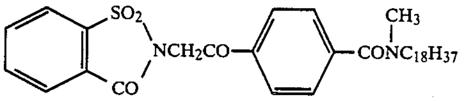
S-10
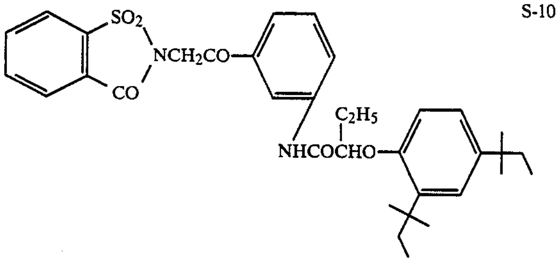
S-11
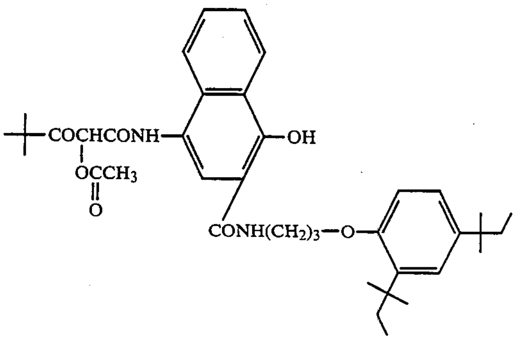
S-12
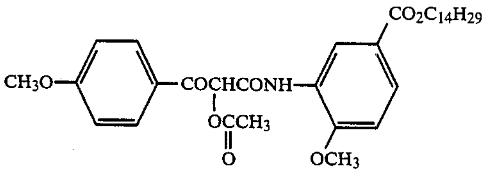
S-13
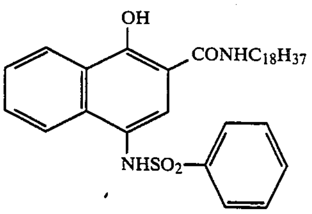
S-14
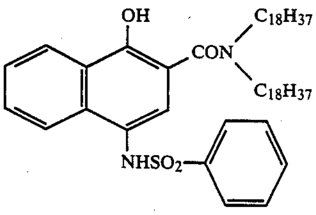
S-15
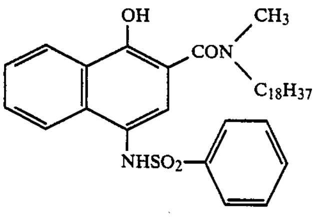
-continued
S-16
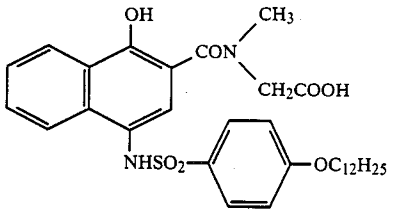
S-17
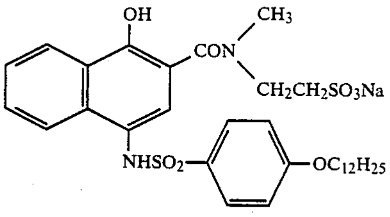
S-18
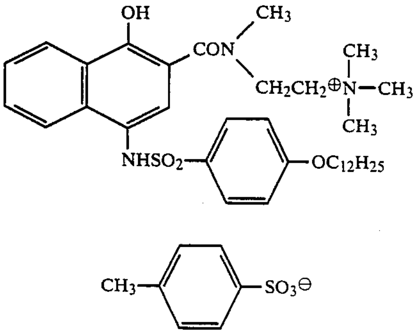
S-19
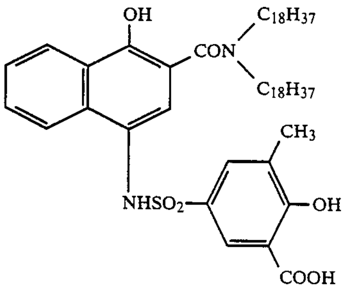
S-20
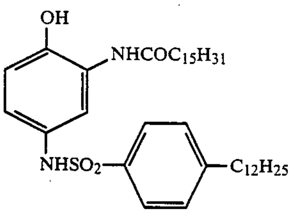
S-21
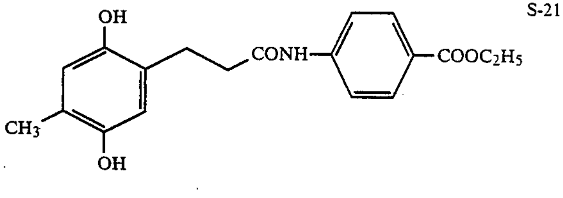
S-22
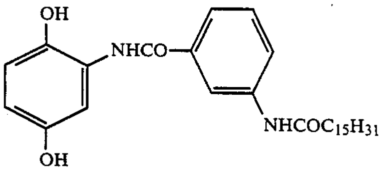

-continued
S-23
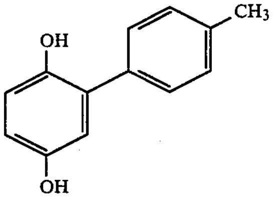
S-24
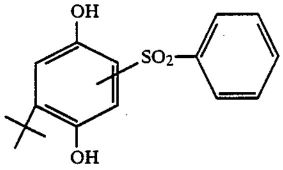
S-25
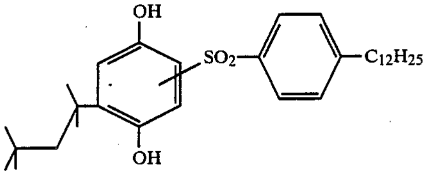
S-26
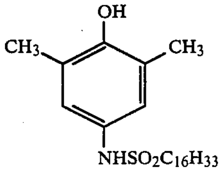
S-27
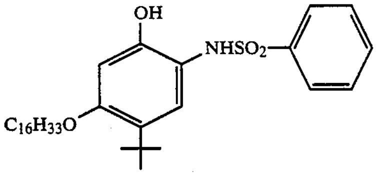
S-28
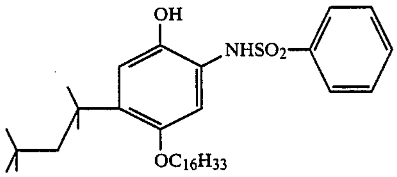
S-29
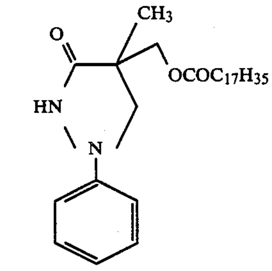
S-30
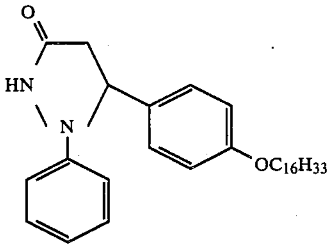
-continued
S-31
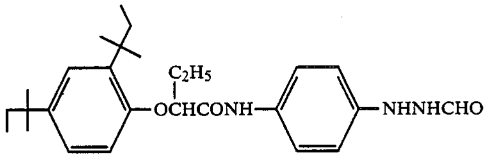
S-32
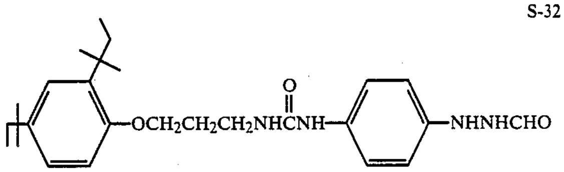
S-33
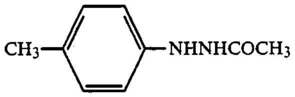
S-34
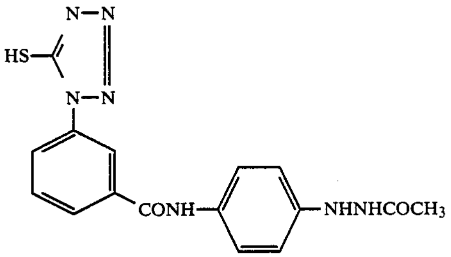
S-35
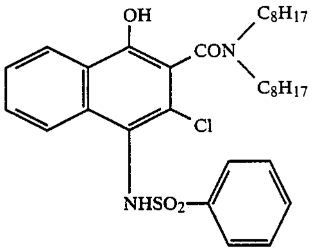
S-36
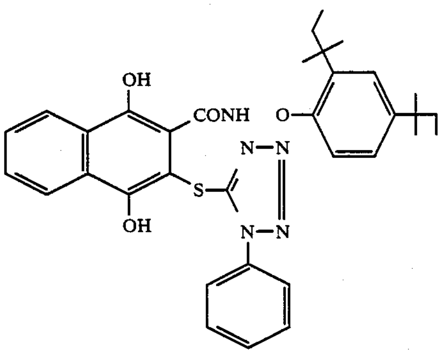

-continued
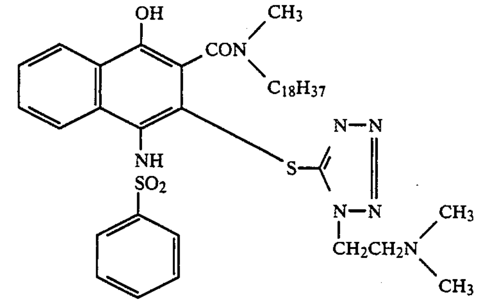
S-37
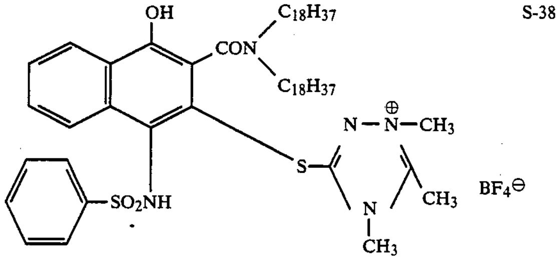
S-38
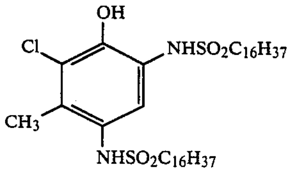
S-39
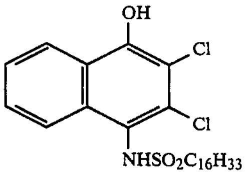
S-40
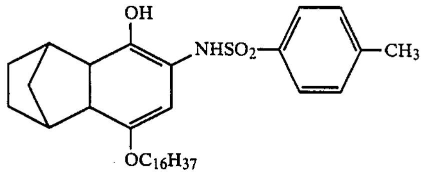
S-41
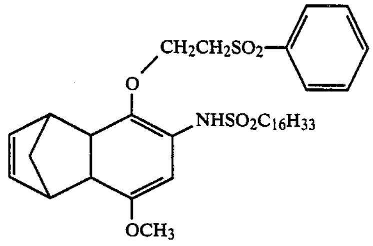
S-42
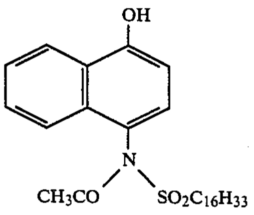
S-43
-continued
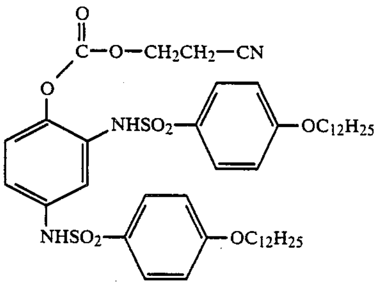
S-44
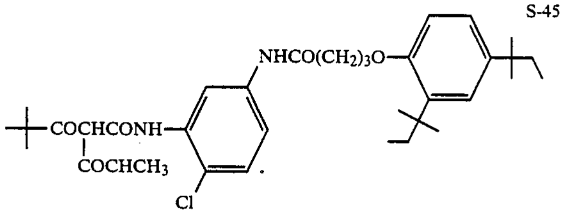
S-45
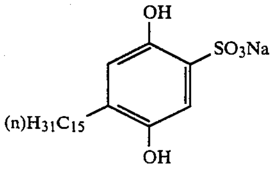
S-46
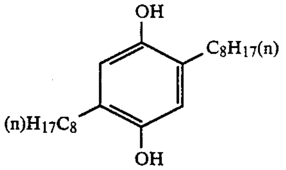
S-47
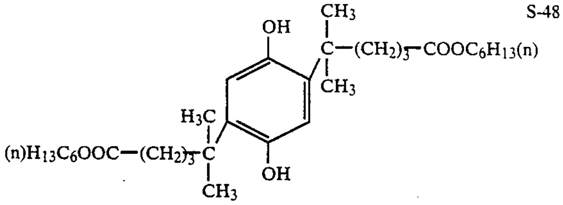
S-48
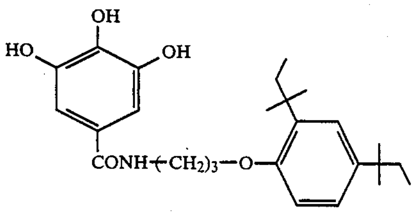
S-49
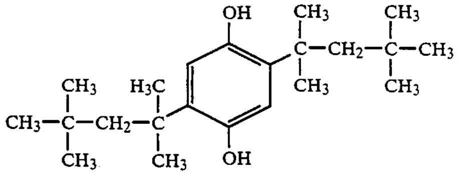
S-50

-continued

S-51

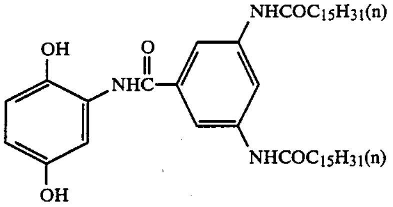

S-52

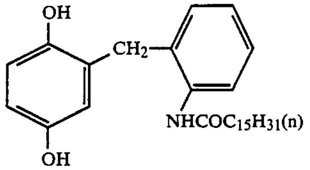

S-53

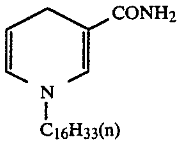

ETA's usable in combination with the reducing materials may be any ETA which may be cross-oxidized with said material. Preferred examples thereof are diffusible 3-pyrazolidinones, aminophenols, phenylenediamines and reductones.

The light-sensitive materials of this invention can be used as so-called conventional light-sensitive materials which are developed using a developer at about normal temperature and also as heat-developable light-sensitive materials.

In the case where the compounds of this invention are applied to conventional silver halide photographic materials, two systems are preferred for the reaction of the aforesaid reducing material or the combination of the aforesaid reducing material and ETA with the photographic light-sensitive material. In one system, the reducing material or the combination of the reducing material and ETA is applied to the photographic material in the form of a developer in the development thereof. In the other system, the reducing material is previously incorporated in the photographic material and the ETA is applied to the photographic material in the form of a developer. In the former system, the preferred amount to be used is 0.001 mol/liter to 1 mol/liter, which is the concentration of the material in the total developer solution. In the latter system of previously incorporating in the photographic material, 0.5 to 50 mols of the reducing material is previously incorporated in the photographic material per mol of the compound of this invention, and the concentration of ETA in the solution is preferably from 0.001 mol/liter to 1 mol/liter.

On the other hand, in case where the compounds of this invention are applied to a heat developable photographic material, the reducing material or the combination of the reducing material and ETA is preferably previously incorporated in the heat developable photographic material. In this case, the preferred amounts are from 0.01 to 50 mol of the reducing material and preferably 0.1 to 5 mol, per mol of the compound of this invention, and from 0.001 to 5 mol, and more preferably from 0.01 to 1.5 mol per mol of silver halide.

The silver halide which can be used in this invention may include any of silver chloride, silver bromide, silver iodide, silver chlorobromide, silver chloroiodide, silver iodobromide, and silverchloroiodo-bromide.

The halogen composition in the silver halide grains may be uniform, or the silver halide grains may have a multiple structure in which the composition is different between the surface portion and an inner portion (see Japanese patent application (OPI) Nos. 154232/82, 108533/83, 48755/84 and 52237/84, U.S. Pat. No. 4,433,048 and European Pat. No. 100,984).

Also, tabular grain silver halide emulsion containing grains having a thickness of 0.5 μm or less, a diameter of at least 0.6 μm and an average aspect ratio of at least 5 or more (see U.S. Pat. Nos. 4,414,310 and 4,435,499 and West German patent application (OLS) No. 3,241,646A1), and a monodispersed emulsion having a nearly uniform distribution of grain size (see Japanese patent application (OPI) Nos. 178235/82, 100846/83, and 14829/83, PCT Application (OPI) No. 83/02338A1, and European Pat. Nos. 64,412A3 and 83,377A1) may be used in this invention.

Two or more kinds of silver halides in which the crystal habit, halogen composition, grain size and/or distribution of grain size, etc., are different from each other may be used in mixture. Furthermore, two or more kinds of monodispersed emulsions having different grain size from each other may be employed in mixture to control gradation.

The average grain size of the silver halide used in this invention is preferably from 0.001 μm to 10 μm, and more preferably from 0.001 μm to 5 μm.

The silver halide emulsions can be prepared by any of an acid process, a neutral process, and an ammonia process. Furthermore, the reaction system of a soluble silver salt and a soluble halide may be any of a single jet process, a double jet process, and a combination thereof. In addition, a reverse mixing process in which silver halide grains are formed in the presence of an excess of silver ions, or a controlled double jet process in which the pAg in the liquid phase is kept constant, can also be utilized. Moreover, for increasing growth of the grains, the concentration of addition, the amount of the addition and/or the speed of the addition of the silver salt and halide added may be raised (see Japaense Patent Application (OPI) Nos. 142329/80 and 158124/80, and U.S. Pat. No. 3,650,757).

Furthermore, silver halide grains of the epitaxial junction type (see Japanese Patent Application (OPI) No. 16124/81 and U.S. Pat. No. 4,094,684) may be employed.

In the step for formation of the silver halide grains for use in this invention, ammonia, an organic thioether derivatives as described in Japanese Patent Publication No. 11386/72, or a compound containing sulfur as described in Japanese Patent Application (OPI) No. 144319/78, etc., can be used as a solvent for the silver halide.

In the process for the physical ripening of the silver halide grains, a cadmium salt, a zinc salt, a lead salt, or a thallium salt may coexist. These salts are used for the purpose of improving a change in the photographic performance against the pressure, etc. Furthermore, for the purpose of eliminating high-intensity reciprocity failure or low-intensity reciprocity failure, a water-soluble iridium salt such as iridium (III or IV) chloride, ammonium hexachloroiridate, etc., or a water-soluble rhodium salt such as rhodium chloride, etc., can be used.

Soluble salts may be removed from the silver halide emulsion after precipitate formation or physical ripening, and a noodle washing process or flucculation process can be used for the pupose.

While the silver halide emulsion may be employed as a primitive emultion, the silver halide emulsion is usually chemically sensitized. For the chemical sensitization, a sulfur sensitization method, a reduction sensitization method, and a noble metal sensitization method, which are known in the field of emulsions for conventional photographic light-sensitive materials, can be employed alone or in combiantion therewith. Such a chemical sensitization may be carried out in the presence of a nitrogen-containing heterocyclic compound (see Japanese Patent Application (OPI) Nos. 126526/83 and 215644/83).

The silver halide emulsion for use in this invention may be of a surface latent image type in which a latent image is mainly formed on the surface of the grains or of an internal latent image type in which a latent image is mainly formed in the middle of the grains. Furthermore, a direct reversal emulsion in which an internal latent image type emulsion and a nucleating agent are used in combination may be used. Examples of the internal latent image type emulsions suitable for this purpose are described in U.S. Pat. Nos. 2,592,250 and 3,761,276, Japanese Patent Publication No. 3534/83 and Japanese Patent Application (OPI) No. 136641/82, etc. Preferred examples of the nucleating agents suitably used in this invention are described in U.S. Pat. Nos. 3,227,552, 4,245,037, 4,255,511, 4,266,031 and 4,276,364 and West German Patent Application (OLS) No. 2,635,316.

The silver halide emulsions for use in this invention may be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxanol dyes. Of these dyes, cyanine dyes, merocyanine dyes, and complex merocyanine dyes are particularly useful. Any conventionally utilized nucleus for cyanine dyes is applicable to these dyes as a basic heterocyclic nucleus. That is, a pyrroline nucleus, an oxazoline nucleus, a thiazoline nucleus, a pyrrole nucleus, an oxazole nucleus, a thiazole nucleus, a selenazole nucleus, an imidazole nuclues, a tetrazole nucleus, a pyridine nucleus, etc., and further nuclei formed by condensing an alicyclic hydrocarbon ring with these nuclei and nuclei formed by condensing an aromatic hydrocarbon ring with these nuclei, that is, an indolenine nucleus, a benzindolenine nuclues, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may be substituted.

To merocyanine dyes and complex merocyanine dyes may be applied 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., as a ketomethylene structure.

These sensitizing dyes may be used individually or in combinations thereof. A combination of sensitizing dyes is often used, particularly for the purpose of supersensitization.

The sensitizing dyes may be present in the emulsion together with dyes which themselves do not give rise to spectrally sensitizing effects but which exhibit a supersensitizing effect or with materials which do not substantially absorb visible light but which exhibit a supersensitizing effect. For example, aminostiryl compounds substituted by a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations as described in U.S. Pat. Nos. 3,615,613, 3,615,641, 3,617,295, and 3,635,721 are particularly useful in this invention.

Gelatin is advantageously used as the binder or protective colloid in the emulsion layers or interlayers of the photographic light-sensitive materials of this invention but other conventional hydrophilic colloids may be used alone or together with gelatin.

The gelatin may be a limed gelatin or an acid-treated gelatin. Details of the preparation of the gelatin are described in Arther Vaise, *The Mocromolecular Chemistry of Gelatin,* published by Academic Press, 1964.

The photographic emulsions for use in this invention may contain surfactants singly or as a combination thereof.

The surfactants are essentially used as a coating aid and sometimes that are used for some other purposes such as emulsification and dispersion, improvement of photographic characteristics for sensitization, static prevention, and blocking prevention. These surfactants are classified into natural surfactants such as saponin, nonionic surfactants such as alkyleneoxide type, glycerin type or glycidol type surfactants, cationic surfactants such as higher alkylamine quaternary ammonium salts, pyridine and the like heterocyclic compounds or phosphonium or sulfonium salts, anionic surfactants containing an acid group, such as a carboxylic acid, sulfonic acid, phosphoric acid, sulfate or phosphote group, and a photeric surfactants such as amino acids, aminosulfonic acids, or aminoalcohol sulfates or phosphates.

The photographic emulsions for use in this invention may contain various compounds for the purpose of the prevention fog in manufacture, storage or photographic processing of the photographic materials or for the purpose of stabilization of photographic characteristics of the materials. For these purposes, various compounds which are known as anti-foggants or stabilizers may be used, including azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiaziazoles, aminotriazoles, benzotriazoles, nitrobenzotriazoles, mercaptotetrazoles (particularly, 1-phenyl-5-mercaptotetrazole), etc.; mercaptopyridmidines; mercaptotrazines; thioketo compounds such as oxazolinthione, etc.; azaindenes such as triazaindenes, tetrazaindenes (particularly, 4-hydroxy-substituted (1,3,3a,7-tetrazaindenes), pentazaindenes, etc.; as well as benzenethiosulfonic acid, benzenesulfinic acid and benzenesulfonic acid amide.

The photographic emulsion layers of the photographic light-sensitive materials of this invention may contain, for the purpose of increasing sensitivity, intensification of contrast or accelerattion of development, for example, thioether compounds, thiomorpholines, quaternary ammonium salt compounds, urethane derivatives, urea derivatives, imidazole derivatives or 3-pyrazolidones.

The photographic light-sensitive material of this invention may further contain in the photographic emulsion layer or in any other hydrophilic colloid layer, a water-soluble or sparingly soluble synthetic polymer dispersion for the purpose of improvement of the dimensional stability of the photographic material. Polymers suitable are homopolymers or copolymers of alkyl (meth)acrylates, alkoxyalkyl (meth)acrylates, glycodyl (meth)acrylates, (meth)acrylamides, vinyl esters (such as vinyl acetate, etc.), acrylonitrile, olefins, and/or styrenes; as well as copolymers made of a combination of the aforesaid monomers and other monomer components such as acrylic acid, methacrylic acid, $\alpha,\beta$-unsaturated dicarboxylic acids, hydroxyalkyl (meth)acrylates, sulfoalkyl (meth)acrylates and styrenesulfonic acids.

Hydrophilic colloids are preferred as the binder for the emulsion layers or auxiliary layers (such as protective layers, interlayers, etc.) of the photographic light-sensitive materials of this invention, and gelatin is most preferred. Other hydrophilic colloids than gelatin may, of course, be used. For example, gelatin derivatives, graft polymers of gelatin and an other high molecular weight compound, albumin, casein or like proteins; cellulose derivatives such as hydroxyethyl cellulose, carboxymethyl cellulose and cellulose sulfate esters, saccharide derivatives such as sodium alginate, starch derivatives, etc.; homopolymer or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used. In addition, limed gelatin, acid-treated gelatin or enzyme-treated gelatin may also be used.

The photographic light-sensitive materials of this invention may contain in the photographic emulsion layers and in any other hydrophilic colloid layer, an inorganic or organic hardening agent. For example, chromium salts (such as chromium alum, chromium acetate, etc.), aldehydes (such as formaldehyde, glyoxal, glutaraldehyde, etc.), N-methylol compounds (such as dimethylolurea, methyloldimethylhydantoin, etc.), dioxane derivatives (such as 2,3-dihydroxydioxane, etc.), active vinyl compounds (such as 1,3,5-triacryloyl-hexahydro-s-triazine, 1,3-vinylsulfonyl-2-propanol, etc.), active halogen-containing compounds (such as 2,4-dichloro-6-hydroxy-s-triazine, etc.), mucohalogenic acids (such as mucochloric acid, mucophenoxychloric acid, etc.,), etc., may be used singly or as a combination thereof.

The silver halide photographic materials of the present invention may contain other various conventional additives as are well known in the art, for example, whitening agents, dyes desensitizers, coating assistants, antistatic agents, plasticizers, sliding agents, matting agents, development accelerators, mordanting agents, ultraviolet light absorbents discoloration inhibitors and color fog-preventing agents.

Examples of such additives which may be used in the present invention are disclosed, for example, in *Research Disclosure*, Vol. 176, RD. No. 17643 (Dec., 1978), pp. 22–31.

The compounds of formula (I) of the present invention may be used in various types of silver halide photographic materials, some examples of which are described hereunder.

(1) The present compounds are effective to improve the quality of silver halide photographic materials for photomechanical processing which have a silver chlorobromide or silver chloroiodobromide emulsion layer containing at least 60% silver chloride an 0 to 5% silver chlorobromide (the emulsion preferably being a monodispersed emulsion) and which contain a polyalkyleneoxide(s). For instance, in the case PUG in compound (I) is a development inhibitor, improving to e sharpness is possible without deteriorating dot quality. In the case PUG is a development accelerator, the compounds of formula (I) are effective for intensification of sensitivity and improving dot quality. In such cases, the amount of the present compound used is $1\times10^{-7}$ mole to $1\times10^{-1}$ mole, especially $1\times10^{-6}$ mole to $1\times10^{-2}$ mole per mole of silver halide.

The polyalkylene oxides used herein may be added to the silver halide photographic materisl(s) or to the developer(s), or to both the silver halide photographic material(s) and the developer(s).

Useful polyalkylene oxides include polyalkylene oxides having 2 to 4 carbon atoms, such as ethylene oxide, propylene-1,3-oxide or butylene-1,2-oxide; condensation products of polyalkylene oxides, which preferably comprise at least ten ethylene oxide units, and compounds having at least one active hydrogen atom, such as water, aliphatic alcohols, aromatic alcohols, fatty acids, organic armines or hexital derivatives; as well as block copolymers compris- two or more polyalkylene oxides. Examples of usable polyalkylene oxide compounds are polyalkylene glycols, polyalkylene glycol alkylethers, polyalkylene glycol arylethers, polyalkylene glycol (alkylaryl)esters, polyalkylene glycol esters, polyalkylene glycol fatty and amides, polyalkylene glycol amines, polyalkylene glycol block copolymers, polyalkylene glycol graft copolymers, etc.

The molecular weight of the polyalkylene oxides preferably used is most suitably 500 to 10,000.

These polyalkylene oxide compounds may be used alone as a combination of two or more thereof.

In the case the polyalkylene oxide compounds are added to the silver halide photographic material, the amount of the compound is preferably $5\times10^{-4}$ g to 5 g, more preferably $1\times10^{-2}$ g to 1 g, per mole of the silver halide. In the case the polyalkylene oxide compounds are to be added to the developer(s), the amount of the compound is generally 0.1 g to 10 g per one liter of the developer.

(2) The compounds of formula (I) of the present invention are effective to improve (or elongation) the dot gradation of photographic materials having monodispersed silver halide emulsion layers capable of forming negative images of ultra-high contrast by development with developers stabilized by the action of hydrazine derivatives, e.g., as described in U.S. Pat. Nos. 4,224,401, 4,168,977, 4,241,164, 4,311,781, 4,272,606, 4,221,857, 4,243,739, 4,272,614, and 4,269,929, without deterioration of the dot quality of the materials.

In the above development, stabilized developers are those containing at least 0.15 mol/liter of such sulfite ion as a preservative and a pH of 10.0 to 12.3. Such developers are those containing a large amount of such preservative, are more stable than conventional lith developers which contain only an extremely low amount of the sulfite ion, and, having a reltively low pH value, are hardly subjected to oxidation by the air and are more stable, for example, than developers (pH of 12.8) in the high contrast image formation system as described in U.S. Pat. No. 2,419,975.

In the present case, PUB in the compounds of formula (I) of the present invention is preferably a compound having development acceleration activity in high contact image formation systems containing a hydrazine derivative.

Examples of preferred compound are hydroxytetraazaindene derivative as described in Japanese Patent Application (OPI) No. 83714/78, thioamide compounds as described in Japanese Patent Application (OPI) No. 137133/78, heterocyclic quaternary salt compounds as described in Japanese Patent Application (OPI No. 77616/78 and amine compounds as described in Japanese Patent Application (OPI) No. 140340/85, and, in particular, hydroxytetraazaindene derivatives are especially preferred. In the present case, the compounds of formula (I) of the present invention are preferably used in an amount of around $1\times10^{-5}$ mole to $8\times10^{-2}$ mole, especially preferably from $1\times10^{-4}$ mole to $5\times10^{-2}$ mole, per mole of silver halide.

In the case the hydrazine derivatives are to be incorporated into a photographic material per the present invention, they are preferably incorporated into the silver halide emulsion layers, or may also be incorporated into any other non-light-sensitive hydrophilic colloid layers (such as protedtive layers, intermediate layers, filter layers, anti-halation layers). For instance, in the case the compounds are soluble in water, they may be added in the form of an aqueous solution; and in the case they are sparingly soluble in water, they may be added to a hydrophilic colloid solution in the form of a solution as dissolved in water compatible organic solvents such as an alcohol(s), ester(s) or ketone(s). In the case these compounds are to be added to a silver halide emulsion layer(s), the addition may be carried out in any desired stage from the beginning of chemical ripening to before the coating of the emulsions, and, in particular, addition is preferably carried out during the period from after chemical ripening to before emulsion coating. It is especially preferred to add the compound to the coating solution which is being prepared just for coating.

With respect to the amount of hydrazine derivative(s) to be added, the optimum amount is desirably selected depending upon the grain diameter of the silver halide emulsion(s), the halogen composition thereof and the method and degree of chemical sensitization of the emulsion(s) as well as the relation between the layers to which the compound(s) is/are to be added and the silver halide emulsion layer(s) and the kinds of anti-fogging compounds. Further, the testing method for selection will be known by one skilled in the art. In general, the amount is preferably $10^{-6}$ mole to $1\times10^{-1}$ mole, especially preferably from $10^{-5}$ mole to $4\times10^{-2}$ mole, per mole of the silver halide.

(3) The compounds of formula (I) of the present invention may be applied to multi-layer multi-color photographic materials having at least two light-sensitive layers on a support, each with a different spectral sensitivity, mainly for the purpose of fog inhibition, gradation regulation, improving color reproducibility and sensitization. Multi-layer natural color photographic materials have, in general, at least one red-sensitive emulsion layer, at least one green-sensitive emulsion layer and at least one blue-sensitive emulsion layer on a support. The order of provision of these layers may freely be determined in accordance with the necessity thereof. The preferred order for the arrangement of the layers comprises a red-sensitive layer, a green-sensitive layer and a blue-sensitive layer from the support, or a blue-sensitive layer, a red-sensitive layer and a green-sensitive layer from the side of the support. Each of these emulsion layers may comprise two or more emulsion layers which have a different sensitivity, or a non-light-sensitive layer may be provided between or among two or more emulsion layers having the same sensitivity. In general, the red-sensitive emultion layer contains a cyan-forming coupler, the green-sensitive emulsion layer contains a magenta-forming coupler and the blue-sensitive emulsion layer contains a yellow-forming coupler, but, as desired other different combinations may be used per the present invention.

Various color couplers may be used in the present photographic materials. "Color couplers" herein mean compounds capable of forming dyes by a coupling reaction with an oxidized aromatic primary amine developing agent. Typical examples of usable color couplers are naphthol or phenol type compounds, pyrazolone or pyrazoloazole type compounds and open or heterocyclic ketomethylene compounds. Examples of cyan, magenta and yellow couplers which may be used in the present invention are described in the patent publicatins referred to in *Research Disclosure,* Vol. 176, RD No. 17643 (Dec., 1978), Item VII-D and ibid., Vol. 187, RD No. 18717 (Nov., 1979).

The color couplers to be incorporated in the photographic materials of this invention are preferably non-diffusible and have a ballast group or are polymerized. Two equivalent couplers where the coupling split-off group is substituted are preferred to four equivalent coupler where the coupling active site has a hydrogen atom, becuase the amount of the silver coated is reduced. Further, couplers capable of forming a dye with a diffusible, non-coloring coupler, a DIR coupler capable of releasing a development inhibitor on coupling or a coupler capable of releasing a development accelerator on coupling may also be used.

Typical yellow couplers used in the present invention are oil protected acylacetamide couplers. Examples are described, e.g., in U.S. Pat. Nos. 2,407,210, 2,875,057 and 3,265,506. Two equivalent yellow couplers are preferably used in the present invention, and examples are oxygen atom-releasing type yellow couplers as described in U.S. Pat. Nos. 3,408,194, 3,447,928, 3,933,501, and 4,022,620; and nitrogen atom releasing type yellow couplers as described in Japanese Patent Publication No. 10739/83, U.S. Pat. Nos. 4,401,752 and 4,326,024, *Research Disclosure,* Vol. 180, RD No. 18053 (April, 1979), British Pat. No. 1,425,020 and German Pat. (OLS) Nos. 2,219,917, 2,261,361, 2,329,587, and 2,433,812. The α-pivaloylacetanilide type couplers are excellent in the fastness of the colored dyes, in particular, in the light fastness thereof, and the α-benzoylacetanilide type couplers generally form dyes of high color density.

The magenta couplers which may be used in the present invention are oil protected type indazolone or cyanoacetyl couplers especially 5-pyrazolone type or pyrazoloazole type couplers, such as pyrazolotriazoles. Among the 5-pyrazolone type couplers, those in which the 3-position is substituted by an arylamino group or an acylamino group are preferred in view of the hue or the color density of the colored dyes; typical examples thereof are described in U.S. Pat. Nos. 2,311,082, 2,343,703, 2,600,788, 2,908,573, 3,062,653, 3,152,896, and 3,936,015. As the releasing group in the two equivalent 5-pyrazolone type couplers, preferred are the nitrogen atom-releasing groups as described in U.S. Pat. No. 4,310,619 and the arylthio groups as described in U.S. Pat. No. 4,351,897. The 5-pyrazolone type couplers with a ballast group as described in European Pat. No. 73,636 also can form dyes with a high color density and are useful herein.

Examples of pyrazoloazole type couplers useful herein are pyrazolobenzimidazoles as described in U.S. Pat. No. 3,061,432, preferably pyrazole(5,1-c)(1,2,4) triazoles as described in U.S. Pat. No. 3,725,067, pyrazolotetrazoles as described in *Research Disclosure,* Vol. 242, RD No. 24220 (June, 1984) and Japanese Patent Application (OPI No. 33552/85 and pyrazolopyrazoles as described in ibid., Vol. 242, RD No. 24230 (June, 1984) and Japanese Patent Application (OPI) No. 43659/85. Imidazo(1,2-b) pyrazoles as described in U.S. Pat. No. 4,500,630 are preferable because of the lower yellow side absorption of the colored dyes and the light fastness thereof, and in particular, pyrazolo(1,5-b)(1,2,4)triazoles as described in U.S. Pat. No. 4,540,654 are especially preferred.

Cyan couplers which may be used in the present invention are oil protected type naphthol and phenol couplers; typical examples thereof are naphthol type couplers as described in U.S. Pat. No. 2,474,293, especially oxygen atom-releasing type two equivalent naphthol couplers as described in U.S. Pat. Nos. 4,052,212, 4,146,396, 4,228,233 and 4,296,200. Examples of phenol type couplers are given in e.g., U.S. Pat. Nos. 4,369,929, 2,801,171, 2,772,162, and 2,895,826. Cyan couplers which are resistant to moisture and temperature are preferably used in the present invention, and typical examples thereof are phenol type cyan couplers having an ethyl or higher alkyl group in the m-position of the phenol nucleus, as described in U.S. Pat. No. 3,772,002; 2,5-diacylamino substituted phenol type couplers, as described in U.S. Pat. Nos. 2,772,162, 3,758,308, 4,126,396, 4,334,011, and 4,327,173, German Pat. (OLS) No. 3,329,729 and European Pat. No. 121,365; and phenol type couplers having a 2-phenylureido group and a 5-acrylamino group, as described in U.S. Pat. Nos. 3,446,622, 4,333,999, 4,451,559, and 4,427,767. In addition, naphthol type cyan couplers having a sulfonamido or amino group in the 5-position of the naphthol nucleus thereof, as described in Japanese Patent Application (OPI) No. 237448/85 and European Pat. No. 161,626, can preferably be used in the present invention, to form color images of high fastness.

In order to correct unnecessary absorption of dyes formed from the magenta and cyan couplers in the short wavelength region, colored couplers are preferably used in color negative photographic materials for photographing. Typical examples of colored couplers are yellow colored magenta couplers as described in U.S. Pat. No. 4,163,670 and Japanese Patent Publication No. 39413/82; and magenta colored cyan couplers as described in U.S. Pat. No. 4,004,929 and 4,138,258 and British Pat. No. 1,146,368.

Couplers forming dyes with an appropriate diffusibility may be used for an improvement of graininess. Regarding smearing couplers, examples of magenta couplers are described in U.S. Pat. No. 4,366,237 and British Pat. No. 2,125,570; and yellow, magenta or cyan couplers are described in European Pat. No. 96,570 and German Pat. (OLS) No. 3,234,533.

The dye forming couplers and the aforesaid special couplers may form dimers or higher polymers. Typical examples of polymerized dye forming couplers in general are described in U.S. Pat. Nos. 3,451,820 and 4,080,211. Examples of polymerized magenta couplers are described in British Pat. No. 2,102,173, U.S. Pat. No. 4,367,282 and U.S. patent application special Nos. 849,589 (filed Apr. 8, 1986) and 866,833 (filed May 27, 1986).

Regarding the incorporation of various kinds of couplers into the photographic materials per the present invention, two or more different kinds of couplers may be added to one light-sensitive layer, or the same coupler may, of course, be added to two or more different layers with no problem.

The compounds of the present invention may be used together with couplers, and may be added to the same emulsion layer together with the couplers, or may be added to an intermediate layer(s) or another photographic auxiliary layer(s) in the form of an independent emulsified dispersion.

The amount of the present compounds being used is from 0.1 to 50 mole%, preferably 0.3 to 15 mole% based on the coupler in each light-sensitive layer, or the yellow coupler in the blue-sensitive layer, the magenta coupler in the green-sensitive layer or the cyan coupler in the red-sensitive layer in the color photographic material. The amount is preferably from $1\times10^{-5}$ mol to $8\times10^{-2}$ mol, especially from $1\times10^{-4}$ mol to $5\times10^{-2}$ mol, per mol of the silver halide in the layer to which the present compound is to be added.

(4) The compounds of formula (I) of the present invention are effective to improve photographic characteristics, for example, for the regulation of graininess and gradation of black-and-white photographic materials, especially X-ray photographic materials, having a silver chlorobromide or silver chloroiodobromide emulsion layer(s) containing 0 to 50 mol% silver chloride and up to 15 mol% silver iodide on the side or both sides of the support. In the present case, the amount of the present compound used is from $1\times10^{-6}$ mol to $1\times10^{-1}$ mol, especially from $1\times10^{-5}$ mol to $5\times10^{-2}$ mol per mol of the silver halide.

In addition, the compounds of formula (I) of the present invention may be applied to other photographic materials for various uses, for example, electrophotographic materials, black-and-white photographic materials of high resolving power, black-and-white photographic materials for use in a diffusion transfer process, color X-ray photographic materials and color photographic materials for use in a diffusion transfer process.

In the case the silver halide photographic materials of the present invention are processed by a conventional wet method, any and every general means may be used. Known processing solutions may thus be used. The processing temperature is generally selected in the range of 18° C. to 50° C., but this may be lower than 18° C. or higher than 50° C. In accordance with the desired use of the photographic materials, any black-and-white photographic processing for development for the formation of silver images or color photographic processing for development for the formation of color images may be applied to the materials.

Details on various useful photographic processing procedures are described in T. H. James, 4th Ed., *The Theory of the Photographic Process,* pp. 291–436, and *Research Disclosure,* Vol. 176, RD No. 17643 (December, 1978), pp. 28–30.

For fixing after black-and-white development, conventional fixers of general compositions may be used. The fixers may contain a thiosulfate or thiocyanate as a fixing agent or an organic sulfur containing compound which is known to be effective as a fixing agent. The fixer may contain a water-soluble aluminum salt as a hardener.

After color development, the photographic emulsion layers are generally bleached. The bleaching may be carried out simultaneously with fixing or separately therefrom.

As the bleaching agent there may be used polyvalent metal compounds such as iron(III), cobalt(III), chromium (VI) or copper (II) compounds, peracids, quinones or nitroso compounds. For instance, ferricyanides, bichromates and iron(III) or cobalt(III) organic complexes, for example, with an organic acid such as an aminopolycarboxylic acid (e.g., ethylenediaminetetraacetic acid, nitrilotriacetic acid, 1,3-diamino-2-propanoltetraacetic acid), citric acid or malic acid; persulfates and permanganates; and nitrosophenols, etc., may be used. In particular, potassium ferricyanide, sodium ethylenediaminetetraacetate iron(III) and ammonium ethylenediaminetetraacetate iron(III) are especially useful. Ethylenediaminetetraacetate iron(III) complexes are useful either in an independent bleaching solution or in a combined bleach-fix bath.

The bleaching or bleach-fixing solution may contain various additives such as a bleach accelerator as described in U.S. Pat. Nos. 3,042,520 and 3,241,966 and thiol compound as described in Japanese Patent Application (OPI) No. 65732/78.

In particular, compounds of formula (I) of the present invention where a diffusible dye has been introduced as a PUG group are preferably used for heat developable silver halide photographic materials where mobile dyes are formed by heat development and these are transferred to and fixed in a dye fixing layer, as described, e.g., in Japanese Patent Application (OPI) Nos. 149046/83, 154445/84, 165054/84, 180548/84, 218443/84, and 133449/85 and U.S. Pat. Nos. 4,503,137, 4,474,876, 4,483,914, 4,455,363 and 4,500,626.

In the case the present compounds are used in heat developable photographic materials, the compounds do not always require an electron transfer agent (ETA). That is, the use of only the reducing substance (RE) enables to sufficiently take place the reaction. In particular, the use of 4-substituted sulfonamidonaphthols are preferred.

In the case the present compounds are used in heat developable photographic materials, organic metal salts may be used as an oxidizing agent, together with the light-sensitive silver halide(s). In this case, the light-sensitive silver halide(s) and the organic metal salt(s) are necessarily kept in direct contact with each other or in close contact with each other.

Among the organic metal salts, organic silver salts are especially preferred.

Organic compounds useful for the formation of the aforesaid organic silver salt oxidizing agents are described, e.g., in Japanese Patent Application (OPI) No. 107243/86 and U.S. Pat. No. 4,500,626 (52nd column and 53rd column). In addition, silver salts of alkynyl group containing carboxylic acids such as silver phenylpropiolate, as described in Japanese Patent Application (OPI) No. 113235/85, are also useful.

The amount of the organic silver salt(s) which may be used is 0.01 to 10 moles, preferably 0.01 to 1 mole, per mole of the light-sensitive silver halide. The total amount of the light-sensitive silver halide and the organic silver salt as coated is suitably 50 mg/m$^2$ to 10 g/m$^2$, calculated in terms of the coated silver amount.

The image forming materials of heat developable photographic materials may be compounds of formula (I) of the present invention which have a dye as PUG, or otherwise, if the compounds of formula (I) where PUG is a photographically useful group other than dyes which are used in heat developable photographic materials. The image forming materials thereof may be silver, or the materials may contain a compound capable of forming or releasing a mobile dye in the reduction of light-sensitive silver halide to silver under high temperaure conditions, in accordance with or reversely in accordance with said reaction, i.e., a dye-providing materials.

Examples of the dye-providing materials which may be used in the present invention are, first the aforesaid couplers. In addition, two equivalent couplers which have a non-diffusible group as a split-off group and which form a diffusible dye by reaction with oxidized developer are also preferably used. Examples of these couplers are described in detail in T. H. James, *The Theory of the Photographic Process*, pp. 291–334 and pp. 354–361; and Japanese Patent Application (OPI) Nos. 123533/83, 149046/83, 149047/83, 111148/84, 124399/84, 174835/84, 231539/84, 231540/84, 2950/85, 2951/85, 14242/85, 23474/85, and 66249/85.

Another example of the dye providing material is a dye-silver compound in which an organic silver salt is connected to a dye. Specific examples of the dye-silver compounds are described in *Research Disclosure*, Vol. 169, RD No. 16966 (May, 1978), pp. 54 to 58, etc.

Still another example of the dye providing material is an azo dye used in a heat developable silver dye bleaching process. Specific examples of the azo dyes and the method for bleaching are described in U.S. Pat. No. 4,235,957, *Research Disclosure*, Vol. 144, RDNo. 14433 (April, 1976), pp. 30 to 32, etc.

A further example of the dye providing material is a leuco dye as described in U.S. Pat. Nos. 3,985,565 and 4,022,617, etc.

A still further example of the dye providing material is a compound having a function of imagewise releasing a diffusible dye.

This type of compound can be represented by formula (LI)

$$(\text{Dye—X})_n\text{—Y} \qquad \text{(LI)}$$

wherein Dye represents a dye moiety, a dye moiety temporarily shifted to the short wavelength range or a dye precursor moiety; X represents a chemical bond or a connecting group; Y represents a group having a property such that diffusibility of the compound represented by $(\text{Dye—X})_n\text{—Y}$ can be differentiated in correspondence or counter-correspondence to light-sensitive silver salts having a latent image distributed imagewise or a group having a property of releasing Dye in correspondence or counter-correspondence to light-sensitive silver salts having a latent image distributed imagewise, diffusibility of Dye released being different from that of the compound represented by $(\text{Dye—X})_n\text{—Y}$; and n represents 1 or 2 and when n is 2, the two Dye—X groups are the same or different.

Specific example of the dye providing material represented by formula (LI) include, for example, dye developers in which a hydroquinone type developing agent (reducing agent) is connected to a dye component are described in U.S. Pat. Nos. 3,134,764, 3,362,819, 3,597,200, 3,544,545 and 3,482,972, etc. Further, materials capable of releasing diffusible dyes upon an intramolecular nucleophilic displacement reaction are described in Japanese Patent Application (OPI) No. 63618/76, etc., and materials capable of releasing diffusible dyes upon an intramolecular rearrangement reaction of an isooxazolone ring are described in Japanese Patent Application (OPI) No. 111628/74, etc.

In any of these processes, diffusible dyes are released in portions where development does not occur. In contrast, in portions where development occurs neither release nor diffusion of dyes take place.

There has been provided a process in which a dye releasing compound is preliminarily converted to an oxidized form thereof which does not have a dye releasing ability, the oxidized form of the compound is coexistent with a reducing agent or a precursor thereof, and after development the oxidized form is reduced with the remaining agent which is not oxidized to release a diffusible dye. Specific examples of dye providing materials which can be used in such a process are described in Japanese Patent Application (OPI) Nos. 110827/78, 130927/79, 164342/81, 35533/78, etc.

On the other hand, materials capable of releasing diffusible dyes in portions where development occurred are also known. For example, materials capable of releasing diffusible dyes in the releasing groups thereof with oxidation products of developing agents (reducing agents) are described in British Pat. No. 1,330,524, Japanese Patent Publication No. 39165/73, U.S. Pat. No. 3,443,940, etc., and materials capable of forming diffusible dyes upon a reaction of couplers having diffusion resistant groups in the releasing groups thereof with oxidation products of developing agents are described in U.S. Pat. No. 3,227,550, etc.

In these processes using color developing agents, there is a severe problem in that images are contaminated with oxidation decomposition products of the developing agents. Therefore, in order to eliminate such a problem, dye releasing compounds which have reducing property themselves and thus do not need the use of developing agents have been proposed. (As a matter of course, the above-described reducing agents may be auxiliary used.) Such dye providing compounds are described, e.g., in U.S. Pat. Nos. 3,928,312, 4,053,312, 4,055,428, 4,336,322, 3,725,062, 3,728,113, 3,443,939, and 4,500,626 and Japanese Patent Application (OPI) Nos. 65839/84, 3819/78, 104343/76, 116537/83, and 179840/82, and *Research Disclosure,* Vol. 174, RD No. 17465 (October, 1978).

Specific examples of dye providing materials which can be used in the present invention are the compounds as described in aforesaid U.S. Pat. No. 4,500,626 (from the 22nd column to the 44th column), and in particular, Compounds (1)-(3), (10)-(13), (16)-(19), (28)-(30), (33), (35), (38)-(40) and (42)-(64) among the compounds of the said U.S. Patent are expecially preferred.

The aforesaid dye providing materials and other hydrophobic additives such as image forming accelerators, which will be described hereafter, may be introduced into the layers of the photographic materials in a conventional manner, for example, by the method described in U.S. Pat. No. 2,322,027. For introduction, high boiling point organic solvents as described in Japanese Patent Application (OPI) Nos. 83154/84, 17845/84, 178452/84, 178453/84, 178454/84, 178455/84, and 178457/84 may be used, optionally together with a low boiling point organic solvent(s) having a boiling poing of 50° C. to 160° C.

The amount of the high boiling point-organic solvent to be used is generally 10 g or less, preferably 5 g or less, to 1 g of the dye providing materials.

In addition, the dispersion method using polymers described in Japanese Patent Publication No. 39853/76 and Japanese Patent Application (OPI) No. 59943/76 may also be used.

In the case the compounds are substantially insoluble in water, fine particles of the compound may be dispersed in a binder and the resulting dispersion may be introduced into the layers.

For the dispersion of hydrophobic materials into hydrophilic colloids, various materials may be used, e.g., those as described in Japanese Patent Application (OPI) No. 157636/84 may be used.

In the present invention, heat developable photographic materials may contain an image forming accelerator. Image forming accelerators have various functions, for example, for the acceleration of the oxidation-reduction reaction of a silver salt oxidizing agent and a reducing agent, acceleration of the formation of dyes from a dye providing substances as well as for the decomposition of dyes or for the release of diffusible dyes and the acceleration of the transfer of dyes from light-sensitive material layers to dye fixing layer. These may be classified into the groups of bases or base precursors, nucleophilic compounds, high boiling point organic solvents (oils), thermal solvents, surfactants and compounds having a mutual action with silver or silver ion, in view of the physico-chemical functions thereof. These groups of substances have, in general, composite functions and thus have two or more of the aforesaid acceleration effects. Details on these materials are described in Japanese Patent Application (OPI) No. 93451/86. In addition to the use of the aforesaid image forming accelerators, other materials are known for the generation of bases, and such compounds are usable as a base precursor in the present invention. For instance, U.S. patent application Ser. No. 890,442 (filed July 30, 1986) and European patent application No. 86 110568.2 (filed July 30, 1986) describe a method for the generation of bases by blending a sparingly soluble metal compound capable of reacting with the metal of the sparingly soluble metal compound for complex formation (which is called a complex forming compound); and Japanese patent application (OPI) No. 232451/86 describes a method for the generation of bases by electrolysis.

In particular, the former method is very effective. Examples of sparingly soluble metal compounds are zinc, aluminium, calcium and barium carbonates, hydroxides and oxides. The complex forming compounds are described in detail, e.g., in A. E. Martell and R. M. Smith, *Critical Stability Constants,* Vols. 4 and 5 published by Plenum Press. Specific examples of such compounds are salts of amino carboxylic acids, imidino acetic acids, pyridyl carboxylic acids, amino phosphoric acids, carboxylic acids (including mono-, di-, tri- and tetra-carboxylic acids as well as those having a substituent such as a phosphono, hydroxyl, oxo, ester, amino, alkoxy, mercapto, alkylthio, phosphino or salts like group), hydroxamic acids, polyacrylates and polyphosphoric acid salts with alkali metals; guanidines, amidines or quaternary ammonium salts.

These sparingly soluble metal compounds and the complex forming compounds are preferably added separately to the light-sensitive materials and the dye fixing materials, individually.

In the present invention, various kinds of development stopping agents may be used in order to obtain constant images at all times despite variations in processing temperature and processing time in heat development.

The development stopping agents herein are compounds capable of neutralizing a base or reacting with a base after the completion of development, to thereby lower the base concentration if the film, thereby stopping the development, or the compounds may mutually react with silver or a silver salt, after the complete development, to inhibit the development. For example, these agents include acid precursors capable of releasing an acid on heating, electrophilic compounds which react an existing base by a substitution reaction on heating, as well as nitrogen-containing heterocyclic compounds, mercapto compounds and precursors thereof. Examples of these compounds are described, e.g., in Japanese patent application (OPI) Nos. 108837/85, 192939/85, 230133/85 and 230134/85.

Further, the compounds which release a mercapto compound by heating are useful and include those described in U.S. patent application Ser. Nos. 774,427 (filed Sept. 10, 1985), 809,627 (filed Dec. 16, 1985), 799,995 (filed Nov. 20, 1985), 827,139 (filed Feb. 7, 1986), 829,032 (filed Feb. 13, 1986), 828,481 (filed Feb. 12, 1986), and 839,031 (filed Feb. 18, 1986), Japanese patent application (OPI) No. 53632/86, etc.

In the present invention, the heat-developable photographic materials can contain compounds which activate the development and stabilizing of the formed images at the same time. Examples of preferred compounds are described in U.S. Pat. No. 4,500,626 (51st dolumn to 52nd column).

In the present invention, various kinds of antifogging agents can be employed. Examples of useful antifogging agents include an azole, a carboxylic acid and a phosphoric acid each containing a nitrogen atom as described in Japanese patent application (OPI) No. 168442/84, a mercapto compound and a metal salt thereof as described in Japanese patent application (OPI) No. 111636/84, etc.

The heat developable photographic materials of the present invention may optionally contain an image toning agent. Examples of usable toning agents are described in U.S. patent application Ser. No. 809,627, filed Dec. 16, 1985.

The supports used for the heat developable photographic materials of the present invention and for the dye fixing materials which are, as the case may be, optionally used in the present invention, are those which are resistant to processing temperatures. In general, conventional supports such as glass, paper, polymer, films, metals and analogues thereof may be used, and in addition, those as described in U.S. patent application Ser. No. 809,627, filed Dec. 16, 1985 may also be used.

The heat developable photographic materials of the present invention may contain various additives which are known to be usable in conventional heat developable photographic materials, and in addition, may contain other layers than the light-sensitive layers, such as antistatic layers, electrically conductive layers, protective layers, intermediate layers, antihalation layers, stripping layers and mat layers. Many useful additives are described in *Research Disclosure,* Vol. 170, RD No. 17029 (June 1978), pp. 9–15 and Japanese patent application (OPI) No. 88256/86, which include, for example, plasticizers, sharpness improving dyes, antihalation dyes, sensitizing dyes, matting agents, surfactants, fluorescent whitening agents, ultraviolet light absorbents, slide inhibitors, antioxidants and color fade-preventing agents.

In particular, protective layers generally contain an organic or inorganic matting agent for the purpose of blocking prevention. In addition, the protective layers may optionally contain a mordant and a UV light absorbent. The present photographic materials may have two or more protective layers and two or more intermediate layers.

The intermediate layers may contain a reducing agent for the prevention of color fading or color mixing a UV light absorbent or a white pigment such as $TiO_2$. The white pigment may be added not only to the intermediate layers, but also to the emulsion layers, for the purpose of intensifying sensitivity.

The photographic elements of the present invention comprise a light-sensitive element capable of releasing or forming a dye(s) on heat development and a dye fixing element for fixing the dyes formed.

Both a light-sensitive element and a dye fixing element are indispensable in a system for the formation of images by diffusion transfer. Such may be classified into two typical systems. In one system, the light-sensitive element and the dye fixing elements are separately provided on two different supports; in the other system, the two elements are provided on the same support.

The relationship between the light-sensitive element and the dye fixing element, between these elements and the support(s) and between these elements and a white reflective layer are described in U.S. patent application Ser. No. 809,627, filed Dec. 16, 1985 (pp. 58–59) and U.S. Pat. No. 4,500,626 (57th column), which may be applied to the present invention.

One representative example of the embodiment in which the light-sensitive element and the dye fixing element are provided on the same support is a type in which the light-sensitive element is not necessary to peel apart from the image receiving element after the formation of transferred images. In such a case, on a transparent or opaque support a light-sensitive layer, a dye fixing layer and a white reflective layer are superposed. Examples of preferred embodiments of layer structure include transparent or opaque support/light-sensitive layer/white reflective layer/dye fixing layer, or transparent support/dye fixing layer/white reflective layer/light-sensitive layer, etc.

Another typical example of the embodiment in which the light-sensitive element and the dye fixing element are provided on the same support is a type in which a part of all of the light-sensitive element is separated from the dye fixing element and a stripping layer is provided on an appropriate position of the element as described, for example, in Japanese patent application (OPI) No. 87840/81, Canadian Pat. No. 674,082, U.S. Pat. No. 3,730,718, etc.

The light-sensitive element or the dye fixing element may form a structure having an electrically conductive heat generating layer suitable for use as heating means for the purpose of heat development or diffusion transfer of dyes.

In this case, the transparent or opaque heating element (layer) may be formed in a conventional manner for the formation of conventional heating elements.

For the formation of a heating element, two methods are generally used. In one method, a thin film of a semiconductive inorganic material is used, and in the other method an organic thin film made of a dispersion of electrically conductive fine particles dispersed in a binder is used. Materials usable in these methods are described in Japanese patent application (OPI) No. 29835/86.

The dye fixing element used in the present invention contains at least one layer containing a mordant, and in the case the dye fixing layer is positioned on the surface of the photographic material, protective layer may optionally be coated thereon.

The layer construction of the dye fixing element, the binder, the additives and the position of the mordant agent containing layer are described in U.S. patent application Ser. No. 809, 627, filed Dec. 16, 1985 and in the patent publication referred to therein, which may be applied to the present invention.

The dye fixing element used in the present invention may optionally have, in addition to the aforesaid layers, a stripping layer, a matting agent layer, a curl preventive layer or like auxiliary layers.

One or more of the above mentioned layers may contain, if necessary, bases and/or base precursors for the acceleration of dye transfer, hydrophilic thermal solvents, color fade-preventing agents for inhibition of the discoloration of the dyes, UV light absorbents, sliding agents, matting agents, antioxidants, vinyl compound dispersions for increased dimensional stability and fluorescent whitening agents. Examples of these additives are described in Japanese patent application (OPI) No. 88256/86.

The binders in the aforesaid layers are preferably hydrophilic, and transparent or semi-transparent hydrophilic colloids are typical. For example, the binders as mentioned in the aforesaid photographic materials may be used.

The image receiving layers of the present invention are dye fixing layers to be used in the heat developable color photographic materials, and the mordants used in the layers may freely be selected from conventional mordants. In particular, polymer mordants are especially preferred. The polymer mordants include tertiary amino group-containing polymers, nitrogen-containing heterocyclic polymers and quaternary cationic group-containing polymers.

Examples of these polymers are described in U.S. patent application Ser. No. 809,627, filed Dec. 16, 1985 and U.S. Pat. No. 4,500,626 (57th column to 60th column).

The method of providing heat developable light-sensitive layers, protective layers, intermediate layers, subbing layers, backing layers and other layers is described in U.S. Pat. No. 4,500,626 (55th column to 56th column), which may be applied to the present invention.

As the light source for image exposure to record the images on the heat developable photographic materials may use radiation including visible rays, and for example, various light sources as described, e.g., U.S. patent application Ser. No. 809,627, filed Dec. 16, 1985 and U.S. Pat. No. 4,500,625 (56th column) may be used.

The heating temperature for development in heat development is generally about 50° C. to about 250° C. and is preferably about 80° C. to about 180° C. The heating temperature for transfer in the transfer step is generally within a range from a temperature in the heat development to room temperature, and is especially preferably within the range from 50° C. or more to the lower temperature than in the heat development step by about 10° C. For the heating means in the development step and/or the transfer step, there may be used a hot plate, a hot roller or any other heating elements with carbon or titanium white.

The development and transfer may be effectively carried out simultaneously or continuously by heating the material in the presence of a small amount of a solvent, such as water, as described in detail in Japanese patent application (OPI) No. 218443/84. In such method, the aforesaid image forming accelerator may earlier be incorporated in either the dye fixing material or the light-sensitive material, or in both, or it may be externally added to the photographic processing system.

In a system where development and transfer are carried out simultaneously or continuously, the heating temperature is preferably from 50° C. or more to the boiling point of the solvent. For instance, when water is used as the solvent, the heating temperature is desirably from 50° C. or higher to 100° C. or lower.

Solvents may be used for the transfer of the mobile dye to the dye fixing layer.

Examples of solvents used for the acceleration of development and/or transfer of the mobile dye to the dye fixing layer are water and a basic aqueous solution containing an inorganic alkali metal salt or an organic base. (The bases are referred to in the item of the image forming accelerators hereinbefore may be used). Further, low boiling point solvents as well as mixtures thereof comprising a low boiling point solvent and water or a basic aqueous solution may also be used. Surfactants, antifogging agents and sparingly soluble metal salt complex forming compounds may be incorporated in the solvent(s).

The solvent(s) may be added to either the dye fixing material or the light-sensitive material or to both. The amount added may be small, i.e. to such a degree that the weight of the solvent used is the same as or less than that which corresponds to the maximum swollen volume of the total coated film, especially the same as the weight or less a left by subtracting the weight of the total coated films from the weight of the solvent which corresponds to the maximum swollen volume of the total coated films.

The solvent (for example, water) may accelerate the formation of the images and/or the transfer of the dyes, when applied between the light-sensitive layer of heat developable photographic material and the dye fixing layer of the fixing material, and the solvent may earlier be incorporated into either the light-sensitive layer or the dye fixing layer or into both.

The incorporation of the solvent into the light-sensitive layer and/or the dye fixing layer is described, e.g., U.S. patent application Ser. No. 809,627, filed Dec. 16, 1985.

For the acceleration of dye transfer, hydrophilic thermal solvents which are solid at room temperature but which dissolve at a higher temperature may be incorporatedinto the light-sensitive materials or the dye fixing materials. The hydrophilic thermal solvents may be incorporated into either the light-sensitive material or the dye fixing material or into both. For incorporation, the solvents may be added to any of the emulsion layer(s), intermediate layer(s), protective layer(s) and dye fixing layer(s), and, in particular, these are especially preferably added to the dye fixing layers and/or an adjacent layer(s).

Examples of thermal solvents are ureas, pyridines, amides, sulfonamides, imides, alcohols, oximes and other heterocyclic compounds.

Exemplary heating means which can be used in the transfer step are described in U.S. patent application Ser. No. 809,627, filed Dec. 16, 1985. For heating, a graphite, carbon black, metal or the like electrically conductive material layer may be coated on the dye fixing material, whereby the electrical conductive layer may directly be heated by imparting an electric current thereinto.

The heat developable light-sensitive material and the dye fixing material are typically laminated under pressure, and typical pressure conditions and the means for the pressure application are described in U.S. patent application Ser. No. 809,627, filed Dec. 16, 1985.

The compounds of the present invention may be used in silver halide photographic materials for color diffusion transfer, which are developed with a developer near room temperature. Such color diffusion transfer is described, e.g., in Belgian Pat. No. 757,959. As the dye providing substances for color diffusion transfer there may be used compounds of formula (I) of the present invention where PUG is a diffusible dye, and in addition, compounds of the following formula (V) may also be used.

Dye—Y (V)

in which Dye represents a dye moiety (or precursor thereof); and Y represents a substrate having a function of varying the diffusibility of the dye providing substance (V) as a result of development.

The wording "to vary the diffusibility" as used herein means that: (1) the dye providing substance (V) is initially non-diffusible and this is changed into a diffusible form or a diffusible dye is released therefrom; or (2) the dye providing substance (V) is initially diffusible and is changed into a non-diffusible form. The change depends upon the property of Y itself, resulting from the oxidation of Y in one case or from the reduction of the Y in the other case.

In the former case where "the diffusibility varies varies because of the oxication of Y", examples of Y are dye releasing redox substrates, which are p-sulfonamidonaphthols (including p-sulfonamidophenols, as described in Japanese patent application (OPI) No. 33826/73 and 50736/78; European Pat. No. 76,492), o-sulfonamidophenols (including o-sulfonamidonaphthols, as described in Japanese patent application (OPI) No. 113624/76, 12642/81, 161830/81, 16131/81, 4043/82, and 650/82, U.S. Pat. No. 4,053,312, and European Pat. No. 75,492), hydroxysulfonamido-heterocyclic compounds (as described in Japanese patent application (OPI) Nos. 104343/76, 46730/78, 140122/79, and 85055/82, and European Pat. No. 76,492), α-sulfonamidoketones (as described in Japanese patent application (OPI) Nos. 3819/78 and 48534/79 and European Pat. No. 76,492).

Another embodiment is a system where the dye is released by an intranuclephilic attack of the compound after oxidation of Y. Intramolecular assistant type substrates as described in Japanese patent application (OPI) Nos. 20735/82 and 65839/84 are the examples of such Y groups.

Still another embodiment involves the use of such a substrate that releases the dye by an intramolecular cyclization reaction under basic conditions but does not substantially release any dye after Y has been oxidized. Examples of the substrates of this kind are described in Japanese patent application (OPI) No. 63618/76. Further substrates that release the dye because of a ring rearrangement of an isoxazolone ring in the substrates of this modified case are described in Japanese patent application (OPI) Nos. 111628/74 and 4819/77).

A further embodiment involves the use of substrates that release the dye moiety by dissociation of an acidic proton under basic conditions but do not substantially release any dye after Y has been oxidized. Examples are described in Japanese patent application (OPI) Nos. 69033/78 and 130927/79.

In the latter case where "the diffusibility varies because of the reduction of Y", examples of Y are nitro compounds as described in Japanese Patent Application (OPI) No. 110827/78 and quinone compounds as described in Japanese Patent Application (OPI) No. 110827/78 and U.S. Pat. Nos. 4,352,249 and 4,358,525. These are reduced by a reducing agent, which is called an electron donor, remaining without having been consumed in development and, as a result, release the dye because of an intramolecular attack by the resulting nucleophilic group. Further, quinone type substrates capable of releasing the dye moiety because dissociation of the acidic proton of the reduced form thereof are usable, which are a modification of the present embodiment. Examples of these substrates are described in Japanese Patent Application (OPI) Nos. 130927/79 and 1t4342/81.

In the case the aforesaid substrates which vary diffusibility because of reduction thereof are used, the pertinent reducing agent (=electron donor) which mediates between exposed silver halide and the dye providing substance is indispensably used, and the examples of such agents are described in the aforesaid publications. So called LDA compounds which per se contain an electron donor in the substrate Y may also be effectively used.

The aforesaid dye providing substances form a mobile-dye in imagewise distribution in the photographic material by wet development, which corresponds to exposure of the material, and the dye image is transferred to the dye fixing material by diffusion transfer to obtain a visible image thereon.

Photographic elements for color diffusion transfer will now be explained in greater detail.

Photographic elements for color diffusion transfer are preferably in the form of a film unit comprising a combination of the light-sensitive material (light-sensitive element) and the dye fixing material (image receiving element).

In one typical embodiment of such a film unit, the image receiving element and the light-sensitive element are laminated on one transparent support, and the light-sensitive element need be peeled off from the image receiving element after the completion of the image transfer. More precisely, the image receiving element comprises at least one mordant layer; and the light-sensitive element preferably comprises the combination of a blue-sensitive emulsion layer, a green-sensitive emulsion layer and a red-sensitive emulsion layer, the combination of a green-sensitive emulsion layer, a red-sensitive emulsion layer and an infrared-sensitive emulsion layer or the combination of a blue-sensitive emulsion layer, a red-sensitive emulsion layer and an infrared-sensitive emulsion layer, and the corresponding yellow dye providing substance, magenta dye providing substance and cyan dye providing substance are incorporated into each of these emulsion layer. An "infrared-sensitive emulsion layer" means an emulsion layer having light sensitivity to light of 700 nm or more, especially 740 nm or more. A white reflective layer containing a solid pigment such as titanium oxide is normally provided between the mordant layer and the light-sensitive layer or the dye providing substance-containing layer, whereby the transferred image may be seen through the transparent support. A light shielding layer may be provided between the white reflective layer and the light-sensitive layer so that the development may be carried out in the light. If necessary, a peeling layer may be provided so that a part of all of the light-sensitive element may be peeled off the image receiving element. Examples of this embodiment are described, e.g., Japanese Patent Application (OPI) No. 67840/81 and Canadian Pat. No. 674,082.

In another non-peeling type embodiment, the light-sensitive element is coated on the transparent support, the white reflective layer is coated thereover and the image receiving layer is further superposed thereover. A system where the image receiving element, the white reflective layer, the peeling layer and the light-sensitive element are laminated on the same support and the light-sensitive element is peeled off the image receiving element is described in U.S. Pat. No. 3,730,718.

On the other hand, a system where the light-sensitive element and the image receiving element are separately provided on two different supports is typically classified into two types. One is a peeling type and the other is non-peeling type. These two types will now be explained in detail.

In one preferred embodiment of a peeling-type film unit, a light reflective layer is provided on the back surface of the support and at least one image receiving layer is provided on the front surface thereof. This embodiment is so planned that the light-sensitive element is provided on the support having a light shielding layer and that the light-sensitive layer coated surface is reversed to face to the image receiving layer coated surface after the exposure (or, for example, during development) while the light-sensitive layer coated surface and the mordant layer coated surface are not faced to each other before exposure. After the completion of the image transfer to the mordant layer, the light-sensitive element is immediately peeled off the image receiving layer.

In another preferred embodiment of a non-peeling type film unit, at least one mordant layer is provided on the transparent support and the light-sensitive element is provided on the transparent or light shielding layer coated support, whereupon the light-sensitive layer coated surface and the mordant layer coated surfaces are kept to face to each other.

A photographic element of the aforesaid color diffusion transfer type may optionally be combined with a container (or processing element) which contains an alkaline processing solution and which may be ruptured under pressure. In a non-peeling type film-unit comprising an image receiving element and a light-sensitive element laminated on one support, in particular, the processing element is preferably provided between the light-sensitive element and a cover sheet coated thereon. In another embodiment where the light-sensitive element and the image receiving element are separately provided on respective two supports, the processing element is preferably provided between the light-sensitive element and the image receiving element at least during development. The processing element preferably contains a light shielding agent (such as carbon black or dye(s) whose color may vary because of variations in pH) and/or a white pigment (such as titanium white). In color diffusion transfer type film units, it is preferred that the cover sheet, the image receiving element or the light-sensitive element be combined with a neutralization timing system comprising the combination of a neutralizing layer and a neutralization timing layer.

The present invention will now be explained in greater detail by reference to the following examples, which, however, are not intended to be interpreted as limiting the scope of the present invention.

EXAMPLE 1

A light-sensitive material (Sample 101) was prepared by forming, in succesion, the following layers (1) to (11).

(1) A layer containing the DRR compound (0.36 mmol/m$^2$) shown below, tricyclohexyl phosphate (0.09 g/m$^2$), 2,5-di(t-pentadecyl)hydroquinone (0.01 g/m$^2$) and gelatin (0.44 g/m$^2$).

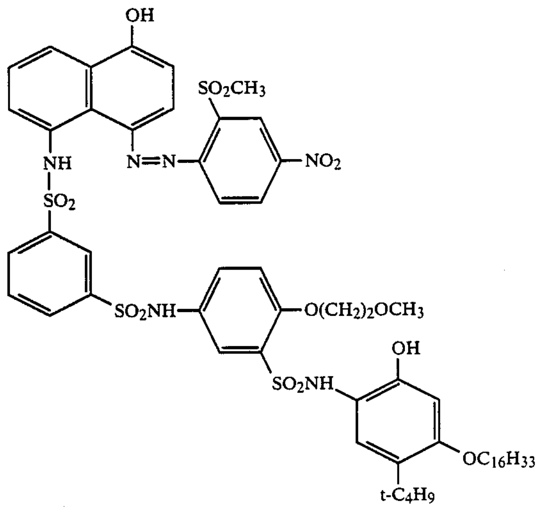

(2) A layer containing a red-sensitive internal latent image type direct reversal silver bromide emulsion (0.5 g/m$^2$ as silver), gelatin (0.78 g/m$^2$), the nucleating agent (27 g/m$^2$) shown below, and sodium pentadecylhydroquinonesulfonate (0.06 g/m$^2$).

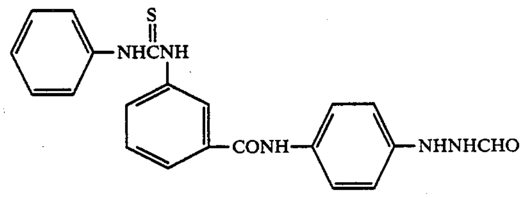

(3) a layer containing 2,5-di-(tert-pentadecyl)hydraquinone (0.71 g/m$^2$), a copolymer of vinylpyrrolidone and vinyl acetate (7:3 by mol ratio) (0.24 g/m$^2$), and gelatin (0.4 g/m$^2$).

(4) A layer containing gelatin (0.3 g/m$^2$).

(5) A layer containing containing the magenta DRR compound (0.49 $g/m^2$) shown below, tricyclohexyl phosphate (0.8 $g/m^2$), 2,5-di-(tert-pentadecyl)hydroquinone (0.01 $g/m^2$), and gelatin (0.5 $g/m^2$).

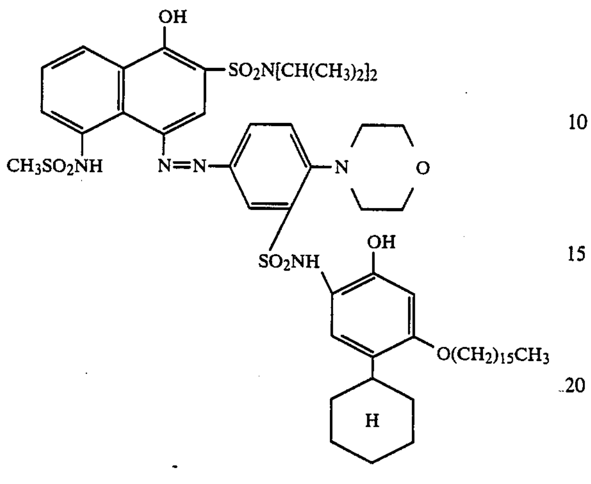

(6) A layer containing a green-sensitive internal latent image type direct reversal silver bromide emulsion (0.34 $g/m^2$ as silver amount), gelatin (0.66 $g/m^2$), the nucleating agent (12.9 $\mu g/m^2$) employed in Layer (2), and sodium pentadecylhydroquinonesulfonate (0.04 $g/m^2$).

(7) A layer containing 2,5-di-(tert-pentadecyl)hydroquinone (0.71 $g/m^2$), a copolymer of vinylpyrrolidone and vinyl acetate (mol ratio of 7:3) (0.24 $g/m^2$), and gelatin (0.4 $g/m^2$).

(8) A layer containing gelatin (0.25 $g/m^2$).

(9) A layer containing the yellow DRR compound (0.48 $g/m^2$) shown below, tricyclohexyl phosphate (0.03 $g/m^2$), 2,5-di-(tert-pentadecyl)hydroquinone (0.004 $g/m^2$), and gelatin (0.43 $g/m^2$).

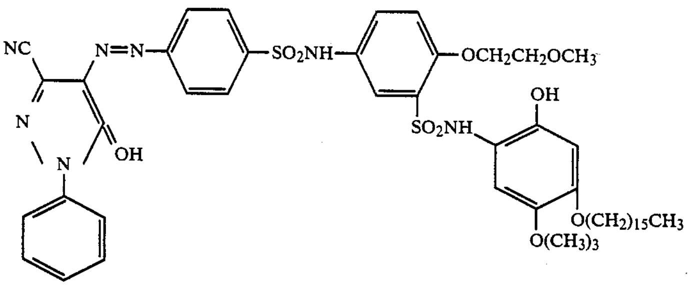

(10) A layer containing a blue-sensitive internal latent image type direct reversal silver bromide emulsion (0.84 $g/m^2$ as silver amount), gelatin (0.9 $g/m^2$), the nucleating agent (29 $\mu g/m^2$) employed in Layer (5), and sodium pentadecylhydroquinonesulfonate (0.05 $g/m^2$).

(11) A layer containing gelatin (1.0 $g/m^2$).

A photographic light sensitive material (Sample 102) containing the dispersion of the following composition in the aforesaid red-sensitive emulsion layer, the green-sensitive emulsion layer and blue-sensitive emulsion layer was prepared.

(a) An antifoggant-releasing compound 14 (0.1 m mol/$m^2$) of this invention.

(b) a reducing material S-45 (0.1 mmol/$m^2$) converted into the precursor thereof.

(c) Trihexyl phosphate (0.01 $g/m^2$).

Also, a dye image receiving sheet was prepared by coating, in succession, the following layers (1) to (5) on a white support having on the back side coated, in succession, a carbon black layer and a titanium while layer.

(1) A layer containing a copolymer (22 $g/m^2$) of acrylic acid and butyl acrylate at 80:20 by weight ratio and 4-bis(2,3-epoxypropoxy)butane (0.44 $g/m^2$).

(2) A layer containing acetyl cellulose (formed using 39.4 g of acetyl group by the hydrolyze of 100 g of the acetyl cellulose) (3.8 $g/m^2$), a copolymer (molecular weight about 50,000) (0.2 $g/m^2$) of styrene and maleic anhydride at 60:40 by weight ratio, and 5-(β-cyanoethylthio)-1-phenyltetrazole (0.115 $g/m^2$).

(3) A layer containing a copolymer latex (2.5 $g/m^2$) of vinylidene chloride, methyl acrylate, and acrylic acid at 85:12:3 by weight ratio and polymethyl methacrylate latex (particle size 1 to 3 microns) (0.05 $g/m^2$).

(4) A layer containing a mordant (3.0/$m^2$) having the following formula and gelatin (3.0 $g/m^2$).

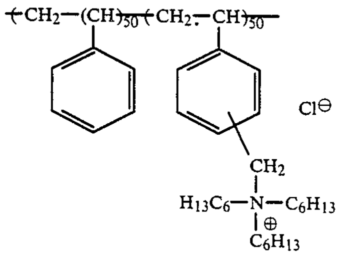

(5) A layer containing phthalated gelatin (1 $g/m^2$).

Then, a processing solution having the following composition was filled in a rupturable container in an amount of 0.8 g.

| Processing Solution: | | |
|---|---|---|
| Benzyl Alcohol | 0.20 | ml |
| 1-Phenyl-4-hydroxymethyl-4-methyl-3-pyrazolidinone | 0.3 | g |
| Methylhydroquinone | 0.012 | g |
| 5-Methylbenzotriazole | 0.6 | g |
| Sodium Sulfite | 0.18 | g |
| Hydroxymethyl Cellulose | 4 | g |
| Potassium Hydroxide (28% aqueous solution) | 22.4 | ml |
| Water | 67 | ml |

Each of the light-sensitive elements (Samples 101 and 102) prepared above was exposed through a wedge, the processing solution was uniformly spread between the light-sensitive element and the dye image receiving sheet at a thickness of 60 μm and after allowing to stand for 2 minutes at 25° C., the dye image receiving sheet was separated to provide transferred images.

The results of sensitometery applied to each sample thus processed are shown in Table 1

TABLE 1

| | Maximum Density | | | Minimum Density | | |
|---|---|---|---|---|---|---|
| Sample | B | G | R | B | G | R |
| 101 (Comparison) | 1.78 | 2.20 | 2.60 | 0.24 | 0.21 | 0.30 |
| 102 (Invention) | 1.73 | 2.02 | 2.50 | 0.21 | 0.19 | 0.25 |

As is clear from the results shown in Table 1, it can be seen that Sample 102 of this invention containing the antifoggant-releasing compound of this invention gives images having less fog at background portions as compared to the comparison sample (Sample 101).

When Compound 18 or 23 was used in the above example in place of Compound 14, similar results were obtained.

EXAMPLE 2

A multilayer color photographic material (Sample 201) having the layers of the compositions shown below on a triacetyl cellulose film support having a subbing layer was prepared.

Compositions of the Layers

The coating amounts of silver halide and colloid silver were shown by $g/m^2$ unit of silver, the amounts of couplers, additives and gelatin were shown by $g/m^2$ unit, and the amount of sensitizing dyes was shown by mol per mol of the silver halide in the same emulsion layer.

| | |
|---|---|
| Layer 1 (Antihalation Layer) | |
| Black Colloid Silver | 0.2 |
| Gelatin | 1.3 |
| ExM - 9 | 0.06 |
| UV - 1 | 0.03 |
| UV - 2 | 0.06 |
| UV - 3 | 0.06 |
| Solv - 1 | 0.15 |
| Solv - 2 | 0.15 |
| Solv - 3 | 0.05 |
| Layer 2 (Interlayer) | |
| Gelatin | 1.0 |
| UV - 1 | 0.03 |
| ExC - 4 | 0.02 |
| ExF - 1 | 0.004 |
| Solv - 1 | 0.1 |
| Solv - 2 | 0.1 |
| Layer 3 (Low-Speed Red-Sensitive Emulsion Layer) | |
| Silver Iodobromide Emulsion (AgI 4 mol %, uniform AgI type, sphere-corresponding gran size 0.5 μm, variation coeff. of the grain size 20%, tabular grain, aspect ratio 3.0) | 1.2 (silver) |
| Silver Iodobromide Emulsion (AgI 3 mol %, uniform AgI type, sphere-corresponding grain size 0.3 μm, variation coeff. of the grain size 15%, pherical grain, aspect ratio 1.0) | 0.6 (silver) |
| Gelatin | 1.0 |
| ExS - 1 | $4 \times 10^{-4}$ |
| ExS - 2 | $5 \times 10^{-4}$ |
| ExC - 1 | 0.05 |
| ExC - 2 | 0.50 |
| ExC - 3 | 0.03 |
| ExC - 4 | 0.12 |
| ExC - 5 | 0.01 |
| Layer 4 (High-Speed Red-Sensitive Emulsion Layer) | |
| Silver Iodobromide Emulsion (AgI 6 mol %, Inside high AgI type of core/shell ratio of 1 : 1, sphere-corresponding grain size 0.7 μm, variation coeff. of the grain size 15%, tabular grain, aspect ratio 5.0) | 0.7 (silver) |
| Gelatin | 1.0 |
| ExS - 1 | $3 \times 10^{-4}$ |
| ExS - 2 | $2.3 \times 10^{-5}$ |
| ExC - 6 | 0.11 |
| ExC - 7 | 0.05 |
| ExC - 4 | 0.05 |
| Solv - 1 | 0.05 |
| Solv - 3 | 0.05 |
| Layer (Intelayer) | |
| Gelatin | 0.5 |
| Cpd | 0.1 |
| Solv - 1 | 0.05 |
| Layer 6 (Low-Speed Green-Sensitive Emulsion Layer) | |
| Silver Iodobromide Emulsion (AgI 14 mol %, surface high AgI type of core-shell of 1 : 1, sphere-corresponding grain size 0.5 μm, variation coeff. of the grain size 15%, tabular grain, aspect ratio 4.0) | 0.35 (silver) |
| Silver Iodobromide Emulsion (AgI 3 mol %, uniform AgI type, sphere-corresponding grain size 0.3 μm, variation coeff. of the grain size 25%, sphere grain, aspect ratio 1.0) | 0.20 (silver) |
| Gelatin | 1.0 |
| ExS - 3 | $5 \times 10^{-4}$ |
| ExS - 4 | $3 \times 10^{-4}$ |
| ExS - 5 | $1 \times 10^{-4}$ |
| ExM - 8 | 0.4 |
| ExM - 9 | 0.07 |
| ExM - 10 | 0.02 |
| ExY - 11 | 0.03 |
| Solv - 1 | 0.3 |
| Solv - 4 | 0.05 |
| Layer 7 (High-Speed Green-Sensitive Emulsion Layer) | |
| Silver iodobromide emulsion (AgI 4 mol %, inside high AgI type of core-shell of 1 : 3, sphere-corresponding grain size 0.7 μm, variation coeff. of the grain size 20%, tabular grain, aspect ratio 5.0) | 0.8 (silver) |
| ExS - 3 | $5 \times 10^{-4}$ |
| ExS - 4 | $3 \times 10^{-4}$ |
| ExS - 5 | $1 \times 10^{-4}$ |
| ExM - 8 | 0.1 |
| ExM - 9 | 0.02 |
| ExY - 11 | 0.03 |
| ExC - 2 | 0.03 |
| ExM - 14 | 0.01 |
| Solv - 1 | 0.2 |
| Solv - 4 | 0.01 |
| Layer 8 (Interlayer) | |
| Gelatin | 0.5 |
| Cpd - 1 | 0.05 |
| Solv - 1 | 0.02 |
| Layer 9 (Doner Layer of Double Effect to Red-Sensitive Emulsion Layer) | |
| Silver Iodobromide Emulsion (AgI 2 mol %, inside high AgI type of core-shell ratio of 2 : 1, sphere-corresponding grain size 1.0 μm, variation coeff. of the grain size 15%, tabular grain, aspect ratio 6.0) | 0.35 (silver) |
| Silver Iodobromide Emulsion (AgI 2 mol %, inside high AgI type of core-shell ratio of 1 : 1, sphere-corresponding grain size 0.4 μm, variation coeff. of the grain size 20%, tabular grain, aspect ratio 6.0) | 0.20 (silver) |
| Gelatin | 0.5 |
| ExS - 3 | $8 \times 10^{-4}$ |
| ExY - 13 | 0.11 |
| ExM - 12 | 0.03 |
| ExM - 14 | 0.10 |
| Solv - 1 | 0.20 |
| Layer 10 (Yellow Filter Layer) | |
| Black Colloid Silver | 0.05 |

-continued

-continued

| | |
|---|---|
| Gelatin | 0.5 |
| Cpd - 2 | 0.13 |
| Cpd - 1 | 0.10 |
| Layer 11 (Low-Speed Blue-Sensitive Emulsion Layer) | |
| Silver Iodobromide Emulsion (AgI 4.5 mol %, uniform AgI type, sphere-corresponding grain size 0.7 μm, variation coeff. of the grain size, tabular grain, aspect ratio 7.0) | 0.3 (silver) |
| Silver Iodobromide Emulsion (AgI 3 mol %, uniform AgI type, sphere-corresponding grain size 0.3 μm, variation coeff. of the grain size 25%, tabular grain, aspect ratio 7.0) | 0.15 (silver) |
| Gelatin | 1.6 |
| ExS - 6 | $2 \times 10^{-4}$ |
| ExC - 16 | 0.05 |
| ExC - 2 | 0.10 |
| ExC - 3 | 0.02 |
| ExY - 13 | 0.07 |
| ExY - 15 | 0.5 |
| ExY - 17 | 1.0 |
| Solv - 1 | 0.20 |
| Layer 12 (High-Speed Blue-Sensitive Emulsion Layer) | |
| Silver Iodobromide Emulsion (AgI 10 mol %, inside high AgI type, sphere-corresponding grain size 1.0 μm, variation coeff. of the grain size 25%, multilayer twin tabular grain, aspect ratio 2.0) | 0.5 (silver) |

-continued

| | |
|---|---|
| Gelatin | 0.5 |
| ExS - 6 | $1 \times 10^{-4}$ |
| ExY - 15 | 0.20 |
| ExY - 13 | 0.01 |
| Solv - 1 | 0.10 |
| Layer 13 (1st Protective Layer) | |
| Gelatin | 0.8 |
| UV - 4 | 0.1 |
| UV - 5 | 0.15 |
| Solv - 1 | 0.01 |
| Solv - 2 | 0.01 |
| Layer 14 (2nd Protective Layer) | |
| Fine Grain Silver Bromide Emulsion (AgI 2 mol %, uniform AgI type, sphere-corresponding gran size 0.07 μm) | 0.5 |
| Gelatin | 0.45 |
| Polymethyl Methacrylate Particle particle size 1.5 μm | 0.2 |
| H - 1 | 0.4 |
| Cpd - 3 | 0.5 |
| Cpd - 3 | 0.5 |

Each layer further contained a stabilizer Cpd-3 (0.04 $g/m^2$) for emulsion and a surface active agent Cpd-4 (0.02 $g/m^2$) as a coating aid. Furthermore, each layer also contained compounds Cpd-5 (0.5 $g/m^2$) and Cpd-6 (0.5 $g/m^2$) shown below.

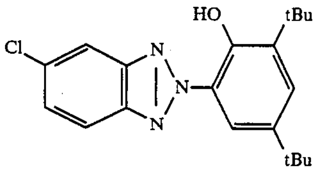

UV-1

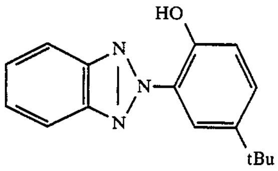

UV-2

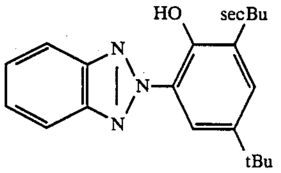

UV-3

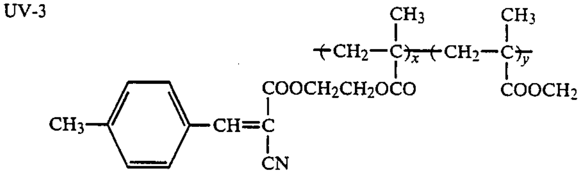

UV-4

(x/y = 7/3 (weight ratio))

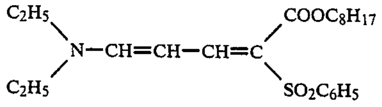

UV-5

Tricresyl Phosphate

Solv-1

Dibutyl Phthalate

Solv-2

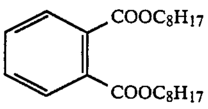

Solv-3

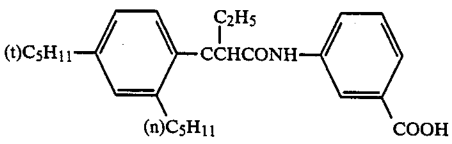

Solv-4

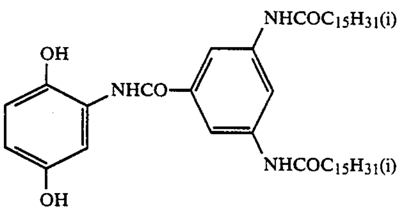

Cpd-1

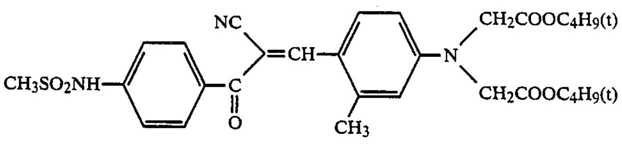

Cpd-2

-continued
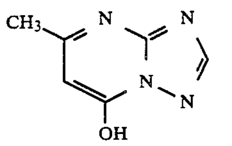
Cpd-3
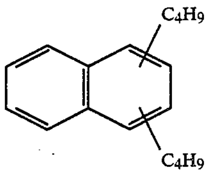
Cpd-4
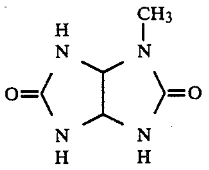
Cpd-5
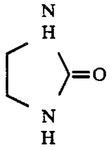
Cpd-6
ExC-1
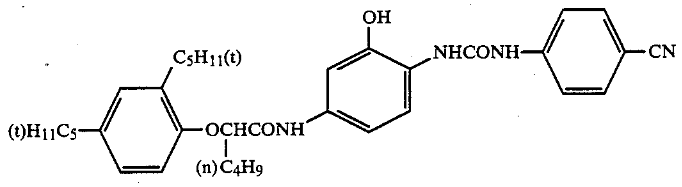
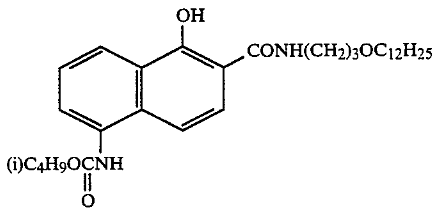
ExC-2
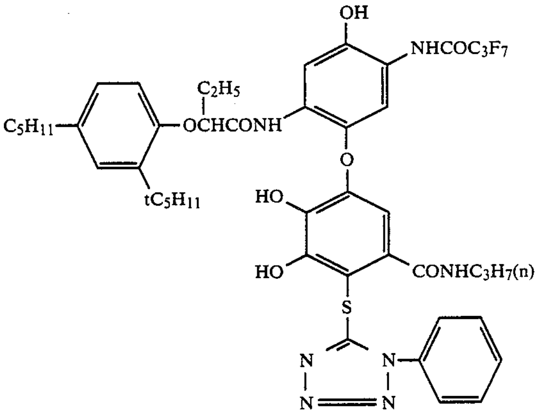
ExC-3
ExC-4
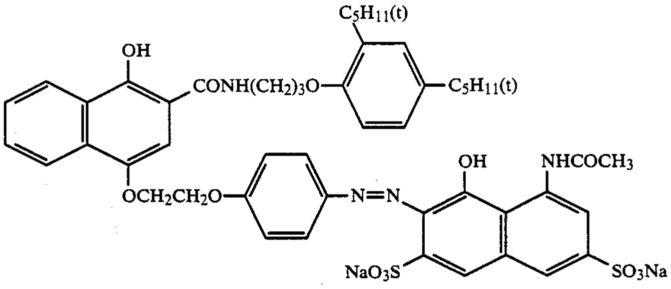
ExC-5
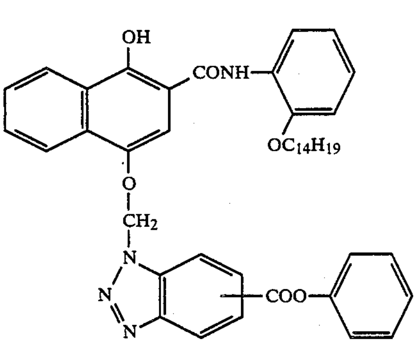

-continued
ExC-6
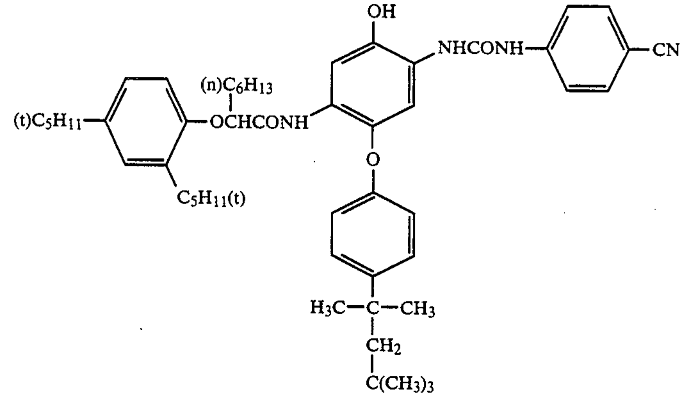
ExC-7
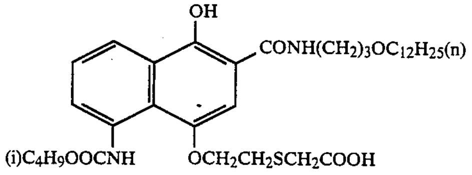
ExM-8
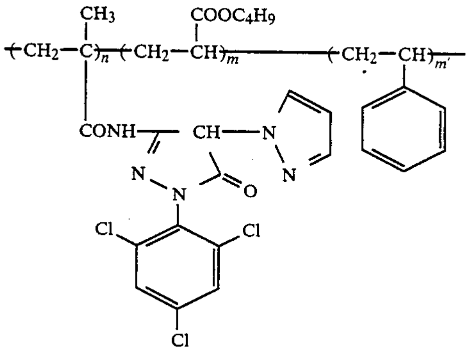
n = 50
m = 25
m' = 25
mol. wt. about 20,000
ExM-9
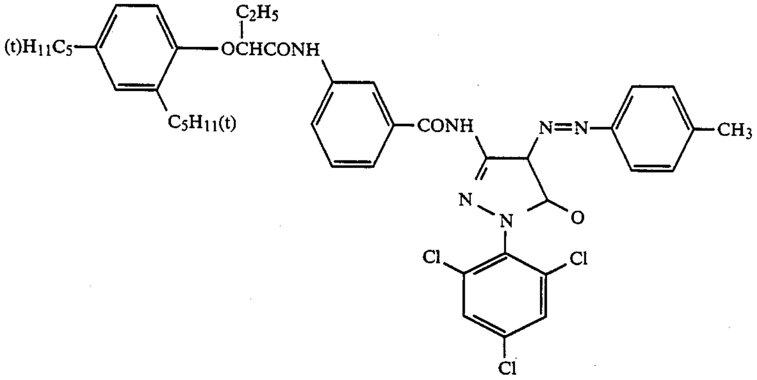
ExM-10
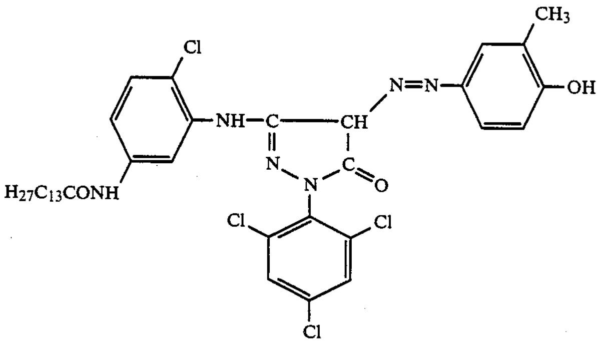

-continued
ExY-11
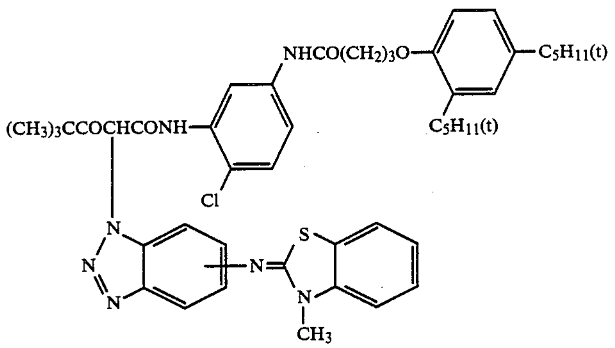
ExM-12
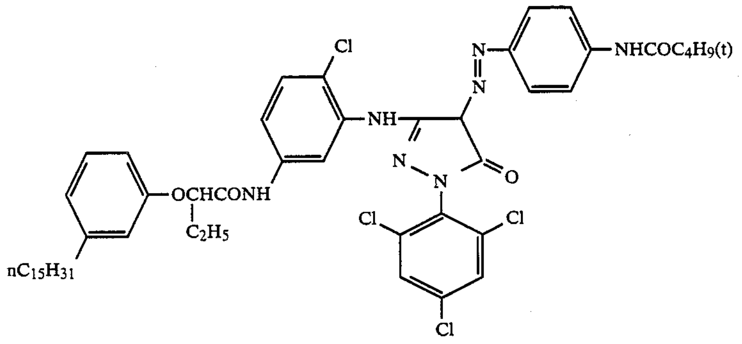
ExY-13
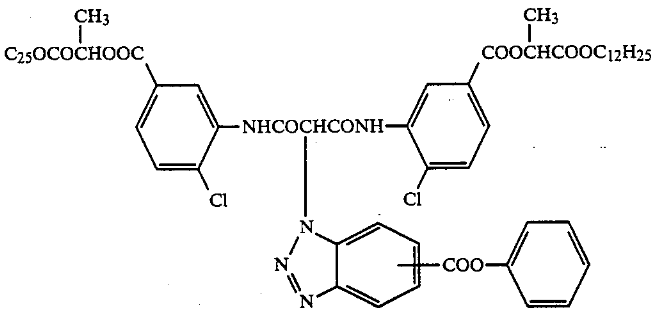
ExM-14
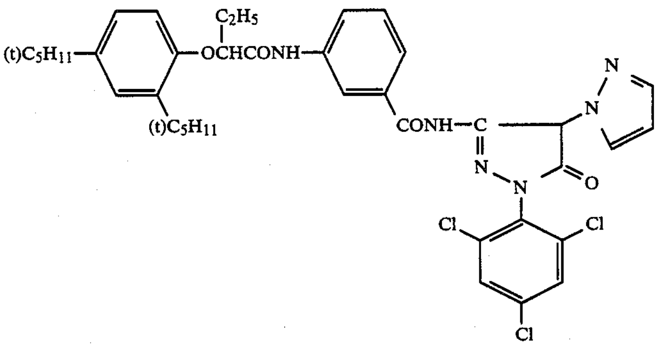

-continued
ExY-15
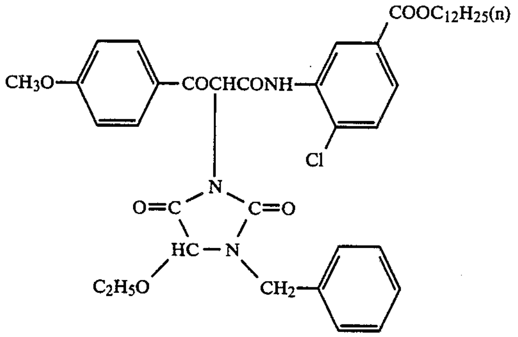
ExC-16
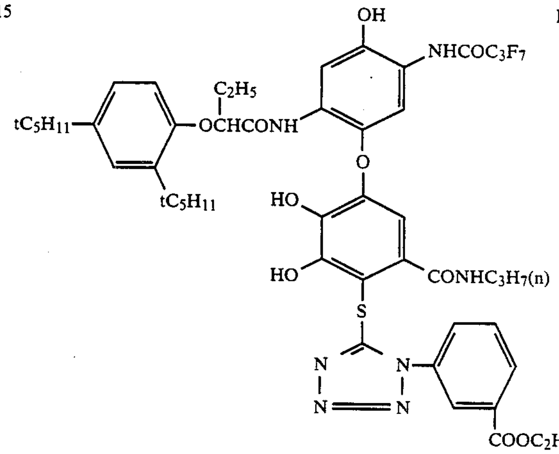
ExY-17
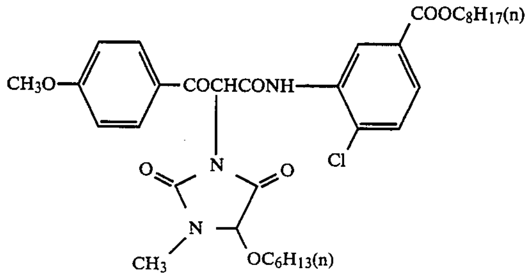
ExS-1
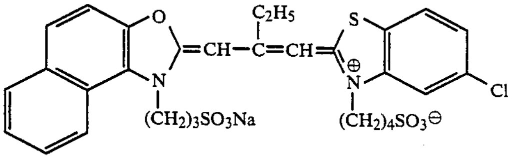
ExS-2
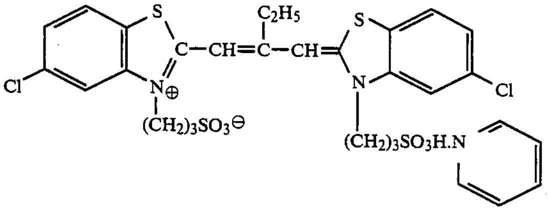
ExS-3
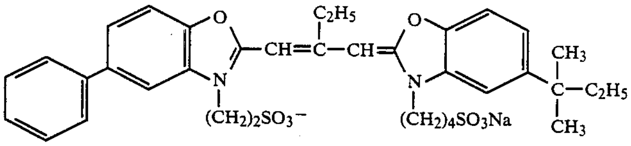
ExS-4
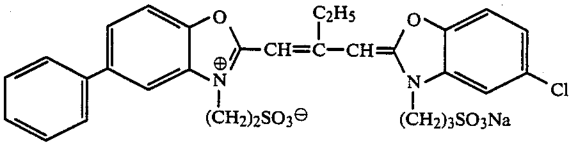
ExS-5
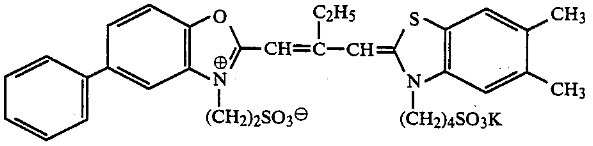
ExS-6
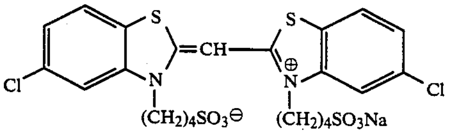
H-1
$CH_2{=}CH{-}SO_2{-}CH_2{-}CONH{-}CH_2$
$CH_2{=}CH{-}SO_2{-}CH_2{-}CONH{-}CH_2$ -continued

EXF-1

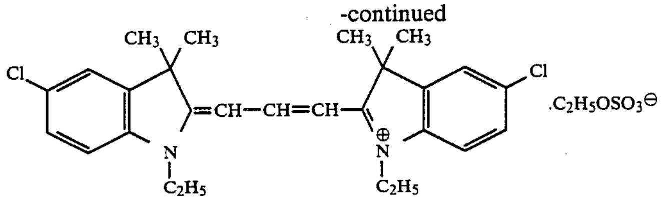

Preparation of Samples 202 to 205

By following the same procedure as employed for preparing Sample 201 except that the comparison compound AF-1 or compound 13 of this invention and ED 1 or 2 were added to Layer 4, Layer 7 and Layer 12 in the amounts shown in Table 2 below, Samples 201 to 205 were prepared.

Each of Samples 201 to 205 thus prepared was exposed by white light for sensitometery and then processed by following Process A or Process B and the results obtained are shown in Table 2 below.

| Process A | | |
|---|---|---|
| Color development | 3 min. 15 sec. | 38° C. |
| Bleach | 30 sec. | " |
| Blix | 1 min. 30 sec. | " |
| Rinse | 1 min. 40 sec. | " |
| Stabilization | 40 sec. | " |

The composition of each processing solution is as follows.

| | |
|---|---|
| **Color Developer** | |
| Diethylenetriaminepentaacetic acid | 1.0 g |
| 1-Hydroxyethylidene-1,1-diphosphonic Acid | 2.0 g |
| Sodium Sulfite | 4.0 g |
| Potassium Carbonate | 30.0 g |
| Potassium Bromide | 1.4 g |
| Potassium Iodide | 1.3 mg |
| Hydroxylamine Sulfate | 2.4 g |
| 4-(N—Ethyl-N—β-hydroxyethylamino)-2-methylaniline Sulfate | 4.5 g |
| Water to make | 1.0 liter |
| pH | 10.0 |
| **Bleach Solution** | |
| Ammonium Bromide | 100 g |
| Ethylenediaminetetraacetic Acid Ferric Ammonium Salt | 120 g |
| Ethylenediaminetetraacetic Acid Di-sodium Salt | 10.0 g |
| Ammonium Nitrate | 10.0 g |
| Bleach Accelerator | 2.0 g |
| Aqueous Ammonia | 17.0 ml |
| Water to make | 1 liter |
| pH | 6.5 |
| **Blix Solution** | |
| Ammonium Bromide | 50.0 g |
| Ethylenediaminetetraacetic Acid Ferric Ammonium Salt | 50.0 g |
| Ethylenediaminetetraacetic Acid Di-sodium Salt | 5.0 g |
| Ammonium Nitrate | 5.0 g |
| Sodium Sulfite | 12.0 g |
| Aqueous Solution of Ammonium Thiosulfate (70%) | 240 ml |
| Aqueous Ammonia | 10.0 ml |
| Water to make | 1 liter |
| pH | 7.3 |
| **Rinse Solution** | |
| Ethylenediaminetetraacetic Acid Di-sodium Salt | 0.4 g |
| Water to make | 1 liter |
| pH adjusted to 7.0 with sodium hydroxide | |

-continued

| | | |
|---|---|---|
| **Stabilization Solution** | | |
| Formaldehyde (40%) | | 2.0 ml |
| Polyoxyethylele-p-mononony1 Phenyl Ether (mean polymerization degree of about 10) | | 0.3 g |
| Water to make | | 1.0 liter |
| **Process B** | | |
| Color Development | 2 min. 30 sec. | 40° C. |
| Blix | 3 min. 00 sec. | 40° C. |
| Wash (1) | 20 sec. | 35° C. |
| Wash (2) | 20 sec. | 35° C. |
| Stabilization | 20 sec. | 35° C. |
| Dry | 50 sec. | 65° C. |

The composition of each processing solution is shown below.

| | | |
|---|---|---|
| **Color Developer** | | |
| Diethylenetriaminepentaacetic Acid | | 2.0 g |
| 1-Hydroxyethylidene-1,1-diphosphonic Acid | | 3.0 g |
| Sodium Sulfite | | 4.0 g |
| Potassium Carbonate | | 30.0 g |
| Potassium Bromide | | 1.4 g |
| Potassium Iodide | | 1.5 mg |
| Hydroxylamine Sulfate | | 2.4 g |
| 4-[N—Ethyl-N—(β-hydroxyethyl)-amino]-2-methylaniline Sulfate | | 4.5 g |
| Water to make | | 1 liter |
| | pH | 10.05 |
| **Blix Solution** | | |
| Ethylenediaminetetraacetic Acid Ferric Ammonium Di-hydrate | | 50.0 g |
| Ethylenediaminetetraacetic Acid Disodium Salt | | 5.0 g |
| Sodium Salt | | 5.0 g |
| Sodium Sulfite | | 12.0 g |
| Aqueous Solution of Ammonium Thiosulfate (70%) | | 260.0 ml |
| Acetic Acid (98%) | | 5.0 ml |
| Bleach Accelerator 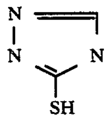 | | 0.01 mol |
| Water to make | | 1.0 liter |
| | pH | 6.0 |

Wash Water

City water was passed through a mixed bed type column packed with a H-type strong acid cation exchange resin (Amberlite IR-120B, trade name, made by Rhom and Haas Co.) and an OH type anion exchange resin (Amberlite IR-400) to reduce calcium and magnesium ion concentrations below 3 mg/liter and then 20 mg/liter of sodium dichloroisocyanurate and 1.5 g/liter of sodium sulfate were added to the water. The pH of the solution was in the range of from 6.5 to 7.5.

| Stabilization Solution | |
|---|---|
| Formaldehyde | 2.0 ml |
| Polyoxyethylene-p-monononylphenyl Ether (mean polymerization degree abour 10) | 0.3 g |
| Ethylenediaminetetraacetic Acid Di-sodium Salt | 0.05 g |
| Water to make | 1.0 liter |
| pH | 5.0 to 8.0 |

TABLE 2

| Sample No. | Layer | Compound and Amount (mol/mol Ag) | | ED and Amount (mol/mol/Ag) | | $\Delta S_{0.2}$* Process A | $\Delta S_{0.2}$* Process B | $\Delta D_{min}$** Process A | $\Delta D_{min}$** Process B |
|---|---|---|---|---|---|---|---|---|---|
| 1 | 4 | — | — | — | — | ±0 | ±0 | ±0 | ±0 |
| | 7 | — | — | — | — | ±0 | ±0 | ±0 | ±0 |
| | 12 | — | — | — | — | ±0 | ±0 | ±0 | ±0 |
| 2 | 4 | AF-1 | $0.5 \times 10^{-4}$ | — | — | −0.11 | −0.15 | −0.03 | −0.04 |
| | 7 | AF-1 | $0.8 \times 10^{-4}$ | — | — | −0.18 | −0.20 | −0.03 | −0.05 |
| | 12 | AF-1 | $1.2 \times 10^{-4}$ | — | — | −0.25 | −0.28 | −0.04 | −0.06 |
| 3 | 4 | — | — | ED-1 | $2.0 \times 10$ | −0.00 | −0.00 | −0.00 | −0.00 |
| | 7 | — | — | ED-1 | $3.2 \times 10$ | −0.00 | −0.00 | −0.00 | −0.00 |
| | 12 | — | — | ED-1 | $4.8 \times 10$ | −0.00 | −0.00 | −0.00 | −0.00 |
| 4 | 4 | 13 | $2.0 \times 10^{-4}$ | ED-1 | $2.0 \times 10$ | −0.04 | −0.04 | −0.03 | −0.02 |
| | 7 | 13 | $3.2 \times 10^{-4}$ | ED-11 | $3.2 \times 10$ | −0.04 | −0.05 | −0.03 | −0.02 |
| | 12 | 13 | $4.8 \times 10^{-4}$ | ED-1 | $4.8 \times 10$ | −0.08 | −0.08 | −0.04 | −0.04 |
| 5 | 4 | 13 | $3.0 \times 10^{-4}$ | ED-2 | $6.0 \times 10$ | −0.04 | −0.04 | −0.04 | −0.04 |
| | 7 | 13 | $4.0 \times 10^{-4}$ | ED-2 | $8.0 \times 10$ | −0.04 | −0.04 | −0.04 | −0.04 |
| | 12 | 13 | $5.0 \times 10^{-4}$ | ED-2 | $10.0 \times 10$ | −0.07 | −0.07 | −0.05 | −0.05 |

$\Delta S_{0.2}$: The changed amount of the logarithm of the exposure amount giving a density of fog + 0.2 to Sample 1.
**$\Delta D_{min}$: The changed amount of the minimum density to Sample 1.

AF-1

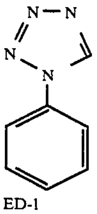

ED-1

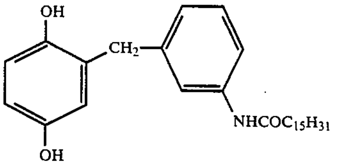

ED-2

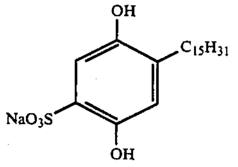

From the results shown in Table 2 above, it can be seen that the compouns of this invention effectively control the occurence of fog in the range of causing less reduction of sensitivity.

EXAMPLE 3

A light-sensitive element (Sample 301) was prepared by coating, in succession, the following layers on a transparent polyethylene terephthalate support.

Layer (I)

A light-sensitive layer contianing the following (a) to (f) and 1.2 $g/m^2$ of gelatin including the gelatin contained in above (a) to (d).

(a) Light-sensitive silver iodobromide emulsion (0.36 g-$Ag/m^2$)

(b) Benzotriazole silver emulsion (0.18 g-$Ag/m^2$)

(c) Compound 20 (0.27 $mmol/m^2$) of this invention and a gelatin dispersion of trecresyl phosphate (1 $g/m^2$).

(d) A gelatin dispersion of the reducing agent S-3 (0.27 mmol) and tricresyl phosphate (0.2 $g/m^2$).

(e) A basic precursor (0.44 $g/m^2$) having the following structure

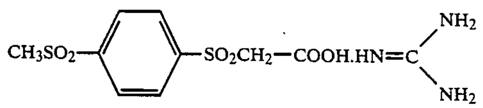

(f) A compound (0.1 $g/m^2$) having the following structure;

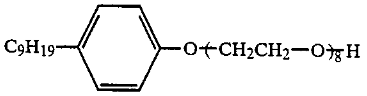

Layer (II)

A layer containing (a)' the aforesaid basic precursor ($0.74 g/m^2$) and gelatin ($1 g/m^2$).

Also, light-sensitive elements (Samples 302 and 303) were prepared by using Compound 15 and Compound 36, respectively in place of Compound 20 in Layer (I).

Each of the samples was exposed and then uniformly heated on a hot plate at 140° C. for 30 seconds. Then, after applying 8 $ml/m^2$ of water to the image-receiving sheet prepared in the same manner as in Example 1, the aforesaid light-sensitive element was closely brought into contact with the image-receiving sheet and after heating to 90° C. for 20 seconds, the image-receiving sheet was separated. Thus, positive color images were obtained on the image-receiving sheet.

The photographic performance of each image obtained by sensitometery is shown in Table 3 below.

TABLE 3

| Sample | Compound | Maximum Density (reflection) | Minimum Density |
|---|---|---|---|
| 201 | 20 | 1.08 | 0.35 |
| 202 | 15 | 0.99 | 0.30 |
| 203 | 36 | 0.89 | 0.22 |

From the results shown in Table 3, it can be seen that the compounds of this invention give good positive images and thus sufficiently function as positive working compounds.

While the invention has been described in detail and with rereference to specific embodiments thereof, it will be apparent to one skilled in the art that various changes and modifications can be made therein without departing from the spirit and the scope thereof.

What is claimed is:

1. A silver halide photographic material comprising a support having formed thereon at least one silver halide emulsion layer, wherein the silver halide photographic material contains, in the silver halide emulsion layer, other hydrophilic colloid layer(s), or both, a compound represented by formula (I)

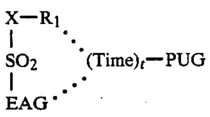

(I)

wherein EAG represents an electron accepting group, $-SO_2-$ represents a sulfonylene group; X represents an oxygen atom (—O—), a sulfur atom (—S—) or an atomic group ($-N(R_2)-$) containing a nitrogen atom; the single bond between $-SO_2$ and X being cleaved after EAG receives an electron, wherein $R_1$ and $R_2$ each represents a simple bond or a group other than a hydrogen atom; said $R_1$, $R_2$, EAG may be combined with each other to form a ring; (Time) represents a group capable of releasing a photographically useful group (PUG) upon the cleavage of the $SO_2$—X bond; t represents 0 or 1; when said t is 0, (Time) represents a simple bond and X may be a part of PUG; the solid line represents a bond; the dotted lines show that at least one of them is bonded.

2. The silver halide photographic material as claimed in claim 1, wherein the compound represented by formula (I) is a compound shown by formula (II)

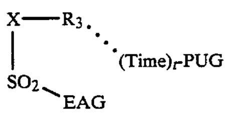

(II)

wherein $R_3$ represents an atomic group forming a 5- to 8-membered ring by combining with X and EAG; and $SO_2$, X, EAG, (Time), t, and PUG have the same meaning as defined in Formula (I).

3. The silver halide photographic material as claimed in claim 1, wherein $R_1$ and $R_2$ each represents a member selected from the group consisting of an alkyl group, an aralyl group, an aryl group, a heterocyclic group, an acyl group, a carbamoyl gorup, a sulfamoyl group or a sulfonyl group.

4. The silver halide photographic material as claimed in claim 1, wherein said compound of formula (I) is employed in an amount of from $1\times10^{-7}$ to $1\times10^{3}$ mol/mol of silver halide.

5. The silver halide photographic material as claimed in claim 1, wherein PUG is a diffusible dye and the amount of the compound of formula (I) is employed is 0.05 $millimol/m^2$ to 50 $millimols/m^2$.

6. The silver halide photographic material as claimed in claim 1, wherein PUG is a diffusible dye and the amount of the compound of formula (I) is employed is 0.1 $millimol/m^2$ to 5 $millimols/m^2$.

7. The silver halide photographic material as claimed in claim 1, wherein PUG is a development inhibitor and the amount of the compound of formula (I) employed is from $1\times10^{-7}$ to $1\times10^{-1}$ mol/mol of silver halide.

8. The silver halide photographic material as claimed in claim 1, wherein PUG is a development inhibitor and the amount of the compound of formula (I) is employed is $1\times10^{-3}$ mol to $1\times10^{-2}$ mol/mol of silver halide.

9. The silver halide photographic material as claimed in claim 1, wherein PUG is a silver halide solvent and the amount of the compound of formula (I) is employed is $1\times10^{-5}$ mol to $1\times10^{3}$ mol/mol of silver halide.

10. The silver halide photographic material as claimed in claim 1, wherein PUG is a silver halide solvent and the amount of the compound of formula (I) is employed is $1\times10^{-4}$ mol to $1\times10^{1}$ mol/mol of silver halide.

* * * * *